United States Patent [19]

Osborne

[11] Patent Number: 4,798,828

[45] Date of Patent: Jan. 17, 1989

[54] HETEROCYCLIC-METHYLENE-PENEMS

[75] Inventor: Neal F. Osborne, Rusper, England

[73] Assignee: Beecham Group p.l.c., Middlesex, England

[21] Appl. No.: 694,607

[22] Filed: Jan. 24, 1985

[30] Foreign Application Priority Data

Jan. 26, 1984 [GB] United Kingdom ............... 8402085
Jul. 11, 1984 [GB] United Kingdom ............... 8417659
Oct. 12, 1984 [GB] United Kingdom ............... 8425889

[51] Int. Cl.$^4$ ............... C07D 499/00; A61K 31/425
[52] U.S. Cl. ............................... 514/192; 514/195; 540/310; 540/354; 540/358
[58] Field of Search ............... 260/245.2 R, 245.2 T; 540/360, 310, 354, 358; 514/192, 195

[56] References Cited

U.S. PATENT DOCUMENTS 4,485,110 11/1984 Osborne ............... 260/245.2 R
4,517,124 5/1985 Bloom ............... 260/245.2 R

FOREIGN PATENT DOCUMENTS 0041768 4/1981 European Pat. Off. .

Primary Examiner—Nicholas S. Rizzo

Attorney, Agent, or Firm—Hopgood, Calimafde, Kalil, Blaustein & Judlowe

[57] ABSTRACT

Compounds of the general formula I:

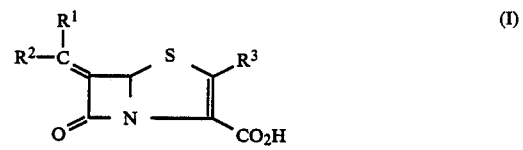

and their pharmaceutically acceptable salts and in vivo hydrolyzable esters, in which
  one of $R^1$ and $R^2$ denotes hydrogen,
  the other of $R^1$ and $R^2$ denotes an unsubstituted or substituted five-membered hetero-aromatic ring bonded through a carbon atom thereof and having one hetero-atom selected from nitrogen, oxygen and sulphur and additionally having from one to three nitrogen atoms, and
  $R^3$ denotes hydrogen or an organic group,
are novel compounds with $\beta$-lactamase inhibitory and antibacterial properties.

40 Claims, No Drawings

HETEROCYCLIC-METHYLENE-PENEMS

This invention relates to β-lactam compounds and in particular to a class of 6-alkylidene penems which have β-lactamase inhibitory and antibacterial properties. The compounds are therefore useful in the treatment of antibacterial infections in humans or animals, either alone or in combination with other antibiotics.

European Patent Publication No. EP 0 041 768 A (Beecham; published Dec. 16, 1981; corresponding to U.S. Ser. No 06/257 481) discloses 6-alkylidene-2-penems of the general formula (A):

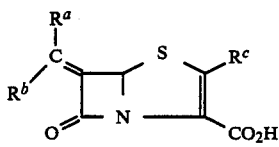

in which
each of $R^a$ and $R^b$ denotes hydrogen or an optionally substituted hydrocarbon or heterocyclic group, and
$R^c$ denotes hydrogen or an organic group.

Those compounds possess antibacterial activity and also inhibit β-lactamases and have a synergistic effect in combination with other β-lactam antibiotics.

European Patent Publication No. EP 0 120 613 A (Beecham; published Oct. 3, 1984; corresponding to U.S. Ser. No. 06/585 569) discloses a sub-group of compounds within the general formula (A) which have better activity than other compounds of the general formula (A). That sub-group consists of compounds of the general formula (B):

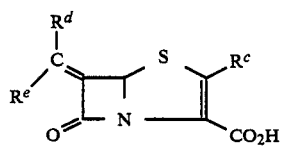

in which
$R^c$ denotes hydrogen or an organic group;
one of $R^d$ and $R^e$ denotes hydrogen, and
the other of $R^d$ and $R^e$ denotes a group of the sub-formula (C):

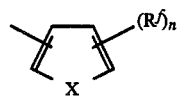

in which
$R^f$ denotes a substituent group;
X denotes an oxygen atom, a sulphur atom or an $=NR^g$ group;
$R^g$ denotes hydrogen, hydrocarbon or a nitrogen-protecting group; and
n denotes 0, 1, 2 or 3.

It has now been found that certain compounds of the general formula (A) exhibit improved β-lactamase inhibitory action and synergistic activity as compared with other compounds of that group.

According to the present invention there is provided a compound of the general formula I:

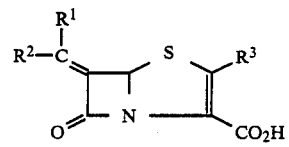

or a pharmaceutically acceptable salt or in vivo hydrolysable ester thereof in which
one of $R^1$ and $R^2$ denotes hydrogen,
the other of $R^1$ and $R^2$ denotes an unsubstituted or substituted five-membered hetero-aromatic ring bonded through a carbon atom thereof and having one hetero-atom selected from nitrogen, oxygen and sulphur and additionally having from one to three nitrogen atoms, and
$R^3$ denotes hydrogen or an organic group.

The hetero-aromatic ring (which may also be referred to as a hetero-aryl ring) denoted by $R^1$ or $R^2$ contains five ring atoms, two, three or four of which may be hetero-atoms (that is to say, non-carbon atoms). The ring hetero-atoms may be solely nitrogen atoms, in which case there may be two, three or four ring nitrogen atoms, or the ring hetero-atoms may consist of one oxygen or sulphur atom plus one, two or three nitrogen atoms. The hetero-aromatic ring is bonded to the methylene carbon atom through a ring carbon atom.

The hetero-aromatic ring may be unsubstituted or may be substituted by one or more substituents, each of which may be carried on a ring carbon atom or a ring nitrogen atom, provided of course that the aromaticity of the ring is not destroyed.

Examples of suitable substituents which may be present in the hetero-aromatic ring $R^1$ or $R^2$ include $(C_{1-6})$alkanoyl, $(C_{1-6})$alkanoyloxy, heterocyclyl, amino, $(C_{1-6})$alkanoylamino, (mono or di)-$(C_{1-6})$alkylamino, hydroxy, $(C_{1-6})$alkoxy, sulpho, mercapto, $(C_{1-6})$alkylthio, $(C_{1-6})$alkylsulphinyl, $(C_{1-6})$alkylsulphonyl, heterocyclylthio, arylthio, sulphamoyl, carbamoyl, amidino, guanidino, nitro, halogen, carboxy, carboxy salts, carboxy esters, arylcarbonyl, and heterocyclylcarbonyl groups, and also unsubstituted or substituted $(C_{1-6})$alkyl, $(C_{2-6})$alkenyl, $(C_{2-6})$alkynyl, aryl, and aryl$(C_{1-6})$alkyl groups.

Examples of suitable optional substituents for the above-mentioned $(C_{1-6})$alkyl, $(C_{2-6})$alkenyl, $(C_{2-6})$alkynyl, aryl and aryl$(C_{1-6})$alkyl substitutents include $(C_{1-6})$alkanoyl, $(C_{1-6})$alkanoyloxy, heterocyclyl, amino, $(C_{1-6})$alkanoylamino, (mono or di)-$(C_{1-6})$alkylamino, hydroxy, $(C_{1-6})$alkylsulphinyl, $(C_{1-6})$alkylsulphonyl, heterocyclylthio, arylthio, sulphamoyl, carbamoyl, amidino, guanidino, nitro, halogen, carboxy, carboxy salts, carboxy esters, arylcarbonyl and heterocyclylcarbonyl groups.

When the hetero-aromatic ring $R^1$ or $R^2$ includes a carboxy salt or carboxy ester substituent, that substituent is suitably a pharmaceutically acceptable salt or pharmaceutically acceptable ester.

The term 'heterocyclyl' as used herein includes aromatic and non-aromatic, single and fused, rings containing up to four hetero-atoms in each ring selected from oxygen, nitrogen and sulphur, which rings may be unsubstituted or substituted by up to three groups selected from halogen, $(C_{1-6})$alkyl, $(C_{1-6})$alkoxy, halo$(C_{1-6})$alkyl, hydroxy, amino, carboxy, $(C_{1-6})$alkoxycarbonyl, $(C_{1-6})$alkoxycarbonyl$(C_{1-6})$alkyl, aryl, $(C_{1-6})$alkylthio, arylthio, mercapto and oxo groups.

The term 'aryl' as used herein includes phenyl and naphthyl, which may be unsubstituted or substituted by up to five, preferably up to three, groups selected from halogen, $(C_{1-6})$alkyl, phenyl, $(C_{1-6})$alkoxy, halo$(C_{1-6})$alkyl, hydroxy, amino, nitro, carboxy, $(C_{1-6})$alkoxycarbonyl,$(C_{1-6})$alkoxycarbonyl$(C_{1-6})$alkyl, $(C_{1-6})$alkylcarbonyloxy, $(C_{1-6})$alkylcarbonyl $(C_{1-6})$alkylthio, arylthio, and mercapto groups.

The term 'hydrocarbon' as used herein includes groups having up to 18 carbon atoms, suitably up to 10 carbon atoms, conveniently up to 6 carbon atoms. Suitable hydrocarbon groups include $(C_{1-6})$alkyl, $(C_{2-6})$alkenyl, $(C_{2-6})$alkynyl, $(C_{3-7})$cycloalkyl, $(C_{3-7})$cycloalkyl$(C_{1-6})$alkyl, aryl, and aryl$(C_{1-6})$alkyl.

Suitably, one of $R^1$ and $R^2$ denotes hydrogen and the other of $R^1$ and $R^2$ denotes a five-membered hetero-aromatic ring of the type defined above that is unsubstituted or is substituted by one or more $(C_{1-6})$alkyl groups, for example methyl groups.

Suitable five-membered hetero-aromatic rings $R^1$ or $R^2$ include pyrazoles, imidazoles, triazoles, tetrazoles, thiazoles, isothiazoles, oxazoles, isoxazoles, thiadiazoles, and oxadiazoles, each of which may be unsubstituted or substituted. (It is to be understood that, where appropriate, all isomeric forms of the above-mentioned hetero-aromatic rings are included).

Particularly suitable hetero-aromatic rings $R^1$ or $R^2$ include oxazoles, isoxazoles, pyrazoles, and triazoles.

Advantageously, the hetero-aromatic ring $R^1$ and $R^2$ includes at least two ring nitrogen atoms.

Examples of individual hetero-aromatic groups $R^1$ or $R^2$ include isothiazolyl, isoxazolyl, methylthiazolyl, methyloxazolyl, dimethyloxazolyl, methyl-1,2,3-thiadiazolyl, methyl-1,2,4-oxadiazolyl, N-methylpyrazolyl, N-methylimidazolyl, N-methyl-1,2,3-triazolyl, N-methyl-1,2,4-triazolyl, and N-methyltetrazolyl groups.

In general formula I, $R^3$ denotes hydrogen or an organic group, which may suitably be linked through a sulphur or carbon atom. For example, $R^3$ may represent hydrogen or a group of formula $-R^4$ or $-SR^4$, where $R^4$ denotes an unsubstituted or substituted $(C_{1-10})$hydrocarbon or heterocyclyl group. Preferably, $R^3$ represents hydrogen, $(C_{1-10})$alkyl or $(C_{1-10})$alkylthio, or substituted $(C_{1-10})$alkyl or substituted $(C_{1-10})$alkylthio, wherein the substituent may be hydroxy, $(C_{1-6})$alkoxy, $(C_{1-6})$alkanoyloxy, halogen, mercapto, $(C_{1-6})$alkylthio, heterocyclylthio, amino, (mono or di)-$(C_{1-6})$alkylamino, $(C_{1-6})$alkanoylamino, carboxy, or $(C_{1-6})$alkoxycarbonyl.

Examples of suitable organic groups $R^3$ include methyl, ethyl, propyl, methylthio, ethylthio, methylsulphinyl, ethylsulphinyl, hydroxymethyl, methoxymethyl, ethoxymethyl, acetoxymethyl, (1 or 2)-acetoxyethyl, aminomethyl, 2-aminoethyl, acetamidomethyl, 2-acetamidoethyl, carboxymethyl, 2-hydroxyethylthio, methoxymethylthio, 2-methoxyethylthio, acetoxymethylthio, 2-aminoethylthio, acetamidomethylthio, 2-acetamidoethylthio, carboxymethylthio, 2-carboxyethylthio, aryl (especially phenyl), arylthio (especially phenylthio), pyridyl, pyrimidyl, isoxazolyl, pyrimidylthio, tetrazolylthio, and pyridylthio groups. In particular, $R^3$ may be hydrogen.

Pharmaceutically acceptable in vivo hydrolysable esters (also referred to as 'metabolisable esters') of the compounds of the general formula I are those esters which hydrolyse in the human body to produce the parent acid or its salt. Such esters may be identified by oral or intravenous administration to a test animal, and subsequent examination of the test animal's body fluids for the presence of the compound of the formula I or a salt thereof.

In some cases, the in vivo hydrolysable ester moiety may constitute a link between two different active ingredient moieties, one of which is a compound according to the invention and the other of which may be another therapeutically active compound, such that on in vivo hydrolysis of the ester moiety, the ester link breaks to give the two separate active compounds. The linked entity may be referred to as a 'mutual pro-drug'.

Suitable in vivo hydrolysable ester groups include those of part-formulae (a), (b) and (c):

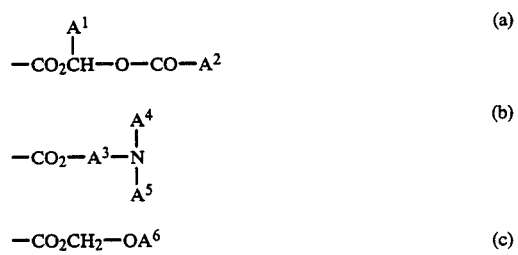

in which $A^1$ denotes hydrogen, methyl, or phenyl;

$A^2$ denotes $(C_{1-6})$alkyl, $(C_{1-6})$alkoxy or phenyl; or $A^1$ and $A^2$ together denote 1,2-phenylene, which may be unsubstituted or substituted by one or two methoxy groups;

$A^3$ denotes $(C_{1-6})$alkylene, which may be unsubstituted or substituted by a methyl or ethyl group;

each of $A^4$ and $A^5$ which may be identical or different, denotes $(C_{1-6})$alkyl; and $A^6$ denotes $(C_{1-6})$alkyl.

Examples of suitable in vivo hydrolysable ester groups include acetoxymethyl, pivaloyloxymethyl, α-acetoxyethyl, α-acetoxybenzyl, α-pivaloyloxyethyl, ethoxycarbonyloxymethyl, α-ethoxycarbonyloxyethyl, dimethylaminomethyl, diethylaminomethyl, phthalidyl and dimethoxyphthalidyl groups.

Suitable pharmaceutically acceptable salts of the 3-carboxylic acid group of the compound of formula I include metal salts, e.g. aluminium salts, alkali metal salts (e.g. sodium or potassium salts), alkaline earth metal salts (e.g. calcium or magnesium salts), ammonium salts, and substituted ammonium salts, for example those with lower alkylamines (e.g.triethylamine) hydroxy-lower alkylamines (e.g. 2-hydroxyethylamine), di(2-hydroxyethyl)amine or tri(2-hydroxyethyl)amine), cycloalkylamines (e.g. dicyclohexylamine), or with procaine, and also dibenzylamine, N,N-dibenzylethylenediamine, 1-ephenamine, N-ethylpiperidine, N-benzyl-β-phenethylamine, dehydroabietylamine, N,N'-bishydroabietylethylene-diamine, bases of the pyridine type (e.g. pyridine, collidine and quinoline), and other amines which have been or can be used to form salts with penicillins.

The compounds of the general formula I and also the salts and esters thereof may exist in two optically active forms and it is to be understood that both such forms as well as racemic mixtures thereof are embraced by the present invention. It is believed that the more active form is that of structure IA:

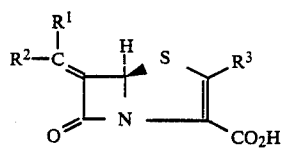

in which $R^1$, $R^2$ and $R^3$ are defined as above.

Furthermore, in general formulae I and IA, it is thought to be advantageous that $R^1$ denotes the heteroaromatic group and that $R^2$ denotes a hydrogen atom.

Examples of individual compounds according to the invention include:

(5RS) (Z)-6-(isothiazol-5-ylmethylene)penem-3-carboxylic acid;
(5RS) (E)-6-[(1-methylpyrazol-4-yl)methylene]penem-3-carboxylic acid;
(5RS) (Z)-6-[(1-methylpyrazol-4-yl)methylene]penem-3-carboxylic acid;
(5RS) (Z)-6-[(2-methylthiazol-4-yl)methylene]penem-3-carboxylic acid;
(5RS) (Z)-6-(isoxazol-3-ylmethylene)penem-3-carboxylic acid;
(5RS) (Z)-6-[(2,4-dimethyloxazol-5-yl)methylene]penem-3-carboxylic acid;
(5RS) (E)-6-[(4-methyl-1,2,3-thiadiazol-5-yl)methylene]penem-3-carboxylic acid;
(5RS) (Z)-6-[(4-methyl-1,2,3-thiadiazol-5-yl)methylene]penem-3-carboxylic acid;
(5RS) (Z)-6-[(2-methyloxazol-4-yl)methylene]penem-3-carboxylic acid;
(5RS) (Z)-6-[(1-methyl-1,2,3-triazol-4-yl)methylene]penem-3-carboxylic acid;
(5RS) (E)-6-[(1-methyl-1,2,3-triazol-4-yl)methylene]penem-3-carboxylic acid;
(5R) (Z)-6-[(1-methyl-1,2,3-triazol-4-yl)methylene]penem-3-carboxylic acid;
(5RS) (Z)-6-[(5-methyl-1,2,4-oxadiazol-3-yl)methylene]penem-3-carboxylic acid;
(5RS) (Z)-6-[(1-methyl-1,2,4-triazol-3-yl)methylene]penem-3-carboxylic acid;
(5RS) 2-hydroxymethyl-6(Z)-[(1-methylpyrazol-4-yl)methylene]penem-3-carboxylic acid;
(5RS) 2-ethylthio-6(Z)-[(1-methylpyrazol-4-yl)methylene]penem-3-carboxylic acid;
(5RS) 2-(2-hydroxyethylthio)-6(Z)-[(1-methylpyrazol-4-yl)methylene]penem-3-carboxylic acid;
(5RS) (Z)-6-(N-methyltetrazol-5-ylmethylene)penem-3-carboxylic acid;
(5RS) (Z)-6-[(1-methylpyrazol-3-yl)methylene]penem-3-carboxylic acid;
(5RS) (Z)-6-[(1-methylimidazol-4-yl)methylene]penem-3-carboxylic acid;
and pharmaceutically acceptable salts and in-vivo hydrolysable esters thereof.

A compound of the general formula I, or a salt or ester thereof, may be prepared by eliminating the elements of a compound of the general formula II:

$$H-X \qquad \text{II}$$

from a penem or penem intermediate of the general part-formula III:

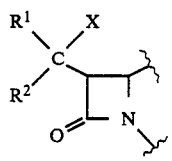

in which
$R^1$ and $R^2$ are defined as above, and
X denotes a hydroxy group or a leaving group,
to give a compound of the general part-formula IV:

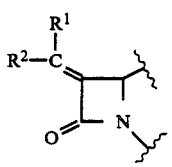

in which $R^1$ and $R^2$ are defined as above, and, if the resulting compound of the general formula IV is a penem intermediate, converting it into a penem of the general formula I or a salt or ester thereof.

The compound of the general part-formula III may suitably be a compound of the general part-formula IIIA:

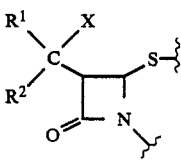

in which $R^1$, $R^2$ and X are defined as above. More especially it may be a compound of the general formula IIIB:

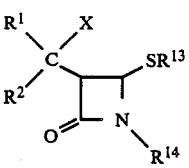

in which
$R^1$, $R^2$ and X are defined as above,
$R^{13}$ denotes $(C_{1-6})$alkyl, aryl, aryl$(C_{1-6})$alkyl, $(C_{1-6})$alkylthio, arylthio, hetero-aromatic-thio, acyl (for example, $(C_{1-6})$alkylcarbonyl, especially acetyl), $(C_{2-6})$alkenyl (especially vinyl), or aryl$(C_{2-6})$alkenyl, all of which may optionally be substituted, and
$R^{14}$ denotes hydrogen or an N-protecting group, or
$R^{13}$ and $R^{14}$ together denote the remainder of a penem nucleus, which may be substituted and/or may optionally carry a protecting group.

In the case where $R^{13}$ and $R^{14}$ in general formula IIIB together denote the remainder of a penem nucleus, they may suitably together denote the sub-formula V:

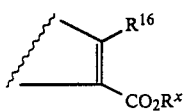

in which
- $R^{16}$ denotes the hydrogen atom or organic group $R^3$ or a group convertible into $R^3$ during the preparation of a penem of the general formula I or salt or ester thereof, and
- $R^x$ denotes hydrogen or a carboxyl-blocking group.

In that case, the penem or penem intermediate of the general part-formula III is of the general formula IIID given below.

A carboxyl-blocking group $R^x$ (also referred to as a carboxyl-protecting group) is suitably a group that can readily be removed at a later stage of the penem preparation process.

Examples of suitable carboxyl-blocking derivatives that may form the group $-CO_2R^x$ include salt, ester, and anhydride derivatives of the carboxylic acid.

The salts may be organic or inorganic and need not be pharmaceutically acceptable. Examples of suitable salt-forming groups $R^x$ include inorganic salts, for example alkali metal atoms (e.g. lithium and sodium), other metal atoms, tertiary amino groups (e.g. tri-lower-alkylamino, N-ethylpiperadino, and dimethylpiperazino groups). A preferred salt-forming group $R^x$ is the triethylamino group.

An ester-forming group $R^x$ is advantageously one that can be removed under conventional conditions. Examples of suitable ester-forming groups $R^x$ include benzyl, p-methoxybenzyl, 2,4,6-trimethylbenzyl, 3,5-di-t-butyl-4-hydroxy-benzyl, benzoylmethyl, p-nitrobenzyl, 4-pyridylmethyl, 2,2,2-trichloroethyl, 2,2,2-tribromoethyl, allyl, acetonyl, t-butyl, t-amyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, p-toluene-sulphonylethyl, and methoxymethyl groups, and also silyl, stannyl and phosphorus-containing groups, and oxime radicals of formula $-N=CHR^o$ in which $R^o$ denotes aryl or heterocyclyl. Furthermore, the ester-forming group $R^x$ may be an in vivo hydrolysable ester group including, in particular, those listed above.

The free carboxyl group may be regenerated from any of the above esters by usual methods appropriate to the particular $R^x$ group, for example, by acid-catalysed, base-catalysed or enzymically-catalysed hydrolysis, or by hydrogenation. The hydrolysis must of course be carried out under conditions in which the groups on the rest of the molecule are stable.

When it is desired to produce a compound of the general formula I in the form of a free acid or in the form of a salt, by a process according to the invention, it is generally advantageous to use a compound in which $R^x$ denotes a carboxyl-blocking group. When it is desired to produce a compound of the general formula I in the form of a pharmaceutically acceptable ester, it is generally convenient to use a compound in which $R^x$ denotes the desired ester group.

The process step according to the invention involves the elimination of the elements of a compound H—X from a penem or penem intermediate of the general part-formula III, in which X denotes a hydroxy group or a leaving group.

In the case where X denotes a hydroxy group, the compound of the formula H—X being eliminated is water and the elimination reaction is a dehydration reaction, which may suitably be carried out by treating a compound of the general part-formula III with a compound of the general formula VI:

$$R^6O_2C-N=N-CO_2R^7 \qquad VI$$

in which each of $R^6$ and $R^7$, which may be identical or different, denotes aryl, $(C_{1-6})$alkyl or aryl$(C_{1-6})$alkyl, and a with compound of the general formula VII:

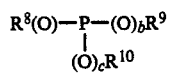

in which
- each of a, b and c which may be identical or different, denotes 0 or 1, and
- each of $R^8$, $R^9$ and $R^{10}$, which may be identical or different, denotes aryl, $(C_{1-6})$alkyl or aryl$(C_{1-6})$alkyl.

In the compounds of the general formula VI, $R^6$ and $R^7$ are preferably selected from methyl, ethyl, propyl, butyl, phenyl, and benzyl, the ethyl and isopropyl groups being preferred. Advantageously, $R^6$ and $R^7$ may be identical. A preferred compound of the general formula VI is diethyl azodicarboxylate.

Preferred compounds of the general formula VII include triarylphosphines and trialkylphosphites. Preferred groups $R^8$, $R^9$ and $R^{10}$ include methyl, ethyl, n-propyl, n-butyl, benzyl, phenyl and methoxyphenyl. Advantageously, $R^8$, $R^9$ and $R^{10}$ are all identical. A preferred compound of the general formula VII is triphenylphosphine.

Advantageously, approximately two equivalents of each the compounds of the general formulae VI and VII are used per mole of the compound of the general part-formula III.

The dehydration reaction may suitably be carried out at a non-extreme temperature, for example a temperature of from $-20°$ C. to $+100°$ C. It may be convenient to begin the reaction at a depressed temperature, for example $0°$ C., and then to allow the temperature to rise to about room temperature.

The reaction may suitably be carried out in an inert aprotic organic solvent. Suitable solvents include tetrahydrofuran, dioxane, ethyl acetate, benzene, and dichloromethane.

In the cases where X, in general formula III, denotes a leaving group, which will hereinafter be referred to as $X^1$, it may suitably be a halogen atom or a group of one of the formulae $$-O-SO_2-(O)_n-R^{11} \qquad VIIIA$$

$$-O-CO-(O)_n-R^{11} \qquad VIIIB \text{ or}$$

$$-O-PO-(OR^{12})_2 \qquad VIIIC$$

in which
- n denotes 0 or 1,
- $R^{11}$ denotes $(C_{1-6})$alkyl, aryl or aryl$(C_{1-6})$alkyl, and
- $R^{12}$ denotes $(C_{1-6})$alkyl or aryl.

Preferred groups of formula VIIIB are those in which n denotes zero and $R^{11}$ denotes $(C_{1-6})$alkyl, especially the acetoxy group.

The elimination of the elements of a compound of the general formula II in which X denotes a leaving group $X^1$ from a compound of the general formula III, may suitably be effected by treating the compound of the general formula III with a base in an aprotic medium.

Suitable bases for that purpose include, for example, powdered inorganic bases, for example alkali metal carbonates, bicarbonates, hydroxides, and hydrides (e.g. powdered potassium carbonate), and also organic bases of low nucleophilicity, for example 1,8-diazabicyclo[5.4.0]undec-7-ene. Suitable solvents for use as the aprotic medium in this reaction include, for example, dimethylformamide, hexamethylphosphoramide, dichloromethane, and tetrahydrofuran.

The elimination may suitably be effected at a low temperature, for example a temperature of from $-70°$ C. to $+70°$ C., advantageously from $-40°$ C. to $0°$ C.

The compounds of the general formula III in which X denotes a leaving group $X^1$ may suitably be prepared from the corresponding compound in which X denotes a hydroxy group by replacing the hydroxy group by a leaving group $X^1$. Alternatively, in the case of the compounds of the general formula IIID below, the leaving group $X^1$ may be introduced into the molecule at an earlier stage in the synthesis of the penem nucleus. In particular, a group $X^1$ of the formula VIIIA or VIIIB may be introduced at the beginning of, or at any stage during, the synthesis of the penem. In each case, the group $X^1$ may suitably be introduced by replacing a hydroxyl group in known manner.

The dehydration or other elimination reaction of the process according to the invention may be carried out at any suitable stage during the preparation of the penem of the general formula I or salt or ester thereof, suitably at an early stage or late stage in the manufacturing process.

Further examples of suitable leaving groups will be apparent to those skilled in the art and include sulphoxide, selenoxide and xanthate groups, which can be eliminated by known methods (see W. Carruthers, 'Some modern methods of organic synthesis', Cambridge Univ. Press 1978 (2nd edition), pages 93–103).

In particular, the dehydration or other elimination reaction may be carried out on a compound of the general formula IIIC:

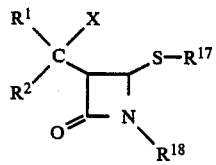     IIIC in which
$R^1$, $R^2$ and X are defined as above,
$R^{17}$ denotes ($C_{1-6}$) alkyl, aryl, aryl($C_{1-6}$)alkyl, ($C_{1-6}$)alkylthio, arylthio, hetero-aromatic-thio, acyl (for example, ($C_{1-6}$)alkylcarbonyl, especially acetyl), ($C_{2-6}$)alkenyl (especially vinyl), or aryl($C_{2-6}$)alkenyl, all of which may optionally be substituted, and
$R^{18}$ denotes hydrogen or an N-protecting group, to give a compound of the general formula IVC:

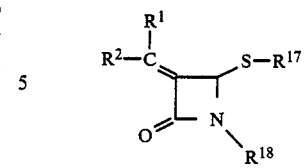     IVC in which, $R^1$, $R^2$, $R^{17}$ and $R^{18}$ are defined as above, which may then subsequently be converted to a penem of the general formula I or salt or ester thereof in known manner, suitably by a conventional penem preparation method.

Alternatively, the dehydration or other elimination reaction may be carried out on a compound of the general formula IIID:

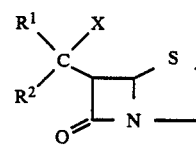     IIID in which $R^1$, $R^2$, $R^{16}$, $R^x$ and X are defined as above, to give a compound of the general formula IVD:

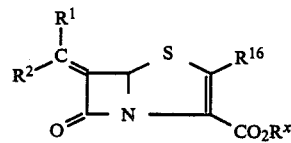     IVD in which $R^1$, $R^2$, $R^{16}$ and $R^x$ are defined as above, and thereafter, if necessary or desired:

(a) removing any carboxyl-blocking group $R^x$, and/or (b) converting the group $R^{16}$ into a group or atom $R^3$, and/or (c) converting the product into the free acid or into a pharmaceutically acceptable salt or in vivo hydrolysable ester.

The conversion of a compound of the general formula IVC to the desired penem may suitably proceed via a compound of the general formula IVD, according to known penem preparation methods.

A compound of the general formula IIID, especially one in which X denotes a leaving group $X^1$, may conveniently be prepared from a compound of the general formula IIIC, especially one in which X denotes a leaving group $X^1$, according to known penem preparation methods.

In a compound of the general formula IIIB or IIIC, $R^{13}$ or $R^{17}$, respectively, may suitably denote a triphenylmethyl group. Examples of suitable N-protecting groups, $R^{14}$ or $R^{18}$, include silyl groups, for example t-butyldimethylsilyl groups.

In the general formula IIID and IVD, the group $R^{16}$ may be a group convertible into $R^3$ during the penem preparation process. One particular example of such a group, which may conveniently be used in the preparation of a group $R^3$ of the formula $-SR^4$ (in which $R^4$ is defined as above), is the group of the formula IX:

in which $R^{15}$ denotes an organic radical different from the group $R^4$.

A sulphoxide compound of the general formula IIID or IVD in which $R^{16}$ denotes a group of the formula IX may be reacted with a thiol of the general formula XI:

$$R^4\text{—SH} \qquad \qquad XI$$

in which $R^4$ is defined as above, or a reactive derivative thereof, to give a compound of the general formula IIID or IVD in which $R^{16}$ denotes a group of the formula XII:

$$\text{—S—}R^4 \qquad \qquad XII$$

in which $R^4$ is defined as above.

The reaction of the sulphoxide with the thiol may be carried out as described in European Patent Publication No. EP 0 046 363A.

A sulphoxide compound of the general formula IIID or IVD in which $R^{16}$ denotes a sulphoxide group of the formula IX above may be prepared by S-oxidation of a compound of the general formula IIID or IVD, respectively, in which $R^{16}$ denotes a group of the formula $-S-R^{15}$. The S-oxidation may be effected using a mild oxidising agent, for example a perbenzoic acid, hydrogen peroxide, selenium dioxide or sodium metaperiodate. Perbenzoic acids, for example m-chloroperbenzoic acid, are preferred.

The present invention also provides a process for the preparation of a compound of the general formula I in which $R^3$ denotes a group of the formula $-SR^4$ (in which $R^4$ is defined as above), or a pharmaceutically acceptable salt or in vivo hydrolysable ester thereof, which comprises reacting a compound of the general formula XIII:

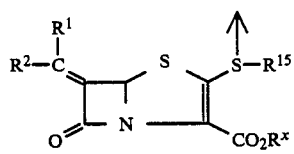

in which $R^1$, $R^2$, $R^{15}$ and $R^x$ are defined as above, with a thiol of the general formula XI above, or a reactive derivative thereof; and thereafter if necessary or desired:

(a) removing any carboxyl-blocking group $R^x$, and/or (b) converting the product into the free acid or into a pharmaceutically acceptable salt or in vivo hydrolysable ester.

The compounds of the general formulae IIIC and IVC are novel intermediates and also constitute subjects of the present invention. The compounds of the general formula IIID, in particular those in which $R^{16}$ denotes $R^3$ or a sulphoxide group of the formula IX, are also novel intermediates and form a further subject of the present invention. The compounds of the general formula IVD in which $R^{16}$ denotes a sulphoxide group of the formula IX are further novel intermediates and constitute a yet further subject of the present invention.

The compounds according to the invention have $\beta$-lactamase inhibitory and antibacterial properties, and are useful for the treatment of infections in animals, especially mammals, including humans, in particular in humans and domesticated (including farm) animals. The compounds may be used, for example, for the treatment of infections of, inter alia, the respiratory tract, the urinary tract, and soft tissues, especially in humans.

The compounds may be used for the treatment of infections caused by strains of, for example, *Staphylococcus aureus*, *Klebsiella aerogenes*, *Escherichia coli*, *Proteus* sp., and *Bacteroides fragilis*. It is generally advantageous to use a compound according to the invention in admixture or conjunction with a penicillin, cephalosporin or other $\beta$-lactam antibiotic and that can often result in a synergistic effect, because of the $\beta$-lactamase inhibitory properties of the compounds according to the invention. In such cases, the compound according to the invention and the other $\beta$-lactam antibiotic can be administered separately or in the form of a single composition containing both active ingredients as discussed in more detail below.

The compounds according to the invention are suitably provided in substantially pure form, for example at least 50% pure, advantageously at least 75% pure, preferably at least 95% pure, especially at least 98% pure, all percentages being calculated as weight/weight. An impure or less pure form of a compound according to the invention may, for example, be used in the preparation of a more pure form of the same compound or of a related compound (for example, a corresponding salt, ester or free acid) suitable for pharmaceutical use. Although the purity of any compound used as an intermediate may be less critical than that of a compound used as a final product, for example one used directly for pharmaceutical use (for example in a composition according to the invention as described below), nevertheless such an intermediate compound is advantageously provided in substantially pure form. It is generally advantageous to provide the compounds according to the invention in crystalline form.

The present invention provides a pharmaceutical composition comprising a compound according to the invention that is to say, a compound of the general formula I or a pharmaceutically acceptable salt or in vivo hydrolysable ester thereof, and a pharmaceutically acceptable carrier.

The present invention also provides a method of treating bacterial infections in animals, especially in humans and in domesticated mammals (including farm mammals), which comprises administering a compound or composition according to the invention to the animal. Such administration may advantageously be effected in conjunction with the prior, simultaneous or subsequent administration of a penicillin, cephalosporin or other $\beta$-lactam antibiotic.

The compositions of the invention may be in a form adapted for oral, topical or parenteral use and may be used for the treatment of infection in animals especially mammals, including humans, in particular in humans and domesticated animals (including farm animals).

The compositions of the invention may, for example, be made up in the form of tablets, capsules, creams, syrups, suspensions, solutions, reconstitutable powders, and sterile forms suitable for injection or infusion. Such compositions may contain conventional pharmaceutically acceptable materials, for example diluents, binders, colours, flavours, preservatives, and disintegrants, in accordance with conventional pharmaceutical practice in manner well understood by those skilled in the art of formulating antibiotics.

It can be particularly advantageous for the compounds according to the invention to be administered to a patient by injection or infusion. That method of administration has the advantage of rapidly resulting in high blood levels of the active ingredient compound being administered. Accordingly, in one preferred form of the composition according to the invention, a compound according to the invention is present in sterile form, including in sterile crystalline form. A further preferred form of the composition according to the invention, is one in which the composition is in injectable or infusable form.

One injectable or infusable form of the composition according to the invention is an injectable or infusable solution, which suitably comprises a solution of a compound according to the invention in a sterile pyrogen-free liquid, for example water or aqueous ethanol.

A further injectable or infusable form of the composition according to the invention is an injectable or infusable suspension, in which case the compound according to the invention is advantageously present in finely particulate form. The suspension may be an aqueous suspension in, for example, sterile water or sterile saline, which may additionally include a suspending agent, for example polyvinylpyrrolidone. Alternatively, the suspension may be an oily suspension in a pharmaceutically acceptable oil suspending agent, for example arachis oil.

A composition according to the invention may be in unit dosage form, for example unit dosage form for oral administration, topical administration, or parenteral administration (including administration by injection or infusion).

A composition according to the invention may comprise a compound according to the invention as the sole active ingredient or therapeutic agent, or it may also comprise one or more additional active ingredients or therapeutic agents, for example a penicillin, cephalosporin or other β-lactam antibiotic, or pro-drug thereof. A composition comprising a compound according to the invention and another active ingredient or therapeutic agent, especially a penicillin, cephalosporin or other β-lactam antibiotic, or pro-drug thereof, can show enhanced effectiveness, and in particular can show a synergistic effect.

Penicillins, cephalosporins and other β-lactam antibiotics suitable for co-administration with the compounds according to the invention—whether by separate administration or by inclusion in the compositions according to the invention—include both those known to show instability to or to be otherwise susceptible to β-lactamases and also those known to have a degree of resistance to β-lactamases.

Examples of penicillins suitable for co-administration with the compounds according to the invention include benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, sulbenicillin, piperacillin, and other known penicillins. The penicillins may be used in the form of pro-drugs thereof, for example as in vivo hydrolysable esters, for example the acetoxymethyl, pivaloyloxymethyl, α-ethoxycarbonyloxyethyl and phthalidyl esters of ampicillin, benzylpenicillin and amoxycillin; as aldehyde or ketone adducts of penicillins containing a 6-α-aminoacetamido side chain (for example hetacillin, metampicillin and analogous derivatives of amoxycillin); and as α-esters of carbenicillin and ticarcillin, for example the phenyl and indanyl α-esters.

Examples of cephalosporins that may be co-administered with the compounds according to the invention include, fatrizine, cephaloridine, cephalothin, cefazolin, cephalexin, cephacetrile, cephapirin, cephamandole nafate, cephradine, 4-hydroxycephalexin, cephaloglycin, cefoperazone, cefsulodin, ceftazidime, cefuroxime, cefmetazole, cefotaxime, ceftriaxone, and other known cephalosporins, all of which may be used in the form of pro-drugs thereof.

Examples of β-lactam antibiotics other than penicillins and cephalosporins that may be co-administered with the compounds according to the invention include aztreonam, latamoxef (Moxalactam - Trade Mark), and other known β-lactam antibiotics, all of which may be used in the form of pro-drugs thereof.

In the compositions according to the invention, the compound according to the invention and the penicillin, cephalosporin or other β-lactam antibiotic may be linked by means of an in vivo hydrolysable ester group, in the form of a mutual pro-drug.

Some penicillins and cephalosporins that may be included in the compositions according to the invention may not be suitable for oral administration, in which case the composition will be in a form suitable for parenteral or topical administration.

Particularly suitable penicillins for co-administration with the compounds according to the invention include ampicillin, amoxycillin, carbenicillin, piperacillin, azlocillin, mezlocillin, and ticarcillin. Such penicillins may be used in the form of their pharmaceutically acceptable salts, for example their sodium salts. Alternatively, ampicillin or amoxycillin may be used in the form of fine particles of the zwitterionic form (generally as ampicillin trihydrate or amoxycillin trihydrate) for use in an injectable or infusable suspension, for example, in the manner hereinbefore described in relation to the compounds according to the invention. Amoxycillin, for example in the form of its sodium salt or the trihydrate, is particularly preferred for use in synergistic compositions according to the invention.

Particularly suitable cephalosporins for co-administration with the compounds according to the invention include cephaloridine, cefoperazone and cefazolin, which may be used in the form of their pharmaceutically acceptable salts, for example their sodium salts.

A compound according to the invention may be administered to the patient in an antibacterially effective amount or, when a compound according to the invention is being used in conjunction with a penicillin, cephalosporin, or other β-lactam antibiotic, it may be used in a synergistically effective amount.

The compounds according to the invention may suitably be administered to the patient at a daily dosage of from 0.7 to 50 mg/kg of body weight. For an adult human (of approximately 70 kg body weight), from 50 to 3000 mg, preferably from 100 to 1000 mg, of a compound according to the invention may be administered daily, suitably in from 1 to 6, preferably from 2 to 4, separate doses. Higher or lower dosages may, however, be used in accordance with clinical practice.

When the compositions according to the invention are presented in unit dosage form, each unit dose may suitably comprise from 25 to 1000 mg, preferably from 50 to 500 mg, of a compound according to the invention. Each unit dose may, for example, be 62.5, 100, 125, 150, 200 or 250 mg of a compound according to the invention.

When the compounds according to the invention are co-administered with a penicillin, cephalosporin or other β-lactam antibiotic, the ratio of the amount of the compound according to the invention to the amount of the other β-lactam antibiotic may vary within a wide range. The said ratio may, for example, be from 100:1 to 1:100; more particularly, it may, for example, be from 2:1 to 1:30.

The amount of penicillin or cephalosporin or other β-lactam antibiotic in a synergistic composition according to the invention will normally be approximately similar to the amount in which it is conventionally used per se, for example from about 50 mg, advantageously from about 62.5 mg, to about 3000 mg per unit dose, more usually about 125, 250, 500 or 1000 mg per unit dose.

An example of a particularly suitable composition according to the invention is one comprising from 150 to 1000 mg, preferably from 200 to 700 mg, of amoxycillin or ampicillin or a pro-drug thereof, in admixture or conjunction with from 5 to 500 mg, preferably from 20 to 250 mg, of a compound according to the invention, per unit dose. In such a composition, the amoxycillin may suitably be in the form of its trihydrate or sodium salt; the ampicillin may suitably be in the form of ampicillin trihydrate, ampicillin anhydrate, sodium ampicillin, hetacillin, pivampicillin hydrochloride, bacampicillin hydrochloride or talampicillin hydrochloride; and the compound according to the invention may most suitably be in crystalline form. Such composition may be in a form suitable for oral or parenteral use, except when it comprises an in vivo hydrolysable ester of ampicillin or amoxycillin in which case the composition should not normally be intended for parenteral administration.

A further example of a particularly suitable composition according to the invention is one comprising from 200 to 2000 mg of carbenicillin or ticarcillin or a pro-drug thereof, in admixture or conjunction with from 5 to 500 mg, preferably from 25 to 250 mg, of a compound according to the invention, per unit dose. In such a composition, the carbenicillin or ticarcillin may most suitably be in the form of its di-sodium salt, and the compound according to the invention may most suitably be in crystaline form. When the composition contains the carbenicillin or ticarcillin in the form of a di-salt, it is most suitably presented in a form suitable for parenteral administration.

The following examples illustrate the invention. Unless otherwise stated, all temperatures are given in degrees Celsius and all percentages are calculated by weight. The term 'Biogel' used in the examples is a Trade Mark.

Preparation 1(a)

1-t-Butyldimethylsilyl-3-[hydroxy(5-isothiazolyl)methyl]-4-tritylthioazetidin-2-one A solution of n-butyl lithium (1.64M in hexane, 0.73 ml) was added to a solution of diisopropylamine (0.17 ml) in dry tetrahydrofuran (THF) (8 ml) at −30° C. under dry argon. After stirring at −30° C. for 10 minutes the mixture was cooled to −76° C. and treated with a solution of 1-t-butyldimethylsilyl-4-tritylthioazetidin-2-one (1) (459 mg) (Bristol-Myers Patent GB No. 2042515 A) in dry THF (4 ml). After a further 15 minutes at −76° C. the stirred mixture was treated with a solution of 5-formylisothiazole (135 mg) (M. P. L. Caton et. al., *J. Chem. Soc.*, 1964, 446) in dry THF (1 ml). After 20 minutes at −76° C. the stirred mixture was treated with saturated ammonium chloride solution (5 ml) and allowed to attain 0° C. The mixture was diluted with ethyl acetate (25 ml) and washed with brine (5 ml), dilute sodium bisulphite solution (5 ml) and brine (3×5 ml). The dried (MgSO$_4$) organic layer was evaporated and the residue chromatographed on silica gel eluting with ethyl acetate/hexane mixtures to give two fractions. The less polar fraction contained a 3:1 mixture of a trans (Isomer A) and a cis-isomer (Isomer B) of the title azetidinone (2) (112 mg), a solid, $\nu$max (CHCl$_3$) 3600–3100, 1745 cm$^{-1}$; δppm (CDCl$_3$) 0.91 and 0.99 (9H, each s, ratio 3:1), 1.60–2.10 (1H, broad signal, exch. D$_2$O), 3.35–3.56 (1.25H, m), 4.06 (0.75H, d, J3 Hz), 4.57 (0.75H, d, J2 Hz), 4.88 (0.25H, d, J5 Hz), 7.00–7.60 (16H, m), 8.29 (1H, d, J2 Hz), both Me$_3$Si signals were obscured by the TMS signal. The more polar fraction contained a trans-isomer (Isomer C) of the title azetidinone (2) (144 mg), a solid, mp 183°–184° C. (prisms ex ethyl acetate/hexane); $\nu$max (CHCl$_3$) 3600–3100, 1735 cm$^{-1}$; δppm (CDCl$_3$) 0.81 (9H, s), 2.70–3.10 (1H, broad signal, exch. D$_2$O), 3.70 (1H, dd, J7 and 2 Hz), 4.10 (1H, d, J2 Hz), 4.30–4.50br (1H, m, collapses to d, J7 Hz on exch. D$_2$O), 6.81br (1H, s), 7.20–7.50 (15H, m), 8.22 (1H, d, J2 Hz), both Me$_3$Si signals were obscured by the TMS signal. (Found: C, 67.1; H, 6.3; N, 4.9; S, 11.2. C$_{32}$H$_{36}$N$_2$O$_2$S$_2$Si requires C, 67.1; H, 6.3; N, 4.9; S, 11.2%).

Preparation 1(b)

(3RS, 4SR) 3-[Hydroxy(5-isothiazolyl)methyl]-4-tritylthioazetidin-2-one

The trans-azetidinone (2) (Isomer C) (86 mg) from Preparation 1(a) was dissolved in a mixture of methanol (1 ml) and dichloromethane (1 ml), cooled to −20° C., and treated with a solution of anhydrous potassium flouride (9 mg) in methanol (0.2 ml). After 1 hour at −20° C. the stirred mixture was allowed to attain room temperature during 20 minutes. The mixture was diluted with ethyl acetate (10 ml) and washed with brine (3×2 ml). The dried (MgSO$_4$) organic layer was evaporated and the residue chromatographed on silica gel eluting with ethyl acetate/hexane mixtures to give the title alcohol (3) (67 mg) as a solid, mp 197°–198° C. (needles ex. ethyl acetate/hexane); $\nu$max (CHCl$_3$) 3600–3100, 1760 cm$^{-1}$; δppm (CDCl$_3$) 3.61 (1H, dd, J2.8 and 2.8 Hz), 3.89br (1H, d, J4.4 Hz, exch. D$_2$O), 4.22 (1H, s), 4.47 (1H, d, J2.8 Hz), 5.55 br (1H, broad signal, collapses to d, J2.8 Hz on exch. D$_2$O), 7.16–7.37 (16H, m), 8.60 (1H, d, J1.7 Hz). (Found: C, 68.3; H, 4.9; N, 6.2; S, 14.1. C$_{26}$H$_{22}$N$_2$O$_2$S$_2$ requires C, 68.1; H, 4.8; N, 6.1; S, 14.0%).

Preparation 1(c)

(3RS, 4SR) 3-[Acetoxy(5-isothiazolyl)methyl]-4-tritylthioazetidin-2-one

The alcohol (3) (56 mg) from Preparation 1(b) was dissolved in dry dichloromethane (2 ml), cooled in an ice bath, and treated with triethylamine (15 mg), 4-dimethylaminopyridine (1.5 mg) and acetic anhydride (15 mg). The mixture was allowed to attain room temperature and was stirred for a further 30 minutes. The mixture was diluted with ethyl acetate (10 ml) and washed with 5% citric acid (1 ml), brine (1 ml), saturated NaHCO$_3$ (1 ml) and brine (1 ml). The dried (MgSO$_4$) organic layer was evaporated and the residue chromatographed on silica gel eluting with ethyl acetate/hexane mixture to give the title acetate (4) (40 mg) as a solid, mp 167°–168° C. (rhomboids ex ethyl acetate/hexane); $\nu$max (CHCl$_3$) 3380, 1775 cm$^{-1}$; $\delta$ppm (CDCl$_3$) 2.10 (3H, s), 3.66 (1H, dd, J5 and 3 Hz, with further small coupling), 4.41 (d, J3 Hz) and 4.15–4.65 (broad signal) together 2H, 5.54 (1H, d, J5 Hz), 7.20–7.60 (16H, m), 8.51 (1H, d, J2 Hz). (Found: C, 67.0; H, 4.8; N, 5.6; S, 12.4: C$_{28}$H$_{24}$N$_2$O$_3$S requires C, 67.2; H, 4.8; N, 5.6; S, 12.8%).

Preparation 1(d)

(3RS, 4SR) 3-[Acetoxy (5-isothiazolyl)methyl]-1-(1-p-nitrobenzyloxycarbonyl-1-triphenylphosphoranylidenemethyl)-4-tritylthicazetidin-2-one The azetidinone (4) (4.63 g) from Preparation 1(c) and p-nitrobenzyl glyoxylate monohydrate (2.32 g) were heated in refluxing benzene (100 ml) with provision for azeotropic removal of water (Dean and Stark apparatus containing molecular sieves 4A) fpr 1 hour. The mixture was cooled to room temperature and treated with triethylamine (94 mg). After 30 minutes at room temperature the mixture was evaporated to give a crude hydroxyester (5) as an amorphous solid, $\nu$max (CHCl$_3$) 3600–3100, 1770, 1750 cm$^{-1}$. A solution of the crude hydroxyester (5) in dry THF (100 ml) was cooled to $-10°$ C. and treated with 2,6-lutidine (1.62 ml) and thionyl chloride (1.01 ml). After stirring at $-10°$ C. for 10 minutes the mixture was filtered and evaporated. The residue was re-evaporated from dry toluene (2×10 ml) to give a crude chloroester (6) as an amorphous solid, $\nu$max 1780 br. cm$^{-1}$. The crude chloroester (6) and triphenylphosphine (9.7 g) were stirred in dry dioxan (20 ml) for 30 minutes. The resulting solution was evaporated to approximately half volume and treated with 2,6-lutidine (1.29 ml). The mixture was stirred at room temperature for 3½ days and then at 40° C. for 24 hours. The mixture was diluted with ethyl acetate (300 ml) and washed with 5% citric acid (25 ml), brine (25 ml), saturated NaHCO$_3$ (25 ml), and brine (3×25 ml). The dried (MgSO$_4$) organic layer was evaporated and the residue chromatographed on silica gel eluting with ethyl acetate/hexane mixtures to give the title phosphorane (7) (7.61 g) as an amorphous solid, $\nu$max (CHCl$_3$) 1755, 1615, 1605 sh. cm$^{-1}$.

Preparation 1(e)

(3RS, 4SR) Silver 3-[Acetoxy(5-isothiazolyl)methyl]-1-(1-p-nitrobenzyloxycarbonyl-1-triphenylphosphoranylidenemethyl) azetidin-2-one-4-thiolate Silver nitrate (18.2 ml of a 0.15M solution in methanol) was added to a stirred mixture of the phosphorane (7) (2.0 g) from Preparation 1(d) and pyridine (0.22 ml) in methanol (20 ml) and dichloromethane (20 ml) at room temperature. After 30 mins at room temperature the stirred mixture was cooled in an ice bath for 10 minutes and filtered. Theresidue was washed with cold methanol (5 ml) and dry ether (2×5 ml) and dried under vacuum to give the title silver thiolate (8) (1.17 g) as an off-white amorphous solid, $\nu$max (Nujol) 1750, 1600 cm$^{-1}$ The combined filtrates were evaporated to low volume, filtered, and the residue washed with methanol (2 ml) and dry ether (2×2ml) and, dried under vacuum to give the title silver thiolate (8) (0.28 g) as an off white amorphous solid.

Preparation 1(f)

(5RS, 6SR) p-Nitrobenzyl 6[-Acetoxy(5-isothiazolyl)methyl]penem-3-carboxylate

A stirred, ice bath cooled, suspension of the silver thiolate (8) (818 mg) from Preparation 1(e) in dry dichloromethane (10 ml) was treated with acetic-formic anhydride (0.80 ml), 4-dimethylaminopyridine (122 mg) and triethylamine hydrochloride (1.38 g). The ice bath was removed and the mixture was stirred for a further 10 minutes. The mixture was diluted with ethyl acetate (10 ml) and filtered through Kieselguhr the residue being washed with ethyl acetate (3×10 ml). The combined filtrates were washed with 5% citric acid (5 ml , brine (5 ml), saturated NaHCO$_3$ solution (5 ml), and brine (3×5 ml). The dried (MgSO$_4$) organic layer was heated at 50° C. under argon for 40 minutes, evaporated and the residue chromatographed on silica gel eluting with ethyl acetate/hexane mixtures to give the title penem (9) (391 mg) as a solid, mp 154°–156° C. (plates ex ethyl acetate/hexane); $\nu$max (CHCl$_3$/EtOH) 307 (Em 9070) and 251 nm (16126); $\nu$max (CHCl ) 1800, 1750, 1720 cm$^{-1}$; $\delta$ppm (CDCl$_3$) 2.17 (3H, s), 4.35 (1H, ddd, J5.4, 1.9 and 1.1 Hz), 5.29 and 5.42 (2H, ABq, J13.5 Hz), 5.85 (1H, d, J1.9 Hz), 6.60 (1H, slightly broadened d, J5.4 Hz), 7.25 (1H, dd, J1.8 and 0.7 Hz), 7.33 (1H, d, J1.1 Hz), 7.58 (2H, d, J8.8 Hz), 8.24 (2H, d., J8.8 Hz), 8.46 (1H, d, J1.8 Hz). (Found: C, 49.5; H, 3.4; N, 9.0; S, 13.9; M-60]$^+$, 401.0135. C$_{19}$H$_{15}$N$_3$O$_7$S$_2$ requires C, 49.4; H, 3.3; N, 9.1; S, 13.9% M - CH$_3$CO$_2$H, 401.0141).

EXAMPLE 1(a)

(5RS) p-Nitrobenzyl 6-(5-Isothiazolylmethylene)penem-3-carboxylate

A solution of 1,8-diazabicyclo[5.4.0]undec -7-ene (49 mg) in dry dichloromethane (0.5 ml) was added, dropwise over 0.5 minute, to a stirred solution of the penem (9) (100 mg) from Preparation 1(f) in dry dichloromethane (3 ml) at $-40°$ C. After 10 minutes at $-40°$ C. the stirred mixture was diluted with dichloromethane (10 ml) and washed with 5% citric acid (1 ml), brine (1 ml), saturated NaHCO$_3$ solution (1 ml), and brine (3×1 ml). The dried (MgSO$_4$) organic layer was evaporated and the residue chromatographed on silica gel eluting with ethyl acetate/dichloromethane mixtures to give the title penem (10) (70 mg), a 4:1 mixture of (Z) and (E)-isomers, as a yellow solid, $\delta$ppm (CDCl$_3$) 5.31 and 5.46 (2H, ABq, J13.6 Hz), 6.47 (1H, d, J1.1 Hz), 6.88 (0.2H, s), 7.34 (0.8H, d, J1.9 Hz), 7.40 (0.8H, s), 7.42 (0.8H, s), 7.45 (0.2H, s), 7.62 (2H, d, J8.7 Hz), 7.82 (0.2H, m), 8.25 (2H, d, J8.7 Hz), 8.52 (0.2H, d, J2.1 Hz), 8.58 (0.8H, d, J1.9 Hz). The mixture was recrystallised twice from chloroform/hexane to give the (Z)-isomer as a microcrystalline solid (38 mg), mp 169°–172° C.; $\lambda$max (EtOH/CHCl$_3$) 288 nm (Em 28492); max (CHCl$_3$) 1790, 1720, 1675 cm$^{-1}$; $\delta$ppm (CDCl$_3$) 5.31 and 5.46 (2H, ABq, J13.5 Hz), 6.47 (1H, d, J1.1 Hz), 7.34 (1H, d, J1.6 Hz), 7.40 (1H, s), 7.42 (1H, slightly broadened s), 7.62 (2H, d, J8.7 Hz), 8.25 (2H, d, J8.7 Hz), 8.58 (1H, d, J1.6 Hz). (Found: C, 50.7; H, 2.6; N, 10.1; S, 16.2. C$_{17}$H$_{11}$N$_3$O$_5$S$_2$ requires C, 50.9; H, 2.8; N, 10.5; S, 16.0%).

EXAMPLE 1(b)

(5RS) Sodium (Z)-6-(5-Isothiazolylmethylene)penem-3-carboxylate

The penem ester (10) (Z-isomer) (90 mg) from Example 1(a) was dissolved in a mixture of dioxan (64 ml) and water (16 ml) and hydrogenated over 5% palladium/charcoal catalyst (135 mg) at S.T.P. for 1 hour. A 1% sodium bicarbonate solution (1.88 ml) was added and the mixture filtered through Kieselguhr, the residue being washed with a little aqueous dioxan. The combined filtrates were evaporated and the residue chromatographed on Biogel P2 eluting with water. The appropriate fractions were freeze dried to give the title sodium salt (11) (34 mg) as an orange/brown amorphous solid, $\lambda$max ($H_2O$) 288 nm (Em 22924); $\nu$max (KBr) 3850–2000, 1760, 1670 sh, 1600, 1555, 1505 sh. cm$^{-1}$; $\delta$ppm ($D_2O$) 6.60 (1H, d, J0.9 Hz), 7.08 (1H, s), 7.49 (1H, d, J1.9 Hz), 7.53br(1H, s), 8.57 (1H, d, J1.9 Hz).

Preparation 2(a)

1-t-Butyldimethylsilyl-3-[hydroxy(1-methylpyrazol-4-yl)methyl]-4-tritylthioazetidin-2-one A solution of n-butyl lithium (1.06M. in hexane, 1.13 ml) was added to a solution of diisopropylamine (0.17 ml) in dry THF (8 ml) at $-30°$ C. under dry argon. After stirring at $-30°$ C. for 10 minutes the mixture was cooled to $-76°$ C. and treated with a solution of 1-t-butyldimethylsilyl-4-tritylthioazetidin-2-one (1) (459 mg) in dr THF (4 ml). After a further 15 minutes at $-76°$ C. the stirred mixture was treated with a solution of 4-formyl-1-methylpyrazole (132 mg) (I. L. Finar and G. H. Lord, J. Chem. Soc. 1957, 3314) in dry THF (1 ml). After 20 minutes at $-76°$ C. the stirred mixture was treated with saturated ammonium chloride solution (5 ml) and worked up as for Preparation 1(a) to give two fractions. The less polar fraction contained a trans-isomer (Isomer A) of the title azetidinone (12) (165 mg), an amorphous solid, $\nu$max (CHCl$_3$) 3600–3100, 1735 cm$^{-1}$; $\delta$ppm (CDCl$_3$) 0.92 (9H, s), 1.1–1.8 (1H, br. signal, exch. $D_2O$), 3.32 (1H, dd, J2 and 2 Hz), 3.50 (1H, d, J2 Hz), 3.76 (3H, s), 4.46 (1H, d, J2 Hz), 7.10–7.60 (17H, m), the Me$_2$Si signals were obscured by the TMS signal. [Found (diethylamine chemical ionisation): MH$^+$, 570 and M+Et$_2$NH]$^+$, 643]. The more polar fraction contained the other trans-isomer (Isomer B) of the title azetidinone (12) (185 mg), an amorphous solid, $\nu$max (CHCl$_3$) 3600–3100, 1735 cm$^{-1}$; $\delta$ppm (CDCl$_3$) 0.80 (9H, s), 1.7–2.5 (1H, br. signal, exch. $D_2O$), 3.59 (1H, dd, J6 and 2 Hz), 3.70 (3H, s), 3.87 (2H, 2d, J2 Hz and J6 Hz), 6.91 (1H, s), 7.10–7.50 (16H, m), the Me$_2$Si signals were obscured by the TMS signal. [Found (diethylamine chemical ionisation): MH$^+$, 570].

Preparation 2(b)

(3RS, 4SR) 3-[Hydroxy(1-methylpyrazol-4-yl)methyl]-4-tritylthioazetidin-2-one A solution of anhydrous potassium fluoride (14 mg) in methanol (0.5 ml) was added to a stirred solution of the trans-azetidinone (12) (Isomer B) (126 mg) in methanol (1 ml) at $-20°$ C. After 30 minutes at $-20°$ C. the mixture was allowed to attain room temperature and stirred for a further 1 hour. The mixture was diluted with ethyl acetate (10 ml) and was washed with brine (3×1 ml). The dried (MgSO$_4$) organic layer was evaporated and the residue triturated with ether to give the title alcohol (13) (80 mg) as a solid, mp 159°–162° C. (plates ex ethylacetate/hexane), $\nu$max (CHCl$_3$) 600–3100, 1750 cm$^{-1}$; $\delta$ppm (CDCl$_3$) 2.3–2.9 (1H, br. signal, exch. $D_2O$), 3.43 (1H, dd, J5 and 3 Hz), 3.90 (3H, s), 4.25–4.50 (or. signal) and 4.44 (d, J3 Hz) (together 2H, the broad signal exch. $D_2O$), 5.08 (1H, d, J5 Hz), 7.1–7.5 (17H, m). (Found: C, 71.1; H, 5.7; N, 9.2; S, 6.6. $C_{27}H_{25}N_3O_2S$ requires C, 71.2; H, 5.5; N, 9.2; S, 7.0%).

Preparation 2(c)

(3RS, 4SR) 3-[Acetoxy (1-methylpyrazol-4-yl)methyl]-4-tritylthioazetidin-2-one The alcohol (13) (46 mg) from Preparation 2(b) was dissolved in dry dichloromethane (2 ml), cooled in an ice-bath, and treated with triethylamine (12 mg), 4-dimethylaminopyridine (1.2 mg), and acetic anhydride (12 mg). The ice-bath was removed and the mixture was stirred for 1 hour. The mixture was worked up as for Preparation 1(c) to give the title acetate (14) (35 mg) as a solid, mp 179°–180° C. (rhomboids ex ethyl acetate/hexane); $\nu$max (CHCl$_3$) 3380, 1770 cm$^{-1}$; $\delta$ppm (CDCl$_3$) 2.06 (3H, s), 3.50–3.70 (1H, m), 3.85 (3H s), 4.36 (1H, d, J3 Hz), 4.51 (1H, brs), 6.10 (1H, d, J6 Hz), 7.20–7.70 (17H, m). (Found: C, 70.0; H, 5.5 N, 8.3. $C_{29}H_{27}N_3O_3S$ requires C, 70.0; H, 5.5; N, 8.4%).

Preparation 2(d)

(3RS, 4SR) 3-[Acetoxy (1-methylpyrazol-4-yl)methyl]-1-(1-p-nitrobenzyloxycarbonyl-1-triphenylphosphoranylidenemethyl)-4-tritylthioacetidin-2-one The azetidinone (14) (200 mg) from Preparation 2(c) was converted to the hydroxyester (15), $\nu$max (CHCl$_3$) 3600–3100, 1770, 1755 sh. cm$^{-1}$; the chloroester (16), $\nu$max (CHCl$_3$) 1775 cm$^{-1}$; and finally the title phosphorane (17) (256 mg), $\nu$max (CHCl$_3$) 1745, 1605 cm$^{-1}$; using the methods described in Preparation 1(d).

Preparation 2(e)

(3RS, 4SR) Silver 3-[Acetoxy (1-methylpyrazol-4-yl)methyl]-1-(1-p-nitrobenzyloxycarbonyl-1-triphenylphosphoranylidenemethyl)azetidin-2-one-4-thiolate The phosphorane (17) (250 mg) from Preparation 2(d) was treated with silver nitrate/pyridine as for Preparation 1(e) to give the title silver salt (18) (201 mg) as an amorphous solid, $\nu$max (Nujol) 1740, 1600 cm$^{-1}$.

Preparation 2(f)

(5RS, 6SR) p-Nitrobenzyl 6-[Acetoxy (1-methylpyrazol-4-yl)methyl]penem-3-carboxylate The silver salt (18) (1.40 g) from Preparation 2(e) was treated as for Preparatinn 1(f) to give the title penem (19) (675 mg) as a solid, m.p. 140°–141° C. (fine needles ex ethylacetate/hexane); $\nu$max (EtOH) 262 (Em 13069 and 315 nm (8588); $\nu$max (CHCl$_3$) 1795, 1720 cm$^{-1}$; $\delta$ppm (CDCl$_3$) 2.05 (3H, s), 3.84 (3H, s), 4.29 (1H, ddd, J7, 2 and approximately 1Hz), 5.21 and 5.41 (2H, ABq, J14 Hz), 5.73 (1H, d, J2 Hz), 6.14 (1H, d, J7 Hz), 7.30–7.36 (1H, m), 7.41–7.49 (2H, m), 7.54 (2H, d, J9 Hz), 8.19 (2H, d, J9 Hz). (Found: C, 52.2; H, 4.0; N, 12.1; S, 6.7. $C_{20}N_{18}N_4O_7S$ requires C, 52.4; H, 4.0; n, 12.2; S, 7.0%).

EXAMPLE 2(a)

(5RS) p-Nitrobenzyl6-[(1-Methylpyrazol-4-yl)methylene]-penem-3-carboxylate

Treatment of the penem (19) (675 mg) from Preparation 2(f) with 1,8-diazabicyclo[5.4.0]undec-7-ene as for Example 1(a) gave two products. The less polar product, the (E)-isomer of the title penem (20) (45 mg) was obtained as a pale yellow solid, mp 173°–175° C. (needles ex chloroform/hexane); $\nu$max (EtOH) 307 nm (Em 26375); $\nu$max (CHCl$_3$) 1765, 1715, 1665 cm$^{-1}$; $\delta$ppm (CDCl$_3$) 3.96 (3H, s), 5.31 and 5.45 (2H, ABq, J13.7 Hz), 6.43 (1H, s), 6.56 (1H, s), 7.41 (1H, s), 7.62 (2H, d, J8.7 Hz), 7.79 (1H, s), 8.25 (2H, d, J8.7 Hz), 8.34 (1H, s). (Found: C, 54.5; H, 3.3; N, 13.8. $C_{18}H_{14}N_4O_5S$ requires C, 54.3; H, 3.5; N, 14.1%). The more polar product, the (Z)-isomer of the title penem (20) (406 mg) was obtained as a yellow solid, m.p. 190°–192° C. (fine needles ex choroform/hexane); ;max (EtOH) 298nm (Em 34024); $\nu$max (CHCl$_3$) 1780, 1720, 1680 cm$^{-1}$; $\delta$ppm (CDCl$_3$) 3.96 (3H, s), 5.29 and 5.46 (2H, ABq, J13.6 Hz), 6.48 (1H, d, J0.7 Hz), 7.10 (1H, slightly br. s), 7.34 (1H, s), 7.50–7.51 (2H, each s), 7.62 (2H, d, J8.7 Hz), 8.24 (2H, d, J8.7 Hz). (Found: C, 54.2; H, 3.6; N, 13.9; S, 8.1. $C_{18}H_{14}N_4O_5S$ requires C, 54.3; H, 3.5; N, 14.1; S, 8.0%).

EXAMPLE 2(b)

(5RS) Sodium (E)-6-[(1-Methylpyrazol-4-yl)methylene]penem-3-carboxylate

The (E)-penem ester (20) (36 mg) from example 2(a) was hydrogenated as for Example 1(b) to give the title sodium salt (21) (8.5 mg) as a yellow amorphous solid $\nu$max (H$_2$O) 300 nm (Em 17375); $\delta$ppm D$_2$O) 3.88 (3H, s), 6.42 (1H, s), 6.73 (1H, s), 7.08 (1H, s), 7.96 (1H, s), 8.19 (1H, s).

EXAMPLE 2(c)

(5RS) Sodium (Z)-6-[(1-Methylpyrazol-4-yl)methylene]penem-3-carboxylate

The (Z)-penem ester (20) (200 mg) from Example 2(a) was hydrogenated as for Example 1(b) to give the title sodium salt (22) (58 mg) as a yellow amorphous solid, $\nu$max (H$_2$O) 293 nm (Em 23152); $\nu$max (KBr) 3700–2800, 1756, 1676, 1602, 1551 cm$^{-1}$; $\delta$ppm (D$_2$O) 3.92 (3H, s), 6.59 (1H, s), 7.05 (1H, s), 7.18 (1H, s), 7.69 (1H, s), 7.86 (1H, s).

Preparation3(a)

(3RS,4SR) 1-t-Butyldimethylsilyl-3-(2-methylthiazol-4-yl-carbonyl)-4-trityl-thioazetidin-2-one Di-isopropylamine (2.9 mls) was dissolved in dry THF (75 mls at −70° C. under argon.n-Butyl-lithium in n-hexane (1.4M, 15.5 mls was added dropwise with stirring and after 20 minutes at −70° C. a solution of azetidinone (1) (8.25 g) in THF (25 mls) was also added.

The resulting pink solution was kept at −70° C. for 30 minutes and then a solution of 2-methylthiazole-4-carboxylic acid ethyl ester (3.4 g) in THF (7 mls) was added in one portion.

After 5 minutes the tlc of a small sample showed no starting material in the reaction mixture. After 20 minutes the solution was diluted with saturated aqueous ammonium chloride and with brine. Extraction with ethyl acetate (200 ml×2), washing of the extracts with brine, drying (MgSO$_4$) and evaporation gave a gum.

Purification by silica gel chromatography, eluting with mixtures of ethyl acetate and n-hexane gave the title compound (23) as a buff coloured solid, 7.05 g; $\nu$max (CHCl$_3$) 1750, 1680 cm$^{-1}$; $\delta$(CDCl$_3$) 0.95 (9H, s), 2.69 (3H, s); 4.59 (1H, d, J2 Hz); 4.92 (1H, d, J2 Hz); 6.9–7.5 (15H, m); 7.76 (1H, s), the Me$_2$Si signals were obscured by TMS.

A sample crystallized from ethyl acetate-n-hexane had m.p.=195°–201° C.

Preparation 3(b)

(3RS,4SR) 1-t-Butyldimethylsilyl-3-[hydroxy(2-methyl-4thiazolyl)methyl]-4-tritylthio-azetidin-2-one The ketone (23) from Preparation3(a) (6.85 g) was dissolved in dioxane (100 ml) and pH 7 phosphate buffer (10 ml) added. Sodium borohydride (490 mg) was added in portions with stirring at ambient temperature. After 30 minutes tlc showed no change.

More sodium borohydride (960 mg) was added in portions and the stirring continued for 2 hours; tlc showed no starting material.

The solution was diluted with brine (ca. 100 ml) and extracted with ethyl acetate (200 mls, 100 mls). The combined extracts were washed with brine, dried (MgSO$_4$) and evaporated to a gum.

Purification by column chromatography on silica eluting with ethyl acetate-n-hexane (1:2) gave two isomeric alcohols (24): isomer I (25%), Rf 0.20; m.p. 162°–163° C.; $\nu$max (CHCl$_3$) 1730cm$^1$; $\delta$(CDCl$_3$) 0.80 (9H, s); 2.55 (1H, d, J6 Hz, exch. D$_2$O); 2.57 (3H, s); 3.54 (1H, dd, J 2.5, 1.8 Hz); 3.90 (1H, ddd, J 6, 2.5 ca. 1Hz) collapses to dd with D$_2$O; 4.49 (1H, d, J 1.8 Hz); 6.94 (1H, brs,J ca 1 Hz); 7.1–7.55 (ca. 15H, m), the Me$_2$Si signal was obscured by TMS. isomer II (65%), Rf 0.15; $\nu$max (CHCl$_3$) 1735 cm$^{-1}$; $\delta$(CDCl$_3$) 0.78 (9H, s); 2.53 (3H, s); 2.75 (1H, d, J 9 Hz, exch. D$_2$O); 3.68 (1H, dd, J 6, 1.8 Hz); 4.13 (1H, dd, J 9, 6 Hz) collapse to d with D$_2$O; 4.40 (1H, d, J 1.8 Hz); 6.69 (1H, s); 7.1–7.5 (15H, m), the Me$_2$Si signal was obscured by TMS.

Preparation 3(c)

(3RS, 4SR) 3[Hydroxy(2-methyl-4-thiazolyl)methyl]-4-tritylthioazetidin-2-one The azetidinone-alcohol (24) (isomer II), described in Preparation 3(b) (4.25 g) was dissolved in CH$_2$Cl$_2$ (10 ml) and methanol (35 ml). The solution was cooled to −10° C. and a solution of potassium fluoride (538 mg) in methanol (20 ml) was added dropwise with stirring.

After 1 hour at −10° C. the solution was diluted with brine and extracted with ethyl acetate (100 ml×2). Washing of the extract with brine, drying (MgSO$_4$) and evaporation gave a white solid. Trituration with a small volume of ethyl acetate gave the title azetidinone (25) (2.84 g) white crystals, m.p. 227°–229° C. decomp.

Evaporation of the mother liquors from the crystallization and chromatography of the residue gave a further 180 mg of product (25); $\nu$max (CHCl$_3$) 3380 br, 1755 cm$^{-1}$; $\delta$(CDCl$_3$) 2.61 (3H, s); 3.56 (1H, dd, J 3, 2 Hz); 4.21 (1H, d); 4.8–4.95 (1H, br, m); 5.80 (1H, d, J 5 Hz) exch. D$_2$O; 6.83 (1H, br, s) exch. D$_2$O; 7.0–7.4 (ca. 16H, m).

Preparation 3(d)

(3RS, 4SR) 3-[Acetoxy(2-methyl-4-thiazolyl)methyl]-4-tritylthioazetidin-2-one

The azetidinone (25) from Preparation 3(c) was partially dissolved in dry dichloromethane (40 ml) and 4-dimethylaminopyridine (805 mg) was added. The mixture was cooled in an ice-bath and a solution of acetic anhydride (0.67 ml) in dichloromethane (5 ml) was added dropwise with stirring. The cooling bath was removed.

After 30 minutes the clear solution was washed with 1NHCl, with aq. $NaHCO_3$ and with brine. Drying ($MgSO_4$) and evaporation gave a crude product which was purified by silica gel chromatography eluting with ethyl acetate-n-hexane (1:1).

The title acetate (26) was obtained in quantitative yield, m.p. 157°–158° (ex. ethyl acetate-n-hexane); $\nu$max ($CHCl_3$) 3400, 1765 cm$^{-1}$; $\delta$($CDCl_3$) 2.07 (3H, s); 2.71 (3H, s); 3.80 (1H, ddd, J 6, 2,1 Hz); 4.1 (ca 1H, brs, exch. $D_2O$); 4.53 (1H, d, J 2 Hz); 6.18 (1H, d, J 6 Hz); 7.01 (1H, s); 7.05–7.50 (15H, m).

Preparation 3(e)

(3RS, 4SR) 3-[Acetoxy(2-methyl-4-thiazolyl)methyl]-1-(1-p-nitrobenzyloxycarbonyl-1-triphenylphosphoranylidenemethyl)-4-tritylthioazetidin-2-one The azetidinone (26) (2.73 g) from Preparation 3(d) was converted to the title phosphorane (27) using the same method as that described in Preparation 1(d). The conversion of the intermediate chloride to phosphorane (27) was almost complete after reaction at 40° C. for about 15 hours.

Phosphorane (27) was obtained as a yellow foam (3.7 g); $\nu$max ($CHCl_3$) 1740–1750, 1600–1620 cm$^{-1}$.

Preparation 3(f)

(3RS, 4SR) Silver 3-[Acetoxy(2-methyl-4-thiazolyl)methyl]-1-(1-p-nitrobenzyloxycarbonyl-1-triphenylphosphoranylidenemethyl)-azetidin-2-one-4-thiolate Using the procedure described in Preparation 1(e) the S-trit phosphorane (27) from Preparation 3(e) was converted to the corresponding silver thiolate (28) in 79% yield.

Preparation 3(g)

(5RS, 6SR) p-Nitrobenzyl 6[Acetoxy(2-methyl-4-thiazolyl)methyl]-penem-3-carboxylate The silver thiolate (28) (1.1 g) from Preparation 3(f) was dissolved in dry dichloromethane (25 ml) and cooled to 0°–5° C. 4-Dimethylaminopyridine (180 mg) was added followed by triethylamine hydrochloride (900 mg) and acetic-formic anhydride (1.05 ml . The mixture was stirred at 0 to 5° C. for 30 minutes and the resulting grey precipitate was filtered off and washed well with ethyl acetate.

The filtrate was washed with 1N HCl, with aq. $NaHCO_3$ and with brine. The organic solution was dried ($MgSO_4$) and diluted to ca. 200 ml by addition of more ethyl acetate and heated at 40° C. under argon. After 1 hour the solution was evaporated to dryness giving a gum. Purification by column chromatography gave the title penem acetate (29) in 52% yield. When crystallized from ethyl acetate-n-hexane (29) had m.p. 143°–145° C.; $\nu$max (EtOH) 317 (8,400), 261 nm 13,000); $\nu$max ($CHCl_3$) 1790, 1730 sh, 1720 cm$^{-1}$; $\delta$($CDCl_3$) 2.08 (3H, s); 2.64 (3H, s); 4.42 (1H, ddd, J4,2,1 Hz); 5.20 (1H, d, J13 Hz); 5.40 (1H, d, J13 Hz); 6.09 (1H, d, J2 Hz); 6.20 (1H, d, J4 Hz); 7.18 (1H, s); 7.25 (1H, d, J1Hz); 7.5–7.6 and 8.12–8.22 (total 4H, m).

EXAMPLE 3(a)

(5RS) p-Nitrobenzyl 6[(2-Methyl-4-thiazolyl)methylene]penem-3-carboxylate

The penem acetate (29) (570 mg) prepared as described in Preparation 3(g) was dissolved in dry dichloromethane (10 ml) at −40° C. under argon. 1,8-Diazabicyclo[5.4.0]undec-7-ene (241 mg) dissolved in dichloromethane (2 ml) was added dropwise with stirring; the solution darkened slightly.

T.l.c. showed no starting material to be present and after 20 minutes the solution was diluted with 1 NHCl and with a small volume of dichloromethane. Further washing of the organic phase with aq. $NaHCO_3$ and with brine followed by drying ($MgSO_4$) and evaporation gave a yellow solid.

Chromatography on silica, eluting with 5% ethyl acetate-dichloromethane gave two isomers (30): isomer I, Z, Rf 0.5, 458 mg; $\lambda$max (EtOH) 299 nm (Em 23,100); $\nu$max ($CHCl_3$) 1775, 1710 1675 w. cm$^{-1}$; $\delta$($CDCl_3$) 2.73 3H, s ; 5.28 (1H, d, J13.6 Hz); 5.46 (1H, d, J 13.6 Hz), 6.64 (1H, d, J1.1 Hz); 7.00 (1H, d, J1.1 Hz); 7.37 (1H, s) 7.40 (1H, s); 7.61 and 7.65 (2H, arom.); 8.22 and 8.26 (2H, arom.). Isomer II, E, Rf 0.2, 12 mg; $\nu$max (EtoH) 260 nm(Em 13,900); $\nu$max ($CHCl_3$) 1760, 1720, 1670 w cm$^{-1}$; $\delta$($CDCl_3$) 2.73 (3H, s); 5.30 (1H, d, J 13.5 Hz); 5.47 (1H, d, J 13.5 Hz); 6.46 (1H, s); 6.87 (1H, s); 7.45 (1H, s); 7.60–7.64 (2H, m, arom.); 8.2–8.3 (2H, m, arom.).

EXAMPLE 3(b)

(5RS) Sodium (Z)-6-[(2-Methyl-4-thiazolyl)methylene]penem-3-carboxylate

The Z-penem ester (30) (418 mg) from Example 3(a) was hydrogenated at 1 atmosphere and room temperature in 20% water-dioxan (40 ml) containing 5% Pd/C (505 mg). After 45 minutes tlc showed no ester and a solution of sodium hydrogencarbonate (1 equivalent in water was added. Filtration and evaporation gave a yellow gum which was purified by passing through a column of Biogel P2 eluting with water.

The title compound (31) was obtained as a yellow, freeze dried solid (27%), $\nu$max ($H_2O$) 295 nm (Em 23,300); $\nu$max (KBr) 1752, 1676w, 1601 cm$^{-1}$; $\delta$($D_2O$) 2.71 (3H, s); 6.65 (1H, s); 7.02 (1H, s); 7.13 (1H, s); 7.69 (1H, s).

Preparation 4(a)

(3RS,4SR) 1-t-Butyldimethylsilyl-3-(isoxazol-3-ylcarbonyl)-4-tritylthioazetidin-2-one A solution of diisopropylamine (0.18 ml, 1.24 mmol) in dry THF (8 ml) under argon at −30° C. was treated dropwise with a solution of n-butyl lithium (1.66M, 0.75 ml, 1.24 mmol) in hexane. After 15 minutes the reaction mixture was cooled to −70° C. and treated dropwise with a solution of the azetidinone (1) (459 mg, 1 mmol)

in THF (8 ml). After a further 15 minutes the resulting pink solution was treated with a solution of 3-carboethoxyisoxazole (175 mg, 1.24 mmol) (R. G. Micetich, Can. J. Chem. 1970, 48, 467) in THF (1 ml). After 10 minutes the reaction mixture was quenched with saturated ammonium chloride solution and worked-up as in Preparation 3(a) to give the title azetidinone (32), 426 mg, 77%. mp 152°-154° C. (plates ex hexane), $\nu$max (CH$_2$Cl$_2$) 1750, 1695 cm$^{-1}$; $\delta$(CDCl$_3$) (excluding Me$_2$-Si-signals which were obscured by TMS) 0.98 (9H, s), 4.69 (1H, d, J2.0 Hz), 4.96 (1H, d, J2.0 Hz), 6.53 (1H, d, J1.5 Hz), 6.96-7.58 (15H, m), 8.38 (1H, d, J1.5 Hz). (Found C, 69.3; H, 6.4; N, 5.1; S, 5.6. C$_{32}$H$_{34}$N$_2$O$_3$SSi requires C, 69.3; H, 6.1; N, 5.1; S, 5.8%).

Preparation 4(b)

(3RS,4SR) 1-t-Butyldimethylsilyl-3-hydroxy(isoxazol-3-yl)methyl]-4-tritylthioazetidin-2-one A solution of the ketone (32) from preparation 4(a) (3.24 g, 5.86 mmol) in THF (30 ml) and EtOH (30 ml) at 0° under argon was treated portionwise with sodium borohydride (67 mg, 1.76 mmol). After 45 minutes a further portion of sodium borohydride (34 mg) was added. After a further 15 minutes the reaction mixture was quenched with saturated ammonium chloride solution and worked up as for preparation 3(b) to give two fractions. The less polar fraction contained a trans isomer (Isomer A) of the title azetidinone (33) (769 mg, 23%) mp. 203° (plates ex ethyl acetate/hexane); $\nu$max (CH$_2$Cl$_2$) 3650-3450, 1745 cm$^{-1}$ $\delta$(CDCl$_3$) (excluding Me$_2$Si groups which were masked by TMS) 0.96 (9H, s), 2.20 (1H, bs, exch.), 3.36 (1H, dd, J2, 3 Hz), 3.84 (1H, bs, collapses to d, J3 Hz on D$_2$O exchange), 4.51 (1H, d, J2 Hz), 6.49 (1H, d, J1.5 Hz), 7.07-7.60 (15H, m), 8.19 (1H, d, J1.5 Hz). (Found C, 69.1; H, 6.7; N, 5.1; S, 5.7. C$_{32}$H$_{36}$N$_2$O$_3$SSi requires, C, 69.1; H, 6.5; N, 5.0; S, 5.8%). The more polar fraction contained the other trans isomer (Isomer B) of the title azetidinone (33), (2.10 g, 65%), $\nu$max (CH$_2$Cl$_2$) 3600-3300, 1755 cm$^{-1}$; $\delta$(CDCl$_3$) (excluding Me$_2$-Si-groups which were masked by TMS), 0.80 (9H, s), 2.60 (1H, bs, exch.), 3.60 (1H, dd, J2, 5 Hz), 3.94 (1H, bd, collapses to d, J 5 Hz on D$_2$O exch.), 4.26 (1H, d, J2 Hz), 6.20 (1H, d, J2 Hz), 7.04-7.56 (15H, m), 8.16 (1H, d, J2 Hz). (Found [M+Et$_2$NH$_2$]$^+$ 630).

Preparation 4(c)

(3RS, 4SR) 3-[Hydroxy (isoxazol-3-yl)methyl]-4-tritylthioazetidin-2-one

The alcohol (33) (isomer B) (2.08 g, 3.74 mmol) from preparation 4(b) was treated as for preparation 2(b) to give the title azetidinone (34) (1.487 g, 94%). mp. 205°-206° (microplates ex ethyl acetate), $\nu$maz (CH$_2$Cl$_2$) 3600-3300, 3400, 1765 cm$^{-1}$; $\delta$(d7-DMF), 3.71 (1H, dd, J2.5, 3.3 Hz), 4.40 (1H, d, J2.5 Hz), 5.15 (1H, bd, sharpens to d, J3.3 Hz, on D$_2$O exch.), 6.35 (1H, bs, exch.), 6.51 (1H, d, J 1.5 Hz) 7.13 (1H, bs, exch), 7.24-7.46 (15H, m), 8.97 (1H, d, J1.4 Hz). (Found C, 70.4; H, 5.0; N, 6.3; S, 6.9. C$_{26}$H$_{22}$N$_2$O$_3$S requires C, 70.6; H, 5.0; N, 6.3; S, 7.2%).

Preparation 4(d)

(3RS, 4SR) 3-[Acetoxy (isoxazol-3-yl)methyl]-4-tritylthioazetidin-2-one

The alcohol (34) (1.4 g, 3.17 mmol) from preparation 4(c) was treated as for preparation (1c) to give the title acetate (35) (1.5 g, 98%) mp. 144°-145° (plates ex ethyl acetate/hexane) $\nu$max (CH$_2$Cl$_2$) 3400, 1780, 1755(sh) cm$^{-1}$; $\delta$(CDCl$_3$) 2.07 (3H, s), 3.62-3.76 (1H, m), 4.21 (1H, bs), 4.49 (1H, d, J3 Hz), 6.22 (1H, d, J5 Hz), 6.35 (1H, d, J2 Hz), 7.15-7.51 (15H, m), 8.41 (1H, d, J2 Hz); (Found C, 69.2; H, 5.1; N, 5.9; S, 6.4. C$_{28}$H$_{24}$N$_2$O$_4$S requires C, 69.4; H, 5.0; N, 5.8; S, 6.6%).

Preparation 4(e)

(3RS, 4SR) 3-[Acetoxy(isoxazol-3-yl)methyl]-1-(1-p-nitrobenzyloxycarbonyl-1-triphenylphosphoranylidenemethyl)-4-tritylthioazetidin-2-one The acetate (35) (484 mg, 1 mmol) from preparation 4(d) was converted to the hydroxyester (36) $\nu$max (CH$_2$Cl$_2$), 3500, 1775, 1750 cm$^{-1}$; the chloroester (37) $\nu$max (CH$_2$Cl$_2$), 1785, 1755(sh) cm$^{-1}$ and finally the title phosphorane (38) (596 mg, 64%), $\nu$max (CH$_2$Cl$_2$) 1755, 1720, 1620 cm$^{-1}$ using the methods described in preparation 1(d).

Preparation 4(f)

(3RS, 4SR) Silver 3-[Acetoxy(isoxazol-3-yl)methyl]-1-(1-p-nitrobenzyloxycarbonyl-1-triphenylphosphoranylidenemethyl azetidin-2-one-4-thiolate.

The phosphorane (38) (590 mg, 0.63 mmol) from Preparation 4(e) was treated with silver nitrate/pyridine as for preparation 1(e) to give the title silver salt (39) (447 mg, 89%) as an off-white solid.

Preparation 4(g)

(5RS, 6SR) p-Nitrobenzyl 6-[Acetoxy(isoxazol-3-yl)methyl]penem-3-carboxylate

The silver salt (39) (447 mg) from preparation 4(f) was treated as for preparation 1(f) to give the title penem (40) (179 mg, 72%). $\nu$max (EtOH) 262 nm (Em 12,890), 315 (8750); $\nu$max (CH$_2$Cl$_2$) 1800, 1755, 1720 cm$^{-1}$; $\delta$(CDCl$_3$) 2.16 (3H, s), 4.55-4.58 (1H, m), 5.28 and 5.42 (2H, ABq, J 13.6 Hz), 5.97 (1H, d, J 2.0 Hz), 6.33 (1H, d, J 3.5 Hz), 6.45 (1H, d, J 1.7 Hz), 7.35 (1H, d, J 0.9 Hz), 7.59 (2H, d, J 8.7 Hz), 8.24 (2H, d, J 8.7 Hz), 8.44 (1H, d, J 1.6 Hz).

EXAMPLE 4(a)

(5RS) p-Nitrobenzyl (Z)-6-(Isoxazol-3-ylmethylene)penem-3-carboxylate

The penem (40) (135 mg) from preparation 4(g) was treated as for example 1(a) to give the title penem (42) (115 mg, 92%) $\lambda$max 256 nm (Em 24,740), 305 (10,620); $\nu$max (CH$_2$Cl$_2$) 1790, 1720 cm$^{-1}$; $\delta$(CDCl$_3$) 5.30 and 5.46 (2H, Abq, J 13.6 Hz), 6.49 (1H, d, J 1.7 Hz , 6.50 (1H, d, J 1.2 Hz), 7.05 (1H, d, J 1.0 Hz), 7.41 (1H, s), 7.6 (2H, d, J 8.9 Hz), 8.25 (2H, d, J 8.8 Hz), 8.53 (1H, d, J 1.9 Hz).

EXAMPLE 4(b)

(5RS) Sodium (Z)-6-(Isoxazol-3-ylmethylene)penem-3-carboxylate

The penem ester (42) from example 4(a) was hydrogenated as for example 1(b) to give title sodium salt (43) (35 mg, 58%) as a yellow freeze-dried solid $\lambda$max H$_2$O) 248nm (Em 14,470 ,290(infl), 375 (1310 ; D$_2$O) 6.59 (1H, s), 6.67) (1H, s , 7.10 (1H, s), 7.22 (1H, s) 8.71 (1H, s).

Preparation 5(a)

2,4-Dimethyloxazole-5-carboxaldehyde 2,4-Dimethyloxazole-5-carboxylic acid (1.54 g) (J. W. Cornforth and R. H. Cornforth, JCS, 1953, 93), was suspended in thionyl chloride (20 ml) and heated at reflux temperature for one hour. The black solution was evaporated, toluene added and the process repeated to give the crude acid chloride (44) (1.15 g) as a black gum; $\nu$max (CH$_2$Cl$_2$) 1755 cm$^{-1}$; $\delta$(CDCl$_3$), 2.50 (s), 2.55 (s).

A solution of the crude acid chloride (44) (1.15 g) in acetone (20 ml) at room temperature was sequentially treated with triphenphosphine (4.2 g) and bis(triphenylphosphine) copper (I) tetrahydroborate (5.31 g). After one hour the reaction mixture was filtered and evaporated. Residue was stirred with ether for 10 minutes then filtered and evaporated. The residue was chromatographed on silica eluting with ethyl acetate/hexane mixtures to give the title aldehyde (45) (520 mg) as a low melting solid; $\nu$max (CH$_2$Cl$_2$) 1685, 1670 cm$^{-1}$; $\delta$(CDCl$_3$) 2.45 (3H, s), 2.54 (3H, s), 9.84 (1H, s). This material was of sufficient purity for further synthetic work.

Preparation 5(b)

1-t-Butyldimethylsilyl-3-[(2,4-dimethyloxazol-5-yl)hydroxymethyl]-4-tritylthioazetidin-2-one 1-t-Butyldimethylsilyl-4-tritylthioazetidin-2-one (1) (1.99 g, 4.34 mmol) was reacted with 2,4-dimethyloxazole-5-carboxaldehyde (45) (520 mg, 4.16 mmol) using the method described in preparation 1(a) to give after work-up two fractions which were partially separable by chromatography. The less polar fraction (290 mg) contained a 4:1 mixture of a trans (isomer A) and a cis isomer (isomer B) of the title azetidinone (46); $\nu$max (CH$_2$Cl$_2$) 3600–3300, 1745 cm$^{-1}$; $\delta$(CDCl$_3$) 0.13 (4.8H, s), 0.35 (0.6H, s), 0.38 (0.6H, s), 0.89 (7.2H, s), 0.98 (1.8H, s) 1.59 (0.8H, d, J5.6 Hz), 1.95 (0.6H, s), 1.99 (2.4H, s), 2.35 (2.4H, s), 2.36 (0.6H, s), 2.90 (0.2H, d, J5.3 Hz), 3.53 (0.2H, dd, J1.5, 4.6 Hz), 3.67 (0.8H, dd, J1.7, 3.2 Hz), 3.76 (0.2H, bd, J 4.7 Hz), 4.13 (0.8H, dd, J3.2, 5.6 Hz), 4.43 (0.8H d, J1.7 Hz), 4.79 (0.2H, d, J4.7 Hz), 7.15–7.56 (15H m). (Found [MH]+ 585). The more polar fraction (610 mg) contained a trans isomer (isomer C) of the title azetidinone (46); $\nu$max (CH$_2$Cl$_2$) 3600–3300, 1740 cm$^{-1}$; $\delta$(CDCl$_3$), −0.02 (3H, s). 0.09 (3H, s), 0.87 (9H, s), 1.81 (3H, s), 2.31 (3H, s), 2.56 (1H, d, J9.8 Hz), 3.79 (1H, dd, J1.9, 7.2 Hz), 4.04 (1H, d, J1.9 Hz), 4.09 (1H, dd, J7.3, 6 Hz), 7.12–7.53 (15H, m). (Found [MH]+ 585).

A 1:2 mixture of the less polar and more polar fractions (360 mg) was also isolated and this could be purified by further chromatography.

Preparation 5(c)

(3RS, 4SR) 3-[(2,4-Dimethyloxazol-5-yl)hydroxymethyl]-4-tritylthiazetidin-2-one The alcohol (46) (isomer C) (730 mg) from preparation 5(b) was treated as for preparation 1(b) to give the title azetidinone (47) (460 mg, 78%); $\nu$max (CH$_2$Cl$_2$) 3600–3200, 1770 cm$^{-1}$; $\delta$(CDCl$_3$), 2.14 (3H, s), 2.53 (3H, s), 2.60 (1H, bs, exch.), 3.45 (1H, dd, J 2.7, 4.0 Hz), 4.18 (1H, s), 4.47 (1H, d, J2.7 Hz), 5.13 (1H, bd, sharpens to d, J4.0 Hz on D$_2$O exch.), 7.12–7.53 (15H, m). (Found [MH+diethylamine]+ 544).

Preparation 5(d)

(3RS, 4SR) 3-[Acetoxy(2,4-dimethyloxazol-5-yl)methyl]-4-tritylthioazetidin-2-one The alcohol (47) (410 mg) from preparation 5(c) was treated as for preparation 1(c) to give title azetidinone (48) (430 mg, 96%); $\nu$max (CH$_2$Cl$_2$) 3380, 1775, 1740 cm$^{-1}$; $\delta$(CDCl$_3$), 2.07 (3H, s), 2.13 (3H, s), 2.46 (3H, s), 3.59 (1H, dd with further fine coupling J~3~7 Hz), 4.22 (1H, bs), 4.63 (1H, d, J2.7 Hz), 6.14 (1H, d, J6.7 Hz), 7.22–7.73 (15H, m).

Preparation 5(e)

(3RS, 4SR) 3-[Acetoxy(2,4-dimethyloxazol-5-yl)methyl-1-(1-p-nitrobenzyloxycarbonyl-1-triphenylphosphoranylidenemethyl)-4-tritylthioazetidin-2-one The acetate (48) (410 mg) from preparation 5(d) was converted via the hydroxyester (49), $\nu$max (CH$_2$Cl$_2$) 3500, 1775, 1750 cm$^{-1}$; and the chloroester (50), $\nu$max (CH$_2$Cl$_2$) 1785, 1750 cm$^{-1}$; to the title phosphorane (51) (443 mg, 57%) $\nu$max (CH$_2$Cl$_2$) 1760, 1620 cm$^{-1}$; using the methods described in preparation 1(d).

Preparation 5(f)

(3RS, 4SR) Silver 3-[Acetoxy(2,4-dimethyloxazol-5-yl)methyl)-1-(1-p-Nitrobenzyloxycarbonyl-1-triphenylphosphoranylidenemethyl)azetidin-2-one-4-thiolate The phosphorane (51) (440 mg) from preparation 5(e) was treated as for preparation 1(e) to give the title silver salt (52) (345 mg, 91%) as an off-white solid.

Preparatin 5(g)

(5RS, 6SR) p-Nitrobenzyl 6-[Acetoxy(2,4-dimethyloxazol-5-yl)methyl]penem-3-carboxylate The silver salt (52) (345 mg) from preparation 5(f) was treated as for preparation 1(f) to give the title penem (53) (130 mg, 66%); $\nu$max EtOH, 314 nm (Em 9350), 262 (12970); $\nu$max (CH$_2$Cl$_2$), 1795, 1745, 1720 cm$^{-1}$; (CDCl$_3$) 2.09 (3H, s), 2.20 (3H, s), 2.42 (3H, s), 4.27 (1H, ddd, J1.0, 1.8 4.4 Hz), 5.28 and 5.42 (2H, ABq, J13.5 Hz), 6.08 (1H, d, J2.0 Hz), 6.2 (1H, d, J4.5 Hz), 7.32 (1H,d, J 1.0 Hz), 7.59 (2H, d, J8.7 Hz), 8.29 (2H (2H, d, J8.7 Hz).

EXAMPLE 5(a)

(5RS) p-Nitrobenzyl (Z)-6-[(2,4-dimethyloxazol-5-yl)methylene]penem-3-carboxylate.

The penem (53) (99 mg) from preparation 5(g) was treated as for example 1(a) to give the title penem (54) (75mg, 82%) mp. 203°–204° (yellow/orange microneedles ex CH$_2$Cl$_2$/Hexane); $\lambda$max (EtOH) 311 nm Em 34,430 ; $\nu$max (CH$_2$Cl$_2$), 1780, 1720, 1670 cm$^{-1}$; $\delta$(CDCl$_3$) 2.27 (3H, s), 2.51 (3H, s), 5.30 and 5.46 (2H, ABq, J13.6 Hz), 6.55 (1H, d, J0.8 Hz), 6.96 (1H, d, J0.7 Hz), 7.37 (1H, s), 7.37 (1H, s), 7.62 (2H, d, J8.7 Hz), 8.25 (2H, d, J8.7 Hz). (Found M+ 413.0678. C$_{19}$H$_{15}$N$_3$O$_6$S requires M+ 413.0682).

EXAMPLE 5(b)

(5RS) Sodium (Z)-6-[(2,4-dimethyloxazol-5-yl)methylene]penem-3-carboxylate

The penem ester (54) from example 5(a) was hydrogenated as for example 1(b) to give the title sodium salt (55) (28 mg, 77%) as a yellow freeze-dried solid; $\nu$max (H$_2$O) 305 nm Em 22,330); $\delta$(D$_2$O) 2.22 (3H, s), 2.28 (3H, s), 6.61 (1H, s), 7.06 (1H, s); 7.11 (1H, s).

Preparation 6(a)

(3RS,4SR) 1-t-Butyldimethylsilyl-3-(4-methyl-1,2,3-thiadiazol-5-ylcarbonyl;-4-tritylthioazetidin-2-one 1-t-Butyldimethylsilyl-4-tritylthioazetidin-2-one (1) (9.18 g) was reacted with ethyl 4-methyl-1,2,3-thiadiazole-5-carboxylate (6.88 g) (R. Raap and R. G. Micetich, Can. J. Chem., 1968, 46, 1057) using the method described in preparation 4(a). The crude product was chromatographed on silica eluting with dichloromethane/hexane mixtures to give, after trituration with ether, the title azetidinone (56). (7.19 g, 61%); m.p. 163°–165° (needles ex ethylacetate/hexane); $\nu$max (CH$_2$Cl$_2$) 1750, 1680 cm$^{-1}$; $\delta$(CDCl$_3$) 0.40 (3H, s), 0.41 (3H, s), 0.99 (9H, s) 2.84 (3H, s), 3.78 (1H, d, J1.6 Hz), 5.03 (1H, d, J1.6 Hz), 6.96–7.09 (3H, m), 7.12–7.28 (6H, m), 7.31–7.52 (6H, m). (Found: C, 65.6; H, 6.2; N, 7.3; S, 11.2. C$_{32}$H$_{35}$N$_2$O$_2$S$_2$Si requires C, 65.6; H, 6.0; N, 7.2; S, 11.0%).

Preparation 6(b)

(3RS,4SR) 1-t-Butyldimethylsilyl-3-[hydroxy(4-methyl-1,2,3-thiadiazol-5-yl)methyl]-4-tritylazetidin-2-one The ketone (56) (6.9 g) from preparation 6(a) was treated as for preparation 4(b) to give two fractions. The less polar fraction contained a trans isomer (isomer A) of the title azetidinone (57) (1.98 g, 28%) $\nu$max (CHCl$_3$) 3600–3150, 1740 cm$^{-1}$; $\delta$(CDCl$_3$), (excluding Me$_2$Si groups which were obscured by TMS), 0.87 (9H, s), 2.01 (1H, d, J6 Hz), 2.43 (3H, s), 3.49 (1H, dd, J2,4 Hz), 4.23 (1H dd, J4,6 Hz), 4.40 (1H, d, J2 Hz), 7.11–7.55 (15H, m). The more polar fraction contained the other trans isomer (isomer B) of the title azetidinone (57) (4.04 g, 58%), m.p. 183°–185° (needles ex ethyl acetate/hexane); $\nu$max (CHCl$_3$) 3600–3150 1730 cm$^{-1}$; $\delta$(CDCl$_3$) (excluding Me$_2$-Si groups which were masked by TMS), 0.83 (9H, s), 2.37 (3H, s), 2.76 (1H, bs), 3.65 (1H, dd, J2,6 Hz), 4.58 (1H, bd; J6 Hz), 7.18–7.51 (15H, m). (Found: C, 65.4; H, 6.4; N, 7.2; S, 10.6. C$_{32}$H$_{37}$N$_2$O$_2$S$_2$ requires C, 65.4; H, 6.3; N, 7.2; S, 10.9%).

Preparation 6(c) (3RS, 4SR) 3-[Hydroxy(4-methyl-1,2,3-thiadiazol-5-yl)methyl]-4-tritylthioazetidin-2-one The alcohol (57) (isomer B) (3.34 g), from preparation 6(b) was treated as for preparation 2(b) to give the title azetidinone (58) (2.49 g, 91%); m.p. 250°–253°, (prisms ex chloroform/ether), $\nu$max (KBr) 3640–3060, 1760 cm$^{-1}$, $\delta$(d$_6$-DMSO) 2.57 (3H, s), 3.61 (1H, dd, J3,4 Hz), 4.01 (1H, d, J3 Hz), 5.29 (1H, dd, J4,4 Hz, collapses to d, J4 Hz on D$_2$O exch.); 6.74 (1H, d, J4 Hz, exch.), 7.04–7.38 (15H, m), 7.58 (1H, s, exch.). (Found: C, 66.3; H, 4.8; N, 8.8; S, 13.32. C$_{26}$H$_{23}$N$_3$O$_2$S$_2$ requires C, 65.9; H, 4.9; N, 8.9; S, 13.5%).

Preparation 6(d)

(3RS, 4SR) 3-[Acetoxy 4-methyl-1,2,3-thiadiazol-5-yl)methyl -4-tritylthioazetidin-2-one The alcohol (58) (2.49 g) from preparation 6(c) was treated as for preparation 1(c) to give the title acetate (59) (2.32 g, 86%); m.p. 215° (dec) (plates ex ethyl acetate/hexane); $\nu$max (Nujol) 3375, 1770, 1755 cm$^{-1}$ $\delta$(CDCl$_3$), 2.07 (3H, s), 2.68 (3H, s), 3.53 (1H, dd, J3,6 Hz), 4.28 (1H, bs, exch.), 4.35 (1H, d, J3 Hz), 6.37 (1H, d, J 6 Hz), 7.13–7.46 (15H, m). (Found: C, 65.5; H, 5.0; N, 8.0; S, 12.1. C$_{28}$S, 12.1. C$_{28}$H$_{25}$N$_3$O$_3$S$_2$ requires C, 65.2; H, 4.9; N, 8.1; S, 12.4%).

Preparation 6(e)

(3RS, 4SR) 3-[Acetoxy(4-methyl-1,2,3-thiadiazol-5-yl)methyl]-1-(1-p-nitrobenzyloxycarbonyl-1-triphenylphosphoranylidenemethyl)-4-tritythioazetidin-2-one The acetate (59) (2.03 g) from preparation 6(d) was converted via the hydroxy esters (60), $\nu$max (CHCl$_3$) 3500, 1775, 1750 cm$^{-1}$; and the chloro ester (61), to the title phosphorane (62) (2.62 g, 69%) m.p. 237°–239° (plates ex CH$_2$Cl$_2$/MeOH) $\nu$max (CHCl$_3$), 1725, 1615 cm$^{-1}$. (Found, C, 68.3; H, 4.5; N, 5.6; S, 6.8; P, 3.3. C$_{55}$H$_{45}$N$_4$S$_2$O$_7$P requires C, 68.2; H, 4.7; N, 5.8; S, 6.6; P, 3.2%), using the methods described in preparation 1(d).

Preparation 6(f)

(3RS, 4SR) Silver 3-[Acetoxy(4-methyl-1,2,3-thiadiazol-5-yl)methyl-1-(1-p-nitrobenzyloxycarbonyl-1-triphenylphosphoranylidenemethyl)azetidin-2-one-4-thiolate The phosphorane (62) (2.00 g) from preparation 6(e) was treated as for preparation 1(e) to give the title silver salt (63) (1.70 g) $\nu$max (Nujol) 1750, 1595 cm$^{-1}$.

Preparation 6(g)

(5RS, 6SR) p-Nitrobenzyl 6-[Acetoxy (4-methyl-1,2,3-thiadiazol-5-yl)methyl]penem-3-carboxylate The silver salt (63) (350 mg) from preparation 6(f) was treated as for preparation 1(f) to give the title penem (64) (100 mg, 50%); m.p. 151°–154°, (light yellow needles ex ethyl acetate/hexane), $\nu$max (2% CHCl$_3$/EtOH) 312 nm (Em 7500), 261 (15610); $\nu$max (CH$_2$Cl$_2$, 1795, 1750, 1720 cm$^{-1}$; $\delta$(CDCl$_3$) 2.08 (3H, s), 2.75 (3H, s), 4.19 (1H, with further fine coupling, J6 Hz), 5.21 and 5.40 (2H, ABq, J14 Hz), 5.79 (1H, d, J2 Hz), 6.47 (1H, d, J6 Hz), 7.26 (1H, s), 7.51 (2H, d, J9 Hz), 8.18 (2H, d, J9 Hz). (Found C, 47.7; H, 3.5; N, 11.8; S, 13.3 Cl$_9$H$_{16}$N$_4$S$_2$O$_7$ requires C, 47.9; H, 3.4; N, 11.7; S, 13.5%).

EXAMPLE 6(a)

(5RS) p-Nitrobenzyl 6-[(4-methyl-1,2,3-thiadiazol-5-yl)methylene]penem-3-carboxylate The penem (64) (315 mg) from preparation 6(g) was treated as for example 1(a) to give two products. The less polar material contained the Z isomer of the title penem (65) (129 mg, 47%) m.p. 174°–177° (orange plates ex chloroform/hexane); νmax (2% CHCl$_3$/EtOH) 308 nm (Em 25200), 264 (21630); νmax (CHCl$_3$), 1785, 1715 cm$^{-1}$; δ(CDCl$_3$) 2.84 (3H, s), 5.31 and 5.46 (2H, ABq, J13.4 Hz), 6.38 (1H, d, J1.0 Hz), 7.37 (1H, d, J0.8 Hz), 7.39 (1H, s), 7.61 (2H, d, J8.7 Hz), 8.25 (2H, d, J8.7 Hz); (Found: C, 49.1; H, 2.9; N, 13.2; S, 15.6. C$_{17}$H$_{12}$N$_4$S$_2$O$_5$ requires C, 49.1; H, 2.9; N, 13.5; S, 15.4%). The more polar material contained the E-isomer of the title penem (65) (41 mg, 15%), m.p. 205°-208° (orange microcrystalline solid ex CHCl$_3$/CH$_2$Cl$_2$/hexane), νmax (2% CHCl$_3$/EtOH), 309 nm (Em 22450), 263 (17590); νmax (KBr), 1780, 1720 cm$^{-1}$; δ(CDCl$_3$), 2.81 (3H, s), 5.33 and 5.44 (2H, ABq, J13.5 Hz), 6.49 (1H, s), 6.82 (1H, d, J0.5 Hz), 7.45 (1H, s), 7.61 (2H, d, J8.9 Hz), 8.26 (2H, d, J8.8 Hz). (Found M+416.025. C$_{17}$H$_{12}$N$_4$O$_5$S$_2$ requires M 416.025).

EXAMPLE 6(b)

(5RS) Sodium (E)-6-[(4-methyl-1,2,3-thiadiazol-5-yl)methylene]-penem-3-carboxylate The (E)-penem ester (65) (62 mg) from example 6(a) was hydrogenated as for example 1(b) to give the title sodium salt (66) (11 mg, 27%) as an orange freeze-dried solid, νmax (H$_2$O) 280 nm (Em 5729), 306 (8,290); δ(D$_2$O) 2.72 (3H, s), 6.52 (1H, s), 7.09 (1H, s), 7.15 (1H, s).

EXAMPLE 6(c)

(5RS) Sodium (Z)-6-[(4-methyl-1,2,3-thiadiazol-5-yl)methylene]-penem-3-carboxylate The (Z)-penem ester (65) (90 mg) from example 6(a) was hydrogenated as for example 1(b) to give the title sodium salt (67) (23 mg, 38%) as an orange freeze-dried solid; λmax (H$_2$O) 265 nm (Em 9740), 306 (13970); δ(D$_2$O) 2.76 (3H, s), 6.53 (1H, s), 7.09 (1H, s), 7.51 (1H, s).

Preparation 7(a)

(3RS,4SR) 1-t-Butyldimethylsilyl-3-(2-methyloxazol-4-ylcarbonyl)-4-tritylthioazetidin-2-one 1-t-Butyldimethylsilyl-4-tritylthioazetidin-2-one (1) (9.18 g) was reacted with ethyl 2-methyloxazole-4-carboxylate (3.56 g) (J. W. Cornforth and R. H. Cornforth, JCS, 1947, 96) using the method described in preparation 4(a) to give the title azetidinone (68) (6.89 g, 60%); m.p. 163°-166° (plates ex ethyl acetate/hexane), νmax (CH$_2$Cl$_2$) 1725, 1680 cm$^{-1}$; δ(CDCl$_3$) (excluding Me$_2$Si groups which were obscured by TMS). 2.47 (3H, s), 4.23 (1H, d, J3 Hz), 4.89 (1H, d, J3 Hz), 6.99-7.67 (15H, m), 8.00 (1H, s); (Found: C, 69.4; H, 6.6; N, 4.9; S, 5.5. C$_{33}$H$_{36}$N$_2$O$_3$SSi requires C, 69.7; H, 6.4; N, 4.9; S, 5.6%).

Preparation 7(b)

(3RS,4SR) 1-t-Butyldimethylsilyl-3-[hydroxy(2-methyloxazol-4-yl)methyl]-4-tritylthioazetidin-2-one The ketone (68) (6.79 g) from preparation 7(a) was treated as for preparation 4(b) to give two fractions. The less polar fraction contained a trans isomer (isomer A) of the title azetidinone (69) (1.31 g, 19%), m.p. 200°-203° (plates ex ethylacetate/hexane); νmax (Nujol) 3250, 1725 cm$^{-1}$; δ(d6-DMSO) (excluding Me$_2$-Si 3.73-3.80 (1H, m) collapses to 3.75 (bs) on D$_2$O exch.), 4.38 (1H, bs); d, J5 Hz), 4.56 (1H, d, J2 Hz), 7.22-7.56 (16H, m). (Found MH+ 571). The more polar fraction contained the other trans isomer (isomer B) of the title azetidinone (69) (4.27 g, 62%)—this material was contaminated with about 5% of the azetidinone (69) (isomer A), but was used in further synthetic transformations. Recrystallization from ethyl acetate/hexane afforded pure (isomer B) m.p. 196°-198°; νmax (CH$_2$Cl$_2$) 1720 cm$^{-1}$; δ(d6-acetone), (excluding Me$_2$Si signals which were obscured by TMS) 2.31 (3H, s), 3.73 (1H, bs, collapses to dd, J1.6, 2.9 Hz on D$_2$O exch.) 4.08 (2H, bs collapses to 1H, d, J1.6 Hz on D$_2$O exch.) 4.55 (1H, d, J1.8 Hz), 7.22-7.56 (16H, m); (Found, C, 69.1; H, 6.6; N, 4.9; S, 5.7. C$_{33}$H$_{38}$N$_2$O$_3$SSi requires C, 69.4; H, 6.7; N, 4.9; S, 5.6%).

Preparation 7(c)

(3RS, 4SR) 3-[Hydroxy(2-methyloxazol-4-yl)methyl]-4-tritylthioazetidin-2-one The alcohol (69) (isomer B) (4.1 g) from preparation 7(b) was treated as for preparation 2(b) to give the title azetidinone (70) (2.84 g, 86%). νmax (CH$_2$Cl$_2$), 3400, 1765 cm$^{-1}$ δ(CDCl$_3$) 2.55 (3H, s), 3.20 (1H, bs, exch.), 3.63 (1H, dd, J2.7, 3.5 Hz), 4.23 (1H, bs), 4.54 (1H, d, J2.7 Hz), 5.08 (1H, d, J3.6 Hz), 7.19-7.40 (15H, m), 7.62 (1H, d, J1.0 Hz).

Preparation 7(d)

(3RS, 4SR) 3-[Acetoxy(2-methyloxazol-4-yl)methyl]-4-tritylthioazetidin-2-one The alcohol (70) (2.84 g) from preparation 7(c) was treated as for preparation 1(c) to give the title acetate (71) (3.09 g) m.p. 147-150 (microcrystalline ex ethyl acetate/hexane); νmax (CHCl$_3$) 3380, 1770 cm$^{-1}$; δ(CDCl$_3$) 2.07 (3H, s), 2.48 (3H, s), 3.65-3.87 (1H, m), 4.28 (1H, bs), 4.58 (1H, d, J3 Hz), 6.07 (1H, d, J10 Hz), 7.10-7.51 (16H, m). (Found, C, 69.7; H, 5.1; N, 5.6; S, 6.4. C$_{29}$H$_{26}$N$_2$O$_4$S requires C, 69.9; H, 5.2; N, 5.6; S, 6.4%).

Preparation 7(e)

(3RS, 4SR) 3-[Acetoxy(2-methyloxazol-4-yl)methyl]-1-(1-p-nitrobenzyloxycarbonyl-1-triphenylphosphoranylidenemethyl)-4-tritylthioazetidin-2-one The acetate (71) (2.63 g) from preparation 7(d) was converted via the hydroxy esters (72), νmax (CHCl$_3$), 3510, 1760 cm$^{-1}$; and the chloroesters (73), νmax (CHCl$_3$) 1775 cm$^{-1}$; to the title phosphorane (74), (3.14 g, 63%), νmax (CHCl$_3$) 1725, 1605 cm$^{-1}$, using the methods described in preparation 1(d).

Preparation 7(f)

(3RS, 4SR) Silver 3-[Acetoxy(2-methyloxazol-4-yl)methyl]-1-(1-p-nitrobenzyloxycarbonyl-1-triphenylphosphoranylidenemethyl)azetidin-2-one-4-thiolate The phosphorane (74) (3.14 g) from preparation 7(e) was treated as for preparation 1(e) to give the title silver salt (75) 1.92 g, 95% as a buff solid, νmax (Nujol) 1720, 1600 cm$^{-1}$.

Preparation 7(g)

(5RS, 6SR) p-Nitrobenzyl 6-[Acetoxy(2-methyloxazol-4-yl)methyl]penem-3-carboxylate The silver salt (75) (1.92 g) from preparation 7(f) was treated as for preparation 1(f) to give two fractions. The less polar fration contained the title penem (76) (isomer B) (554 mg, 51%) m.p. 137°–139° (microcrystalline ex ethyl acetate/hexane, λmax (2% CHCl$_3$/EtOH), 261 nm (Em 16345), 316 (9160); νmax (CHCl$_3$) 1795, 1720 cm$^{-1}$; CDCl$_3$), 2.09 (3H, s , 2.43 (3H, s), 4.36 (1H, dddd, J1.1, 1.9, 3.8 Hz), 5.27 and 5.42 (2H, ABq, J13.6 Hz), 6.10–6.13 (2H, m), 7.33 (1H, d, J0.9 Hz), 7.59 (2H, d, J9.4 Hz), 7.61 (1H, s), 8.23 (2H, d, J8.8 Hz). (Found: C, 52.2; H, 3.7; N, 9.1; S, 7.0. C$_{20}$H$_{17}$N$_3$SO$_8$ requires C, 52.3; H, 3.7; N, 9.1; S, 7.0%). This material was derived from the alcohol (69) (isomer B). The more polar fraction contained an impure sample of the title penem (76) (isomer A) (100 mg), νmax CHC$_{13}$ 1790, 1720 cm$^{-1}$; δ(CDCl$_3$) 2.15 (3H, s , 2.45 (3H, s), 2.45 (3H, s , 4.45–4.49 (1H, m , 5.25 and 5.40 (2H, ABq, J13.5 Hz), 5.78 (1H, d, J2.0 Hz), 6.20 (1H, d, J5.9 Hz), 7.31 (1H, d, J1.0 Hz), 7.57 (2H, d, J8.7 Hz), 7.64 (1H, d, J0.4 Hz), 8.23 (2H, d, J8.7 Hz).

EXAMPLE 7(a)

(5RS) p-Nitrobenzyl 6-[(2-methyloxazol-4-yl)methylene]penem-3-carboxylate

The penem 76) (isomer B) (610 mg) from preparation 7(g) was treated as for example 1(a) to give two products. The less polar material contained the (Z)-isomer of title penem (77) (518 mg, 97%) m.p. 199°–201° (orange needles ex CHCl$_3$/CH$_2$Cl$_2$/hexane); νmax (2% CHCl$_3$/EtOH) 287 nm Em 27260); νmax (KBr) 1785, 1710 cm$^{-1}$; δ(CDCl$_3$) 2.48 (3H, s), 5.28 and 5.45 (2H, ABq, J13.6 Hz), 6.63 (1H, d, J1.1 Hz), 6.93 (1H, d, J0.8 Hz), 7.37 (1H, s), 7.62 (2H, d, J8.7 Hz), 7.78 (1H, s), 8.24 (2H, d, J8.7 Hz); (Found; C, 54.1; H, 3.2; N, 10.6; S, 7.6. C$_{18}$H$_{13}$N$_3$SO$_6$ requires C, 54.1; H, 3.3; N, 10.5; S, 8.0%). The more polar fraction contained the (E) isomer of the title penem (77) (17mg, 3%). νmax (KBr) 1777, 1710 cm$^{-1}$; δ(CDCl$_3$) 2.49 (3H, s), 5.30 and 5.45 (2H, ABq, J13.5 Hz), 6.45 (1H, s), 6.57 (1H, s), 7.42 (1H, s), 7.61 (2H, d, J8.6 Hz), 8.25 (2H, d, J8.7 Hz), 8.68 (1H, d, J0.6 Hz).

EXAMPLE 7(b)

(5RS) p-Nitrobenzyl 6-[(2-methyloxazol-4-yl)methylene]penem-3-carboxylate

The penem (76) (isomer A) (85 mg) from preparation 7(g) was treated as for example 1(a) to give the (Z) isomer (27 mg) and the (E) isomer (26 mg) of the title penem (77). These materials were identical to those obtained from example 7(a).

EXAMPLE 7(c)

(5RS) Sodium (Z)-6-[(2-methyloxazol-4-yl)methylene]penem-3-carboxylate

The (Z)-penem ester (77) (100 mg) from example 7(a) was hydrogenated as for example 1(b) to give the title sodium salt (78) (49 mg, 69%) as a yellow freeze dried solid; λmax (H$_2$O) 286 nm (Em 20,000); δ(D$_2$O) 2.47 (3H, s), 6.64 (1H, s), 7.05 (1H, s), 7.07 (1H, s), 8.06 (1H, s).

Preparation 8(a)

(3RS,4SR)1-t-Butyldimethylsilyl-3-(1-methyl-1,2,3-triazol-4-yl-carbonyl)-4-tritylthioazetidin-2-one A solution of diisopropylamine (1.8 ml, 12.4 mmol) in dry THF (80 ml) under argon at −30° was treated dropwise with a solution of n-butyl lithium (1.7M, 7.3 ml, 12.4 mmol) in hexane. After 15 minutes the reaction mixture was cooled to -70° and treated dropwise with a solution of the azetidinone (1) (4.59 g, 10 mmol) in THF (80 ml). After a further 15 minutes the resulting pink solution was removed from the cooling bath and immediately treated in one portion with a hot solution of methyl 1-methyl-1,2,3-triazole-4-carboxylate (1.75 g, 12.4 mmol) (prepared by treating methyl propiolate with excess methyl azide; mp 161 lit. m.p. 159°–161° [T. C. Thurber and L. D. Townsend, J. Org. Chem., 1976, 41, 1041] in THF (100 ml). After a few minutes the reaction mixture was returned to the cooling bath. After a further 10 minutes the reaction mixture was quenched with saturated ammonium chloride and worked-up as in Preparation 3(a) to give the title azetidinone (79) 4.7 g, 83% m.p. 170°–171° (plates ex ethyl acetate/hexane); ν$_{max}$(CH$_2$Cl$_2$) 1745, 1680 cm$^{-1}$; δ(CDCl$_3$) (excluding Me$_2$Si signals) which were masked by TMS) 0.98 (9H, s), 4.04 (3H, s), 4.80 (1H, d, J1.5 Hz), 5.01 (1H, d, J1.5 Hz), 7.02–7.65 (15H, m), 7.89 (1H, s). (Found C, 67.5; H, 6.3; N, 9.7; S, 5.5. C$_{32}$H$_{36}$N$_4$O$_2$SSi requires C, 67.6; H, 6.3; N, 9.9; S, 5.6%).

Preparation 8(b)

(3RS,4SR)1-t-Butyldimethylsilyl-3-[hydroxy(1-methyl-1,2,3-triazol-4-yl)methyl]-4-tritylthioazetidin-2-one The ketone (79) (4.8 g, 8.45 mmol) from Preparation 8(a) was treated with sodium borohydride (642 mg, 16.90 mmol) as for Preparation 4(b) to give two fractions. The less polar fraction contained a trans isomer (isomer A) of the title azetidinone (80) (1.12 g, 23%), m.p. 221°–222° (rods ex ethyl acetate), ν$_{max}$ (CH$_2$Cl$_2$) 00, 1740 cm$^{-1}$ δ(CDCl$_3$) 0.30 (6H, s), 0.96 (9H, s), 1.94 (1H, d, J4.1 Hz), 3.34 (1H, bs) 3.84 (1H, bs, collapses to d, J1.7 Hz on irradiation a 61.94) 4.01 (3H, s), 4.54 (1H, d, J1.7 Hz), 7.18–7.49 (15H, m), 7.90 (1H, s). (Found C, 67.4; H, 6.8; N, 9.6; S, 5.4. C$_{32}$H$_{38}$N$_4$O$_2$SSi requires C, 67.4; H, 6.7; N, 9.8; S, 5.6%). The more polar fraction contained the other trans isomer (isomer B) of the title azetidinone (80) (3.01 g, 62%) ν$_{max}$ (CH$_2$Cl$_2$) 3600–3400, 1735 cm$^{-1}$; δ(CDCl$_3$) −0.04 (3H, s), 0.05 (3H, s), 0.78 (9H, s), 2.57 (1H, d, J8.5 Hz), 3.62 (1H, dd, J1.6, 5.9 Hz), 3.97 (3H, s), 4.10 (1H, dd, J6.0, 8.5 Hz), 4.46 (1H, d, J1.7 Hz), 7.15–7.58 (16H, m).

Preparation 8(c)

(3RS, 4SR) 3-[Hydroxy(1-methyl-1,2,3-triazol-4-yl)methyl]-4-tritylthioazetidin-2-one The alcohol (80) (isomer B) (3.01 g) from Preparation 8(b) was treated as for preparation 2(b) to give the title azetidinone (81) (2.27 g, 94%); ν$_{max}$ (CH$_2$Cl$_2$) 3600–3400, 1765 cm$^{-1}$; δ(CDCl$_3$), 3.47 (1H, d, J4.9 Hz), 3.63 (1H, ddd, J1.0, 2.7, 5.2 Hz), 4.16 (3H, s), 4.31 (1H, bs), 4.60 (1H, d, J2.7 Hz), 5.25 (1H, dd, J5.1, 5.1 Hz), 7.15–7.46 (15H, m), 7.63 (1H, s).

Preparation 8(d)

(3RS, 4SR) 3-[Acetoxy(1-methyl-1,2,3-triazol-4-yl)methyl]-4-tritylthioazetidin-2-one The alcohol (81) (2.17 g) from Preparation 8(c) was treated as for Preparation 1(c) to give the title acetate (82) (2.31 g, 97%); $\nu_{max}$ (CH$_2$Cl$_2$) 3400, 1775, 1740 (sh) cm$^{-1}$; δ(CDCl$_3$) 2.11 (3H, s), 3.83 (1H, ddd, J1.1, 2.7, 6.5 Hz), 4.11 (3H, s), 4.17 (1H, bs), 4.69 (1H, d, J2.7 Hz), 6.17 (1H, d, J6.4 Hz), 7.14–7.62 (16H, m).

Preparation 8(e)

(3RS, 4SR) 3-[Acetoxy(1-methyl-1,2,3-triazol-4-yl)methyl]-1-(1-p-nitrobenzyloxycarbonyl-1-triphenylphosphoranylidenemethyl)-4-tritylthioazetidin-2-one The acetate (82) (2.2 g) from Preparation 8(d) was converted via the hydroxy esters (83), $\nu_{max}$ (CH$_2$Cl$_2$) 3500, 1775, 1750 cm$^{-1}$; and the chloro esters, $\nu_{max}$ (CH$_2$Cl$_2$) 1780, 1750 cm$^{-1}$ to the title phosphorane (84) (2.98 g, 71%), $\nu_{max}$ (CH$_2$Cl$_2$) 1750, 1620 cm$^{-1}$, using the methods described in Preparation 1(d).

Preparation 8(f)

(3RS, 4SR) Silver 3-[acetoxy(1-methyl-1,2,3-triazol-4-yl)methyl]-1-(1-p-nitrobenzyloxycarbonyl-1-triphenylphosphoranylidenemethyl)azetidin-2-one-4-thiolate The phosphorane (84) (951 mg, 1 mmol) in dichloromethane (1 ml) and methanol (10 ml) under argon at room temperature was treated with pyridine (0.105 ml, 1.3 mmol) and a solution of silver nitrate (0.15M, 8.7 ml, 1.3 mmol) in methanol. After 30 minutes the reaction mixture was evaporated to give the crude silver salt (85). This material was of sufficient purity for further synthetic transformations.

Preparation 8(g)

(5RS, 6SR) p-Nitrobenzyl 6-[acetoxy(1-methyl-1,2,3-triazol-4-yl)methyl]penem-3-carboxylate The crude silver salt (85) from Preparation 8(f) was treated as for Preparation 1(f) to give the title penem (86) (227 mg, 52%), $\nu_{max}$ (CH$_2$Cl$_2$) 1795, 1740, 1720, 1605 cm$^{-1}$; δ(CDCl$_3$) 2.09 (3H, s), 4.09 (3H, s), 4.56 (1H, bs), 5.28, and 5.43 (2H, ABq, J13.5 Hz), 6.20 (1H, d, J3.4 Hz), 6.23 (1H, d, J2.0 Hz), 7.36 (1H, d, J0.7 Hz), 7.60 (2H, d, J8.6 Hz), 7.67 (1H, s), 8.24 (1H. d, J8.7 Hz).

EXAMPLE 8(a)

(5RS) p-Nitrobenzyl 6-(1-methyl-1,2,3-triazol-4-yl-methylene)penem-3-carboxylate The penem (86) (217 mg) from Preparation 8(g) was treated as for Example 1(a) to give the (Z)-isomer of the title penem (87a) (160 mg; 85%), $\nu_{max}$ (CH$_2$Cl$_2$) 1780, 1715 cm$^{-1}$; δ(CDCl$_3$) 4.15 (3H, s), 5.29 and 5.46 (2H, ABq, J13.6 Hz), 6.68 (1H, d, J0.8 Hz), 7.06 (1H, d, J1.0 Hz), 7.39 (1H, s), 7.63 (2H, d, J8.6 Hz), 7.72 (1H, s), 8.24 (2H, d, J8.8 Hz). (Found M+ 399.0637. C$_{17}$H$_{13}$N$_5$O$_5$S requires M 399.0638).

Also obtained was the (E)-isomer of the title penem (87b) (5%), $\nu_{max}$ (KBr) 1750, 1710, 1600 cm$^{-1}$; δppm (CDCl$_3$) 4.17 (3H, s), 5.31 and 5.43 (2H, ABq, J13.6 Hz), 6.48 (1H, d, J0.6 Hz), 6.94 (1H,s), 7.45 (1H, s), 7.62 (2H, d, J8.8 Hz), 8.26 (2H, d, J8.8 Hz), 8.74 (1H, s) (Found M+, 399.0632. C$_{17}$H$_{17}$N$_5$O$_5$S requires M, 399.0638).

EXAMPLE 8(b)

(5RS) Sodium (Z)-6-(1-methyl-1,2,3-triazol-4-yl-methylene)penem-3-carboxylate

The (Z)-penem ester (87a) (150 mg) from Example 8(a) was hydrogenated as for Example 1(b) to give the title sodium salt (88a) (80 mg, 74%) as a yellow freeze-dried solid; $\lambda_{max}$ (H$_2$O) 282 nm (Em 19,880); δ(D$_2$O) 4.13 (3H, s), 6.62 (1H, s), 7.07 (1H, s), 7.21 (1H, s), 8.16 (1H, s).

EXAMPLE 8(c)

(5RS) Sodium (E)-6-(1-methyl-1,2,3-triazol-4-yl-methylene)penem-3-carboxylate

The (E)-penem ester (87b) (45 mg) from Example 8(a) was hydrogenated as for Example 1(b) to give the title sodium salt (88b) (17mg, 53%) as a yellow freeze dried solid; $\lambda_{max}$ (H$_2$O) 285 nm (12,582); $\nu$max (KBr) 1751, 1604 br, 1554 br. cm$^{-1}$; δppm (D$_2$O) 4.13 (3H,s), 6.47 (1H,s), 6.90 (1H,s), 7.13 (1H,s), 8.69 (1H,s).

Preparation 9(a)

(3RS, 4SR) 1-t-Butyldimethylsilyl-3-(5-methyl-1,2,4-oxadiazol-3-yl-carbonyl)-4-tritylthioazetidin-2-one 1-t-Butyldimethylsilyl-4-tritylthioazetidin-2-one (1) (9.18 g) was reacted with ethyl 5-methyl-1,2,4-oxadiazole-3-carboxylate (3.76 g) (H. Hillman, H. Piechota and W. Schwiersh, Chem. Ber. 1961, 94, 757) using the method described in preparation 4(a) to give the title compound (89) (5.24 g, 47%), m.p. 156°–158° (plates ex ethyl acetate/hexane) $\nu_{max}$ (CHCl$_3$) 1725, 1705 cm$^{-1}$; δ(CDCl$_3$) (excluding Me$_2$Si groups which are obscured by T.M.S.) 0.98 (9H, s); 2.61 (3H, s); 4.57 (1H, d, J2 Hz), 4.98 (1H, d, J2 Hz), 7.02–7.69 (15H, m). (Found C, 67.1; H, 6.4; N, 7.4; S, 5.6; C$_{32}$H$_{35}$N$_3$O$_3$SSi required C, 67.4; H, 6.2; N, 7.3; S, 5.6%).

Preparation 9(b)

(3RS, 4SR)1-t-Butyldimethylsily-3-[hydroxy-(5-methyl-1,2,4-oxadiazol-3-yl)methyl]-4-tritylthioazetidin-2-one The ketone (89) (5.26 g) from Preparation 9(a) was treated as for Preparation (4b) to give two fractions. The less polar fraction contained a trans isomer (isomer A) of the title azetidinone (90) (2.23 g, 42%) $\nu_{max}$ (CH$_2$Cl$_2$) 3650–3140; 1720 cm$^{-1}$; δ(CDCl$_3$) (excluding MeSi groups obscured by T.M.S.) 0.90 (9H, s); 2.17–2.45 (1H, b. exch); 2.48 (3H, s); 3.5–3.83 (2H, m. sharpens on D$_2$O exch); 4.51 (1H, d, J3 Hz) 7.01–7.55 (15H, m) (Found MH+ 572).] The more polar fraction contained the other trans isomer (isomer B) of the title azetidinone (90) (1.95 g, 37%); m.p. 108°14 110° (plates ex ethyl acetate/hexane) $\nu_{max}$ (CH$_2$Cl$_2$) 3600–3250, 1740 cm$^{-1}$ δ(CDCl$_3$) (excluding Me$_2$Si groups obscured by T.M.S.) 0.84 (9H, s); 2.45 (3H, s); 2.50–2.80 (1H, b. exch); 3.73 (1H, dd, J6H$_{3, 3}$ Hz) 3.94–4.15 (1H, b sharpens to d, J6 Hz on D$_2$O exch.) 4.Ig (1H, d. J3 Hz); 6.98–7.55 (15H, m).

Preparation 9(c)

(3RS, 4SR)
3-[Hydroxy(5-methyl-1,2,4-oxadiazol-3-yl)methyl]-4-tritylthioazetidin-2-one The alcohol (90) (isomer B) (1.83 g) from Preparation 9(b) was treated as for Preparation 2(b) to give the title azetidinone (91) (1.46 g, 100%) m.p. 196°–199° (needles ex chloroform/hexane); $\nu_{max}$ (KBr) 3201, 3084, 1758 cm$^{-1}$ $\delta$(CDCl$_3$) 2.71 (3H, s), 3.53 (1H, d, J5 Hz, exch.), 3.66 (1H, dd, J6,3 Hz) 4.24 (1H, bs), 4.68 (1H, d, J3 Hz); 5.26 (1H, dd, J5, 3 Hz, collapses to d, J3 Hz on D$_2$O exch.) 7.19–7.41 (15H, m). (Found MH+ 458).

Preparation 9(d)

(3RS, 4SR)
3-[Acetoxy(5-methyl-1,2,4-oxadiazol-3-yl)methyl]-4-tritylthioazetidin-2-one The alcohol (91) (1.00 g) from Preparation 9(c) was treated as for Preparaton 1(c) to give the title acetate (92) (690 mg, 63%) m.p. 152°–153° (needles ex Toluene/Hexane $\nu_{max}$ (CH$_2$Cl$_2$) 3400, 1780 cm$^{-1}$ $\delta$(CDCl$_3$) 2.12 (3H, s); 2.67 (3H, s); 3.79 (1H, dd, J7, 4 Hz); 4.34 (1H, bs); 4.70 (1H, d, J4 Hz); 6.27 (1H, d, J8 Hz); 7.26–7.58 (15H, m) (Found C, 67.5; H, 5.1; N, 8.6; S, 6.4; C$_{28}$H$_{24}$N$_3$O$_4$S required C, 67.5; H, 4.9; N, 8.6; S, 6.4%).

Preparation 9(e)

(3RS, 4SR)
3-[Acetoxy(5-methyl-1,2,4-oxadiazol-3-yl)methyl]-1-(1-p-nitrobenzyloxycarbonyl-1-triphenylphosphoranylidenemethyl)-4-tritylthioazetidin-2-one The acetate (92) (730 mg) from Preparation 9(d) was converted via the hydroxy esters (93), $\nu_{max}$ (CHCl$_3$) 3505, 1760 cm$^{-1}$; and the chloroesters (94), $\nu_{max}$ (CHCl$_3$) 1790 cm$^{-1}$; to the title phosphorane (95) (570 mg, 53%) $\nu_{max}$ (CHCl$_3$) 1725, 1605 cm$^{-1}$, using the methods described in Preparation 1(d).

Preparation 9(f)

(3RS, 4SR) Silver 3-[acetoxy(5-methyl-1,2,4-oxadiazol-3-yl)methyl]-1-(1-p-nitrobenzyloxycarbonyl-1-triphenyl-phosphoranylidenemethyl)-4-tritylthioazetidin-2-one-4-thiolate The phosphorane (95) (570 mg) from Preparaton 9(e) was treated as for Preparation 1(e) to give the title silver salt (96) (511 mg, 91%).

Preparation 9(g)

(5RS, 6SR) p-Nitrobenzyl 6-[acetoxy(5-methyl-1,2,4-oxadiazol-3-yl)methyl]-penem-3-carboxylate The silver salt (96) (511 mg) from Preparation 9(f) was treated as for Preparation 1(f) to give the title penem (97) (53 mg, 66%) m.p. 147°–9° (plates ex ethyl acetate/hexane $\lambda_{max}$ (2% CHCl$_3$/EtOH) 314 nm (Em 7646), 260 nm (Em 13128). $\lambda_{max}$ (KBr) 1789, 1753, 1715 cm$^{-1}$; 6(CDCl$_3$) 2.1 (3H, s), 2.61 (3H, s); 4.46 (1H, d,d,d, J3.8 Hz, 2.2 Hz, 0.8 Hz); 5.27 and 5.41 (2H, ABq, J13.5); 5.98 (1H, d, J1.9 Hz); 6.37 (1H, d, J3.7); 7.52 (1H, d, J0.8); 7.58 (2H, d, J8.8 Hz); 8.23 (2H, d, J8.7). (Found C, 49.5; H, 3.4; N, 12.1; S, 6.7; C$_{19}$H$_{26}$N$_4$O$_8$S required C, 49.6; H, 3.5; N, 12.2; S, 7.0).

EXAMPLE 9(a)

(5RS) p-Nitrobenzyl (Z)-6-(5-methyl-1,2,4-oxadiazol-3-ylmethylene)penem-3-carboxylate The penem (97) (115 mg) from Preparation 9(g) was treated as for Example 1(a) to give the title penem (98) (99 mg, 100%) m.p. 165°–8° (microneedles ex ethyl acetate/hexane). $\lambda_{max}$ (2% CHCl$_3$/ EtOH) 303 nm (Em 10915), 243 nm (Em 22954) $\delta$(CDCl$_3$) 2.64 (3H, s); 5.29 and 5.44 (2H, Abq, J13.5 Hz)+6.58 (1H, d, J6.9 Hz); 7.10 (1H, d, J1.1Hz); 7.40 (1H, s); 7.61 (2H, d, J8.6 Hz); 8.23 (2H, d, J8.8 Hz). (Found C, 51.0; H, 3.1; N, 13.8; S, 7.8. C17H13N4O6S requires C, 50.9; H, 3.3; N, 14.0; S, 8.0%).

EXAMPLE 9(b)

(5RS) Sodium (Z)-6-(5-methyl-1,2,4-oxadiazol-3-yl-methylene)penem-3-carboxylate.

The penem ester (98) (30 mg) from Example 9(a) was hydrogenated as for Example 1(b) to give the title sodium salt (99) (10 mg, 48%) as an orange freeze-dried solid, $\lambda_{max}$ (H$_2$O) 290 nm (Em 5,300), 240 (14,400); $\delta$(D$_2$O) 2.63 (3H, s); 6.62 (1H, d, J0.6 Hz); 7.11 (1H, s); 7.14 (1H, d, J0.7 Hz).

Preparation 10(a)

Ethyl 1,2,4-triazole-3-carboxylate hydrochloride 1,2,4-Triazole-3-carboxylate (16 g) [G. I. Chipen and V. Ya. Grinshtein, Chem. Heterocyclic Compd. (U.S.S.R), 1,420 (1965)] dissolved in ethanol (400 ml) was saturated with HCl gas. Ice-bath cooling was applied to avoid overheating during saturation and the reaction was left stirring for three days. The product which had precipitated out was filtered off and washed with cold ethanol and then diethyl ether before being dried under vacuum giving 12 g of the product, 48% yield. $\nu_{max}$ (Nujol Mull) 1754 cm$^{-1}$.

Preparation 10(b)

Ethyl 1-methyl-1,2,4-triazole-3-carboxylate

An ethanolic (30 ml) solution of the hydrochloride from Preparation 10(a) (10 g) was added portion-wise to an ethanolic solution of sodium metal (2.6 g). The reaction was stirred for 1 hour after which methyl iodide was added (16 g). The reaction was left stirring for 24 hours after which it was evaporated and taken up into warm ethanol and 50% distilled water added before it was passed down an Amberlite IRA-410 (Cl) column. The fractions were combined and evaporated. The residue was extracted with hot ethyl acetate and filtered. The desired product crytallised out from ethyl acetate giving 4.3 g, 49% yield, m.p. 115° C. $\delta$ (CDCl$_3$) 1.43 (3H, t, J 7 Hz), 4.03 (3H, s), 4.43 (2H, q, J 7 Hz) and 8.19 (1H, s).

Preparation 10(c)

1-t-Butyldimethylsilyl-3-[(1-methyl-1,2,4-triazol-3-yl)carbonyl]-4-tritylthioazetidin-2-one 1-t-Butyldimethylsilyl-4-tritylthioazetidin-2-one (1) (10.74 g) was reacted with ethyl-1-methyl-1,2,4-triazole-3-carboxylate (2.79 g) in hot tetrahydrofuran (circa. 20 ml) using the method described in Preparation 4(a) to give the title compound (99a) 8.77 g, 66% yield, m.p. 180°–182° C., $\nu_{max}$ (Nujol Mull) 1751 and 1693 cm$^{-1}$; δ (CDCl$_3$) 0.33 (6H, s), 0.98 (9H, s), 3.81 (3H, s), 4.62 (1H, d, J2 Hz), 4.87 (1H, d, J2 Hz), 6.7–7.4 (15H, m), and 7.92 (1H, s).

Preparation 10(d)

1-t-Butyldimethylsilyl-3[(1-methyl-1,2,4-triazol-3-yl)hydroxymethyl]-4-tritylthioazetidin-2-one The ketone (99a) (8.8 g) from Preparation 10(c) was dissolved in aqueous dioxane and treated portionwise with NaBH$_4$ (2 g) over 2 hours. After 3 hours the reaction was diluted with ethyl acetate and washed with dilute acetic acid, brine, and saturated sodium hydrogen carbonate solution. Purification as for Example 3(b) gave the two trans isomers. The more polar isomer (Isomer A) of the title azetidinone (100) was isolated in 28% yield, 2.48 g, m.p. 152°–154° C. $\nu_{max}$ (KBr) 3,431, 1747 and 1725 cm$^{-1}$, δ(CDCl$_3$) SiMe$_3$ peaks obscured by locking signal, 0.78 (9H, s), 1.6–2.5 (1H, br.), 3.71–3.87 (4H, m), 4.14 (1H, br.d., J 6 Hz), 4.32 (1H, d, J2 Hz), 7.1–7.71 (15H, m) and 7.75 (1H, s). [Addition of D$_2$O caused the br.s. at δ1.6–2.5 to exchange and brd at δ4.4 to sharpen].

Preparation 10(e)

(3RS,4SR)-3[(1-methyl-1,2,4-triazol-3-yl)hydroxymethyl]-4-tritylthioazetidin-2-one The alcohol (100) (Isomer A) (2.23 g) from Preparation 10(d) was treated as for Preparation 2(b) to give the title azetidinone (101) 1.55 g, 87% yeild, m.p. 251° (decomp.) $\nu_{max}$ (KBr) 3,390 and 1761 cm$^{-1}$, δ(DMSO, d$_6$/D$_2$O) 3.55 (1H, dd, J3 and 4 Hz), 3.86 (3H, s), 4.41 (1H, d, J 3 Hz), 4.82 (1H, d, J 4 Hz), 7.06–7.46 (15H, br s) and 8.40 (1H, s).

Preparation 10(f)

(3RS,4SR)-3-[(1-methyl-1,2,4-triazol-3-yl)acetoxymethyl]-4-tritylthioazetidin-2-one The alcohol (101) (1.53 g) from Preparation 10(e) was suspended in dichloromethane and treated as for Preparation 1(c) with the exception that the reaction was allowed to proceed at ambient temperature for 2.75 hours and was chromatographed using methyl acetate as eluent. Thus the title azetidinone (102) was obtained as a crystalline solid 1.52 g, 91% yield, m.p. 172°–175° C. $\nu_{max}$ (Nujol Mull) 1781, 1760 and 1733 cm$^{-1}$, δ(CDCl$_3$) 2.09 (3H, s), 3.63–3.97 (4H, m), 4.1 (1H, br s), 4.6 (1H, d, J 3 Hz), 6.16 (1H, d, J 5 Hz), 6.9–7.5 (15H, m) and 7.94 (1H, s).

Preparation 10(g)

(3RS,4SR)-3-[Acetoxy(1-methyl-1,2,4-triazol-3-yl)methyl]-1(1-p-nitrobenzyloxycarbonyl-1-triphenylphosphoranylidenemethyl)-4-tritylthioazetidin-2-one The acetate (102) (1.42 g) from Preparation 10(f) was converted via the hydroxy esters (103), $\nu_{max}$ (CHCl$_3$) 1774 and 1750 sh cm$^{-1}$; and the chloroesters (104), to the title phosphorane (105) (2.1 g, 77% yield), $\nu_{max}$ (CHCl$_3$) 1750 and 1610 cm$^{-1}$ using the methods described in Preparation 1(d).

Preparation 10(h)

(3RS,4SR) Silver 3-[(1-methyl-1,2,4-triazol-3-yl)acetoxymethyl]-1-(1-p-nitrobenzyloxycarbonyl-1-triphenylphosphoranylidenemethyl)-4-tritylthioazetidin-2-one The phosphorane (105) (2.34 g) from Preparation 10(g) was treated as for Preparation 1(e) to give the title silver salt (106) 1.69 g, 84% yield.

Prepration 10(i)

(5RS,6SR) p-Nitrobenzyl 6-[(1-methyl-1,2,4-triazol-3-yl)acetoxymethyl]penem-3-carboxylate The silver salt (106) (1.69 g) from Preparation 10(h) was treated as for Preparation 1(f) to give the title penem (107) 0.78 g, 82% yield. m.p. 150° C. (decomp). λ$_{max}$ (EtOH) 262 (Em 14,068) and 316 nm (Em 9,317), $\nu_{max}$ (Nujol Mull) 1793, 1739 and 1705 cm$^{-1}$, δ (CDCl$_3$) 2.13 (3H, s) 3.88 (3H, s), 4.32–4.55 (1H, m), 5.20 and 5.47 (2H, ABq, J 16 Hz), 6.03 (1H, br.s), 6.36 (1H, d, J 4 Hz), 7.29 (1H, s) 7.3–8.16 (aromatics) and 8.23 (1H, s).

EXAMPLE 10(a)

(5RS) p-Nitrobenzyl (Z)-6-[(1-methyl-1,2,4-traizol-3-yl)methylene]penem-3-carboxylate The penem (107) (0.78 g) from Preparation 10(i) was treated with 1,8-diazabicyclo[5.4.0]undec-7-ene as for Example 1(a), but after 15 min at −40° the reaction was filtered. The product which had precipitated out was washed with cold dichloromethane and dried under vacuum giving the title penem (108) as a yellow solid 0.45 g, 66% yield. m.p. 197° (decomp.) λ$_{max}$ (CHCl$_3$EtOH) 272 (Em 21,426) and 311 nm (infl.) $\nu_{max}$ (KBr) 1781 and 1716 cm$^{-1}$, δ(CDCl$_3$) 3.97 (3H, s), 5.29 and 5.46 (2H, ABq, J 13.6 Hz), 6.58 (1H, d, J 0.98 Hz), 7.12 (1H, s), 7.38 (1H, s), 7.63 and 8.25 (4H, AA'BB', J 8.8 Hz) and 8.06 (1H, s).

EXAMPLE 10(b)

(5RS) Sodium (Z)-6[(1-methyl-1,2,4-triazol-3-yl)methylene]penem-3-carboxylate

The penem ester (108) (0.1 g) from Example 10(a) was hydrogenated as for Example 1(b) to give the title sodium salt (109) as a yellow freeze-dried solid 27 mg, 32% yield. λ$_{max}$ (H$_2$O) 274 (Em 11,154) and 375 nm (Em 1,029) $\nu_{max}$ (KBr) 1755 and 1600 cm$^{-1}$, δ(D$_2$O) 3.95 (3H, s), 6.59 (1H, s), 7.06 (1H, s), 7.1 (1H, s) and 8.39 (1H, s).

Preparation 11(a)

(3RS, 4SR) 3-[Acetoxy(1-methylpyrazol-4-yl)methyl]-4-(t-butyldiphenylsilyloxyacetylthio)-1-(1-p-nitrobenzyloxycarbonyl-1-triphenylphosphoranylidenemethyl)azetidin-2-one.

The silver salt (18) (0.400 g) from Preparation 2(e) was suspended in dry dichloromethane (25 ml) and cooled in an ice-bath, with stirring. Pyridine (114 μl) was added, followed by a solution of t-butyldiphenylsilyloxyacetyl chloride (0.509 g) (EP 0 120 613 A, Beecham) in dry dichloromethane (5 ml). Stirring was continued at ice-bath temperature for 20 min. The resulting suspension was filtered through Kieselguhr, washing well with ethyl acetate. The filtrate was washed with 1N hydrochloric acid, brine, saturated sodium hydrogen carbonate solution, brine and dried over $MgSO_4$. The solvent was evaporated at reduced pressure and the residue chromatographed over silica gel (10 g). Elution with a gradient of 50–100% ethyl acetate/hexane gave the title compound (110) as a colourless oil (0.228 g); $\nu_{max}$ ($CH_2Cl_2$) 1760, 1695, 1625, 1608 cm$^{-1}$.

Preparation 11(b)

(5RS, 6SR) p-Nitrobenzyl 6-[acetoxy (1-methylpyrazol-4-yl) methyl]-2-(t-butyldiphenylsilyloxymethyl)penem-3-carboxylate The phosphorane (110) (0.228 g) from Preparation 11(a) was dissolved in dry toluene (100 ml) and refluxed for 2.5 h, under an atmosphere of argon. After cooling, the solvent was evaporated at reduced pressure and the residue chromatographed over silica gel (6 g). Elution with 50% ethyl acetate/hexane afforded the title compound (111) (0.142 g) as a colourless oil; $\nu_{max}$ ($CH_2Cl_2$) 1792, 1735, 1712, 1608 cm$^{-1}$.

Preparation 11(c)

(5RS, 6SR) p-Nitrobenzyl 6-[acetoxy(1-methylpyrazol-4-yl)methyl]-2-(hydroxyethyl)penem-3-carboxylate The t-butyldiphenylsilyl ether (111) (0.142 g) from Preparation 11(b) was dissolved in dry tetrahydrofuran (25 ml) and cooled in an ice bath, with stirring. Glacial acetic acid (35 mg) and tetra-n-butyl ammonium fluoride (255 μl of a 1M solution in tetrahydrofuran) were added and the solution stirred at ice bath temperature for 30 min. Ethyl acetate was added and the organic solution was washed with brine, saturated sodium hydrogen carbonate solution, brine and dried over $MgSO_4$. The solvent was removed by evaporation at reduced pressure and the residue applied to a column of silica gel (6 g). Elution with a gradient of 75–100% ethyl acetate/hexane afforded the title compound (112) as a white solid (0.074 g) after trituration with diethyl ether; $\lambda_{max}$ ($CH_3CN$) 318 nm ($\epsilon$8581), 265 nm ($\epsilon$10858), $\nu_{max}$ $_{(KBr)}$ 1784, 1726, 1700, 1604, 1573, 1522 cm$^{-1}$, δH (d-DMF) 2.06 (3H, s, COMe , 3.88 (s, NMe, 4.54 (1H, dd, J1.9 and 5.9 Hz, 6-$\underline{H}$), 4.77 (2H, broad s, $CH_2OH$), 5.35 (1H, d, J14.2 Hz, $\overline{CO_2CHa}$), 5.49 (1H, d, J $\overline{14.1}$ Hz, $CO_2CH_b$), 5.74 (1H, d, J $1.\overline{7}$ Hz, 5-H), 6.08 (1H, broad res., $O\underline{H}$), 6.21 (1H, d, J 5.9 Hz, 8-H), 7.56 (1H, s, pyrazole-$\underline{H}$), 7.78 (2H, d, J 8.7 Hz, aromatic $\underline{H}$), 7.86 (1H, s, pyrazole-$\underline{H}$), 8.29 (2H, d, J 8,8 Hz, aromatic $\underline{H}$).

EXAMPLE 11(a)

(5RS) p-Nitrobenzyl 2-hydroxymethyl-6(Z)-[(1-methylpyrazol-4-yl)methylene]penem-3-carboxylate.

The penem (112) (0.069 gm) from Preparation 11(c) was dissolved in dry tetrahydrofuran (100 ml) and cooled to −40° C., under an atmosphere of argon, with stirring. A solution of 1,8-diazabicyclo[5.4.0]undec-7-ene (0.054 g) in dry tetrahydrofuran (5 ml) was added dropwise and stirring was continued at this temperature for 30 min. Ethyl acetate was then added and the solution washed with 5% citric acid solution, brine, saturated sodium hydrogen carbonate solution, brine and dried over $MgSO_4$. The solvent was evaporated at reduced pressure and the residue applied to a column of silica gel (4 g). Elution with a gradient of 0–50% ethyl acetate/dichloromethane yielded the title compound (113) as a pale yellow solid (0.037 g) after trituration with diethyl ether; $\lambda_{max}$ ($CH_3CN$) 300 nm ($\epsilon$33099), $\nu_{max}$ (KBr) 3311, 1772, 1701, 1682, 1604, 1568, 1550, 1516 cm$^{-1}$, δH(d-DMF) 3.97 (3H, s, NMe), 4.78 (2H, ABq, $CH_2OH$), 5.38 (1H, d, J14.0 Hz, $CO_2C\underline{H}a$), 5.54 (1H, d, J 14.0 Hz, $CO_2CHb$), 6.05 (1H, broad res., $O\underline{H}$), 6.67 (1H, d, J 0.8 Hz, 5-$\overline{\underline{H}}$), 7.28 (1H, s, vinylic $\underline{H}$), $7.\overline{80}$ (1H, s, pyrazole-$\underline{H}$), 7.84 (2H, d, J 8.7 Hz, aromatic $\underline{H}$), 8.17 (1H, s, pyrazole-$\underline{H}$), 8.30 (2H, d, J 8.7 Hz, aromatic $\underline{H}$). (Found: M+$42\overline{8}$.0793. $C_{19}H_{16}N_4O_6S$ requires $4\overline{28}.0791$).

EXAMPLE 11(b)

Sodium (5RS)-2- ethyl-6(Z)-[(1-methylpyrazol-4-yl) methylene]penem-3-carboxylate The ester (113) (0.020 g) from Example 11(a) was dissolved in 30% aqueous 1,4-dioxan (15 ml) and shaken for 1 h at atmospheric pressure and room temperature with hydrogen in the presence of 5% palladium on carbon catalyst (0.040 g). The suspension was then filtered through Kieselguhr, washing well with water. The filtrate was concentrated to small volume at reduced pressure and applied to a column of Biogel P-2, which was eluted with water. The fractions were monitored by u.v. and those containing the product were combined. Lyophilisation of the resulting solution afforded the title compound (114) as a pale yellow solid (0.011 g), $\lambda_{max}$ ($H_2O$) 295 nm ($\epsilon$21,563), $\nu_{max}$ (KBr) 3217, 1746, 1677, 1603, 1580, 1551 cm$^{-1}$ δH ($D_2O$) 3.90 (3H, s, (3H, s, NMe), 4.52 (1H, d, J 15.0Hz, $CH_aOH$), 4.75 (1H, d, $CH_bOH$), 6.41 (1H, s, 5-$\underline{H}$), 7.16 $\overline{(1H,}$ s, vinylic $\underline{H}$), 7.67 (1H, s, pyrazole-$\underline{H}$), $\overline{7.83}$ (1H, s, pyrazole -$\underline{H}$).

Preparation 12(a)

(3RS, 4SR) 3-[Acetoxy-(1-methylpyrazol-4-yl)methyl]-4-[(ethylthio)thiocarbonylthio]-1-(1-p-nitrobenzyloxycarbonyl-1-triphenylphosphoranylidenemethyl)azetidin-2-one The silver salt (18) (1.10 g) from Preparation 2(e) was suspended in dry dichloromethane (100 ml) and cooled in an ice bath. Pyridine (0.315 ml) was added to the stirred suspension, followed by a solution of ethyl dithiochloroformate (0.393 g) in dichloromethane (5 ml). The resulting solution was stirred at room temperature for 1 h and then filtered through Kieselguhr. The filtrate was washed with 5% citric acid solution, saturated sodium hydrogen carbonate solution, brine, and dried over $MgSO_4$. The solvent was evaporated at reduced pressure and the residue chromatographed over silica gel (30 g). Elution with a gradient of 50–100% ethyl acetate/hexane afforded the title compound (115) as a pale yellow foam (0.810 g); $\nu_{max}$ ($CH_2Cl_2$) 1762, 1738 (shoulder), 1623, 1608, 1520 cm$^{-1}$.

Preparation 12(b)

(5RS, 6SR) and (5RS, 6RS) p-Nitrobenzyl 6-[acetoxy(1-methylpyrazol-4-yl)methyl]-2-ethylthiopenem-3-carboxylate The phosphorane (115) (0.810 g) from Preparation 12(a) was dissolved in dry xylene (800 ml) and heated to reflux for 11 h, under an atmosphere of argon, in the presence of hydroquinone (0.060 g). After cooling, the solvent was evaporated at reduced pressure and the crude product chromatographed over silica gel (30 g). Elution with 75% ethyl acetate/hexane provided the slightly impure product as a pale yellow oil (0.310 g). This was re-chromatographed over silica gel (15 g). Elution with a gradient of 0-°% ethyl acetate/dichloromethane afforded the title compound (116) (0.261 g) as a mixture of (5RS, 6SR) and (5RS, 6RS) diastereoisomers in the approximate ratio of 3:1 (by nmr); $\lambda_{max}$ (EtOH) 337, 260 nm, $\nu_{max}$ (CH$_2$Cl$_2$) 1792, 1740, 1695, 1605, 1521 cm$^{-1}$, $\delta$H (CDCl$_3$) inter alia 1.39 (3H, t, CH$_2$CH$_3$), 2.05 (minor) and 2.08 (major isomer) (3H, s, COCH$_3$), 3.88 (major isomer) and 3.91 (minor isomer) (3H, s, NCH$_3$), 4.23 (dd, J 1.5 and 6.6 Hz, 6-H of major isomer) and 4.51 (dd, J 4.0 and 11.1 Hz, 6-H of minor isomer) (1H), 5.24 (1H, d, CO$_2$CHHD a), 5.44 (1H, d, CO$_2$CH$_b$), 5.65 (d, J 1.4 Hz, 5-H of major isomer) and 5.82 (d, J 3.9 Hz, 5-H of minor isomer) (1H), 6.18–6.24 (1H, two d, 8-H of major and minor isomers), 7.4–7.7 (4H, m, pyrazole and aromatic H), 8.22 (2H, d, J 8.8 Hz, aromatic H).

EXAMPLE 12(a)

(5RS) p-Nitrobenzyl 2-ethylthio-6-(Z)-[(1-methylpyrazol-4-yl)methylene]-penem-3-carboxylate The penem (116) (0.060 g) from Preparation 12(b) was converted to the title compound (117) by the procedure described in Example 11(a). The product was obtained as a yellow solid (0.026 g) after trituration with ethyl acetate; $\lambda_{max}$ (EtOH) 299 nm ($\epsilon$ 28253), $\nu_{max}$ (KBr) 1772, 1669, 1604, 1548, 1508 cm$^{-1}$, $\delta$H (CDCl$_3$) 1.38 (3H, t, J 7.4 Hz, CH$_2$CH$_3$), 2.85–3.12 (2H, m, SCH$_2$), 3.97 (3H, s, NCH$_3$), 5.26 (1H, d, J 13.8 Hz, CO$_2$CHa), 5.51 (1H,d, J 13.8 Hz, CO$_2$CHHD b), 6.35 (1H, d, J 1.0 Hz, 5-H), 7.07 (1H, s, vinylic H), 7.51 (2H, s, pyrazole H), 7.67 (2H, d, J8.9 Hz, aromatic H), 8.23 (2H, d, J 8.9 Hz, aromatic H).

EXAMPLE 12(b)

Sodium (5RS)-2-ethylthio-6(Z)-[(1-methylpyrazol-4-yl)methylene]penem-3-carboxylate Hydrogenolysis of the ester (117) (0.020 g) from Example 12(a) by the procedure described in Example 11(b) afforded the title compound (118) (0.009 g) as a pale yellow fluffy solid after Biogel P-2 column chromatography and lyophilisation; $\lambda_{max}$ (H$_2$O) 296 nm ($\epsilon$ 18,728), $\nu_{max}$ (KBr) 1761, 1675 and 1550 cm$^{-1}$, $\delta$H (D$_2$O) 1.30 (3H, t, J 7.4 Hz, SCH$_2$CH$_3$), 2.75–3.05 (2H, m, SCH$_2$CH$_3$), 3.89 (3H, s, NMe), 6.43 (1H, s, 5-H), 7.13 (1H, s, vinylic-H), 7.65 (1H, s, pyrazole-H), 7.82 (1H, s, pyrazole-H).

Preparation 13(a)

(5RS, 6SR) and (5RS, 6RS) p-Nitrobenzyl 6-[Acetoxy(1-methyl-pyrazol-4-yl)methyl]-2-ethylsulphinylpenem-3-carboxylate.

The mixture of diastereoisomers from Preparation 12(b) (0.200 g) was dissolved in dichloromethane (20 ml) and layered with saturated sodium hydrogen carbonate solution (20 ml). The resulting two-phase solution was cooled in an ice bath. A solution of m-chloroperbenzoic acid (0.092 g) in dichloromethane (5 ml) was then added to the vigorously stirred solution. Stirring was continued at ice-bath temperature for 15 minutes. The organic layer was then separated, washed with brine and dried over MgSO$_4$. The solvent was evaporated at reduced pressure and the residue chromatographed over silica gel (2 g). Elution with a gradient of 0–50% ethyl acetate/dichloromethane afforded the isomeric mixture of sulphoxides (119) as a white foam (0.100 g); $\nu_{max}$ (CH$_2$Cl$_2$) 1801, 1740, 1708, 1610 cm$^{-1}$.

Preparation 13(b)

(5RS, 6SR) and (5RS, 6RS) p-Nitrobenzyl 6-[acetoxy(1-methylpyrazol-4-yl)methyl]-2-(2-hydroxyethylthio)penem-3-carboxylate.

The mixture of sulphoxides (119) (0.100 g) obtained from Preparation 13(a) and 2-mercaptoethanol (0.031 gm) were dissolved in dry acetonitrile (10 ml) and cooled to −40° C., under an atmosphere of argon. A solution of diisopropylethylamine (0.026 g) in acetonitrile (2 ml) was added to the stirred solution and stirring was continued at −40° C. for 30 min. Ethyl acetate was then added and the organic solution washed with 5% citric acid solution, saturated sodium hydrogen carbonate solution, brine and dried over MgSO$_4$. The solvent was evaporated at reduced pressure and the residue chromatographed over silica gel (2 g). Elution with a gradient of 0–50% ethyl acetate/dichloromethane gave the title compound (120) (0.080 g) as a mixture of (5RS, 6SR) and (5RS, 6RS) isomers in the approximate ratio of 5:2 (by nmr); $\nu_{max}$ (CH$_2$Cl$_2$) 3600, 1798, 1741, 1698, 1609, 1527 cm$^{-1}$, $\delta$H (CDCl$_3$) inter alia 2.05 (s, COMe of minor isomer) and 2.07 (s, COMe of major isomer ) (3H), 3.05–3.35 (2H, m, SCH$_2$), 3.8–4.0 (5H, m, CH$_2$OH+NMe), 4.24 ,(dd, J 1.3 and 6.5 Hz, 6-H of major isomer) and 4.52 (dd, J 3.9 and 11.0 Hz, 6-H of minor isomer) (1H), 5.23 (1H, d, J 13.6 Hz, CO$_2$CHa), 5.44 (1H, d, J13.8 Hz, CP$_2$CHHD b), 5.65 (d, J 1.3 Hz, 5-H of major isomer) and 5.82 (d, J 3.6 Hz, 5-H of minor isomer) (1H), 6.19 (d, J 6.4 Hz, 8-H of major isomer) and 6.20 (d, J 11.1 Hz, 8-H of minor isomer) (1H), 7.4–7.7 (4H, m, pyrazole-H+aromatic-H), 8.22 (2H, d, J 8.5 Hz, aromatic-H).

EXAMPLE 13(a)

p-Nitrobenzyl (5RS)-2-(2-hydroxyethylthio)-6(Z)-[(1-methylpyrazol-4-yl)methylene]penem-3-carboxylate Reaction of the isomeric mixture (120) (0.072 g) from Preparation 13(b) with 1,8-diazabicyclo[5.4.0]undec-7-ene, by the procedure described in Example 11(a),afforded the title compound (121) as a yellow solid (0.019 g) after trituration with ethyl acetate; $\lambda_{max}$ (EtOH) 298 nm ($\epsilon$24,293), $\nu_{max}$ (KBr) 3360, 1790, 1770, 1674, 1604, 1549, 1509 cm$^{-1}$, $\epsilon$H (CDCl$_3$) 1.95 (1H, t, OH), 3.05–3.28 (2H, overlapping tq, SCH$_2$), 3.87 (2H, q, CH$_2$OH), 3.97 (3H, s, NMe), 5.27 (1H, d, J 13.8 Hz, CO$_2$CHa), 5.51 (1H, d, J 13.9 Hz, CO$_2$CHHD b), 6.35 (1H, d, J 1.0 Hz, 5-H), 7.08 (1H, s, vinylic-H), 7.50 (2H, two s, pyrazole protons), 7.67 (2H, d, J 8.9 Hz, aromatic H), 8.23 (2H, d, J 8.7 Hz, aromatic H).

13(b)

EXAMPLE 13(b)

Sodium (5RS)-2-(2-hydroxyethylthio)-6(Z)-[(1-methylpyrazol-4-yl)methylene]penem-3-carboxylate.

Hydrogenolysis of the ester (121) (0.014 g) from Example 13(a) by the procedure described in Example 11(b) afforded the title compound (122) (0.008 gm) as a pale yellow fluffy solid after Biogel P-2 column chromatography and lyophilisation; $\lambda_{max}$ (H$_2$O) 298 nm ($\epsilon$ 18,635), $\nu_{max}$ (KBr) 1761, 1676 and 1552 cm$^{-1}$, $\delta$H (D$_2$O) 3.04 (2H, overlapping tq, SCH$_2$), 3.79 (2H, t, CH$_2$CH$_2$OH), 3.88 (3H, s, NMe), 6.43 (1H, s, 5-H), 7.13 (1H, s, vinylic-H), 7.64 (1H, s, pyrazole-H), 7.81 (1H, s, pyrazole-H).

Preparation (14a)

(3RS, 4SR) 1-t-Butyldimethylsilyl-3-(N-methyltetrazolecarbonyl)-4-tritylthioazetidin-2-one 1-t-Butyldimethylsilyl-4-tritylthioazetidin-2-one (1) (9.18 g, 20 mmol) was reacted with an approximately 1:1 mixture of ethyl 1- and 2-methyltetrazole-5-carboxylate (3.94 g, 24.8 mmol) (prepared by treating ethyl tetrazole-5-carboxylate [D. Moderhack, *Chem. Ber.*, 1975, 108, 887] with excess diazomethane [cf O. Gryszkiewicz-Trochimourski, *Compt. Rendu*, 1958, 246, 2627]) using the method described in Preparation 4(a). The crude reaction mixture was chromatographed on silica eluting with ethyl acetate/hexane mixtures to give two fractions. The less polar fraction contained a regioisomer of the title azetidinone (123) (3.48 g, 30%) $\nu_{max}$ (CH$_2$Cl$_2$) 1750, 1690 cm$^{-1}$; $\delta$(CDCl$_3$) 0.34 (6H, s), 1.00 (9H, s), 4.10 (3H, s), 4.90 (2H, s), 6.77-7.50 (15H, m); The more polar fraction contained the other regioisomer of the title compound (124) (3.5g, 30%) (mp. 158°-161°, needles ex ether/hexane) $\nu_{max}$ (CH$_2$Cl$_2$) 1750, 1700 cm$^{-1}$; $\delta$(CDCl$_3$) 0.37 (6H, s), 1.00 (9H, s), 4.37 (3H, s), 4.57 (1H, d, J2 Hz), 4.97 (1H, d, J2 Hz), 6.80-7.60 (15H, m). (Found C, 65.3; H; 6.3; N, 12.2; S, 5.6. C$_{31}$H$_{35}$N$_5$O$_2$SSi requires C, 65.4; H, 6.2; N, 12.3; S, 5.6%).

Preparation 14(b)

(3RS, 4SR) 1-t-Butyldimethylsilyl-3-[hydroxy(N-methyltetrazol-5-yl)methyl]-4-tritylthioazetidin-2-one The ketone (124) (4.13 g, 7.26 mmol) from Preparation 14(a) in dimethoxyethane (50 ml) at $-30°$ under argon was treated with sodium borohydride (103 mg, 2.72 mmol). After 15 minutes a further amount of sodium borohydride (17 mg) was added. After a further 15 minutes the reaction was worked up as in Preparation 4(b). Chromatography on silica eluting with dichloromethane and dichloromethane/ethyl acetate mixtures gave two fractions. The less polar fraction contained a trans isomer (isomer A) of the title azetidinone (125) (2.10 g, 51%) $\nu_{max}$ (CH$_2$Cl$_2$) 3600-3400, 1750 cm$^{-1}$; $\delta$(CDCl$_3$) 0.25 (3H, s), 0.28 (3H, s), 0.93 (9H, s), 2.47 (1H, d, J 6.3 Hz, exch), 3.70-3.82 (2H, m, sharpens on exch.). 4.29 (3H, s), 4.60 (1H, d, J 1.8 Hz), 7.14-7.53 (15H, m). (Found MH$^+$572) The more polar fraction contained the other trans isomer (isomer B) of the title azetidinone (125), (1.75 g, 42%); mp 159°-160° (plates from ether/hexane ; $\nu_{max}$ (CH$_2$Cl$_2$) 3600-3400, 1745 cm$^{-1}$; (Found C, 65.3; H, 6.7; N, 12.2; S; 5.5. C$_{31}$H$_{37}$N$_5$O$_2$SSi requires C, 65.1; H, 6.5; N, 12.3; S, 5.6%).

Preparation 14(c)

(3RS, 4SR) 3-[Hydroxy(N-methyltetrazol-5-yl)methyl]-4-tritylthioazetidin-2-one The alcohol (125) (Isomer B) (1.89 g, 3.31 mmol) from Preparation 14(b) was treated as for Preparation 2(b) to give the title azetidinone (126) (1.39 g, 92%); $\nu_{max}$ (CH$_2$Cl$_2$) 3600-3300, 1765 cm$^{-1}$; $\delta$(CDCl$_3$) 3.25 (1H, d, J 5.1Hz), 3.72 (1H, dd, J3.1, 3.1Hz), 4.24 (1H, bs), 4.47 (3H, s), 4.72 (1H, d, J2.7 Hz), 5.45 (1H, dd, J3.7, 5.0 Hz), 7.20-7.41 (15H, m); (Found MH$^+$458).

Preparation 14(d)

(3RS, 4SR) 3-[Acetoxy(N-methyltetrazol-5-yl)methyl]-4-tritylthioazetidin-2-one The alcohol (126) (1.4 g) from Preparation 14(c) was treated as for Preparation 1(c) to give the title acetate (127) (1.46g, 95%); $\nu_{max}$ (CH$_2$Cl$_2$) 3400, 1775, 1760 (sh) cm$^{-1}$; $\delta$(CDCl$_3$) 2.12 (3H, s), 3.78 (1H, dd, J2.8, 5.3 Hz), 4.17 (1H, bs), 4.43 (3H, s), 4.71 (1H, d, J2.8 Hz), 6.39 (1H, d, J5.3 Hz), 7.15-7.48 (15H, m). (Found MH$^+$500).

Preparation 14(e)

(3RS, 4SR) 3-[Acetoxy(N-methyltetrazol-5-yl)methyl[-1-(1-p-nitrobenzyloxycarbonyl-1-triphenylphosphoranylidenemethyl)-4-tritylthioazetidin-2-one The acetate (127) (1.36 g) from Preparation 14(d) was converted via the hydroxyesters (128) $\nu_{max}$ (CH$_2$Cl$_2$) 3500, 1780, 1750 cm$^{-1}$; and the chloroesters (129) $\nu_{max}$ (CH$_2$Cl$_2$) 1790, 1760 cm$^{-1}$ to the phosphorane (130) (2.00 g, 77%) $\nu_{max}$(CH$_2$Cl$_2$) 1755, 1620 cm$^{-1}$, using the methods described in Preparation 1(d).

Preparation 14(f)

(3RS, 4SR) Silver 3-[Acetoxy(N-methyltetrazol-5-yl)methyl]-1-(1-p-nitrobenzyloxycarbonyl-1-triph-enylphoshoranylidenemethyl)azetidin-2-one-4-thiolate The phosphorane (130) (1.8 g) from Preparation 14(e) was treated with silver nitrate/pyridine as for Preparation 1(e) to give the title silver salt (131) (1.35 g, 87%) as an off-white solid.

Preparation 14(g)

(5RS, 6SR) p-Nitrobenzyl 6-[acetoxy(N-methyltetrazol-5-yl) methyl]penem-3-carboxylate The silver salt (131) (1.35 g) from Preparation 14(f) was treated as for preparation 1(f) to give the title penem (132) (631 mg, 83%); $\nu_{max}$ (CH$_2$Cl$_2$) 1795, 1750, 1720 cm$^{-1}$; $\delta$(CDCl$_3$) 2.16 (3H, s), 4.38 (3H, s), 4.53 (1H, ddd, J 1.1, 2.1, 3.8 Hz), 5.28 and 5.43 (2H, ABq, J13.6 Hz), 6.06 (1H, d, J2.2 Hz), 6.55 (1H, d, J3.8 Hz), 7.34 (1H, d, J1.1Hz), 7.59 (2H, d, J8.8 Hz), 8.24 (2H, d, J8.7 Hz),

EXAMPLE 14(a)

(5RS) p-Nitrobenzyl (Z)-6-(N-methyltetrazol-5-ylmethylene) penem-3-carboxylate.

The penem (132) (70 mg) from Preparation 14(g) was treated as for Example 1(a) to give the title penem (133) (51 mg, 84%), $\nu_{max}$ (CH$_2$Cl$_2$) 1785, 1615 cm$^{-1}$; $\delta$(CDCl$_3$) 4.41 (3H, s), 5.30 and 5.46 (2H, ABq, J13.5 Hz), 6.60 (1H, d, J1.1 Hz), 7.26 (s-obscurred by solvent peak), 7.41 (1H, s), 7.62 (2H, d, J8.8 Hz), 8.25 (2H, d, J8.8 Hz).

EXAMPLE 14(b)

(5RS) Sodium (Z)-6-(N-methyltetrazol-5-ylmethylene)penem-3-carboxylate

The (Z)-penem ester (133) (50 mg) from Example 14(a) was hydrogenated as for Example 1(b) to give the title sodium salt (134) (13 mg, 36%) as a yellow freeze-dried solid; $\lambda_{max}$ (H$_2$O) 254 nm (∈m 9495); $\delta$(D$_2$O) 4.41 (3H, s), 6.62 (1H, d, J0.9 Hz), 7.10 (1H, s), 7.32 (1H, bs).

Preparation 15(a)

(3RS, 4SR) 1-t-Butyldimethylsilyl-3-[hydroxy(N-methyltetrazol-5-yl)methyl]-4-tritylthioazetidin-2-one The ketone (123) (5.15 g) from Preparation 14(a) was treated as for Preparation 14(b) to give two fractions. The less polar fraction contained a trans isomer (isomer A) of the title azetidinone (135) (0.97 g, 19%); $\nu_{max}$ (CH$_2$Cl$_2$) 3600–3300, 1745 cm$^{-1}$. The more polar fraction contained the other trans isomer (isomer B) of the title azetidinone (2.23g, 43%); $\nu_{max}$ (CH$_2$Cl$_2$) 3700–3300, 1740 cm$^{-1}$.

Preparation 15(b)

(3RS, 4SR) 3-[Hydroxy(N-methyltetrazol-5-yl)methyl]-4-tritylthioazetidin-2-one The alcohol (135) (isomer B) (2.78 g) from Preparation 15(a) was treated as for Preparation 2(b) to give the title azetidinone (136) (2.1 g, 97%); $\nu_{max}$ (CH$_2$Cl$_2$) 3600–3300, 1755 cm$^{-1}$.

Preparation 15(c)

(3RS, 4SR) 3-[Acetoxy(N-methyltetrazol-5-yl)methyl]-4-tritylthioazetidin-2-one The alcohol (136) (2.03 g) from Preparation 15(b) was treated as for Preparation 1(c) to give the title acetate (137) (2.11 g, 95%); $\nu_{max}$ (CH$_2$Cl$_2$) 3380, 1775 cm$^{-1}$, $\delta$(CDCl$_3$) 2.09 (3H, s), 3.60–3.80 (1H, m), 4.07 (3H, s), 4.30 (1H, bs), 4.83 (1H, d, J2.5 Hz), 6.11 (1H, d, J6.0Hz), 7.22–7.73 (15H, m).

Preparation 15(d)

(3RS, 4SR) 3-[Acetoxy(N methyltetrazol-5-yl)methyl]-1-(1-p-nitrobenzyloxycarbonyl-1-triphenylphosphoranylidenemethyl)-4-tritylthioazetidin-2-one The acetate (137) (2.00 G) from Preparation 15(c) was converted via the hydroxyesters (138 $\nu_{max}$ (CH$_2$Cl$_2$) 3600–3400, 1775, 1760 (sh) cm$^{-1}$, and the chloroesters (139), $\nu_{max}$(CH$_2$Cl$_2$) 1785, 1760 (sh) cm$^{-1}$; to the title phosphorane (140) (2.55 g, 67%), $\nu_{max}$ (CH$_2$Cl$_2$) 1755, 1620 cm$^{-1}$, using the methods described in Preparation 1(d).

Preparation 15(e)

(3RS, 4SR) Silver 3-[acetoxyl(N methyltetrazol-5-yl)methyl]-1-(1-p-nitrobenzyloxycarbonyl-1-triphenylphos.phoranylidene methyl)-4-tritylthioazetidin-2-one-4-thiolate The phosphorane (140) (1.53g) from Preparation 15(d) was treated as for Preparation 1(e) to give the title silver salt (141) (1.1 g, 85%).

Preparation 15(f)

(5RS, 6SR) p-Nitrobenzyl 6-[acetoxy(N-methyltetrazol-5-yl)methyl]penem-3-carboxylate The silver salt (141) (1.11 g) from Preparation 15(e) was treated as for Prepration 1(f) to give the title penem (142) (451 mg, 72%); $\nu_{max}$ (CH$_2$Cl$_2$) 1795, 1750, 1720 cm$^{-1}$.

EXAMPLE 15(a)

(5RS) p-Nitrobenzyl (Z)-6-(N-methyltetrazol-5-ylmethylene) penem-3-carboxylate The penem (142) (115 mg) from Preparation 15(f) was treated as for Example 1(a) to give the title penem (143) (85 mg, 85%), $\nu_{max}$ (CH$_2$Cl$_2$) 1785, 1720 cm$^{-1}$; $\delta$(CDCl$_3$) 4.17 (3H, s), 5.31 and 5.46 (2H, ABq, J 13.5 Hz), 6.63 (1H, d, J1.1 Hz), 7.04 (1H, d, J1.1Hz), 7.45 (1H, s), 7.62 (2H, d, J8.9 Hz), 8.25 (2H,dd, J8.8 Hz).

EXAMPLE 15(b)

(5RS) Sodium (Z)-6-(N-methyltetrazol-5-ylmethylene)penem-3-carboxylate

The (Z) penem ester (143) (80 mg) from Example 15(a) was hydrogenated as for Example 1(b) to give the title sodium salt (144) (31 mg, 54%) as an orange amorphous solid; $\lambda_{max}$ (H$_2$O) 253 nm (∈m 13,910), 370 (940); $\delta$(D$_2$O) 4.16(3H, s), 6.61 (1H, s), 7.10 (1H, s), 7.32 (1H, s).

Preparation 16(a)

Ethyl 1-methyl-1,2,3-triazole-4-carboxylate

A solution of ethyl propiolate (16.2 ml) in hexane (50 ml) was added, dropwise over 30 minutes with stirring, to ice-salt bath cooled methyl azide [prepared by addition of dimethyl sulphate (18.9 ml) to a stirred solution of sodium azide (13 g) in 1N sodium hydroxide (100 ml) at 70° C. according to the method of O. Dimroth, Chem. Ber., 1905, 38, 1573]. The stirred mixture was allowed to attain room temperature during 2 hours and stood for a further 20 hours. The hexane liquors were decanted from the crystalline product which was washed with hexane (3×10 ml) and dried under vacuum to give the title ester (145) 39 g), m.p. 90°–91° C. (colourless needles), $\nu_{max}$ (CHCl$_3$) 1720 cm$^{-1}$; 4ppm (CDCl$_3$) 1.40 (3H, t, J7 Hz), 4.20 (3H, s), 4.44 (2H, q, J7 Hz), 8.18 (1H, s). (Found: C, 46.4; H, 5.8; N, 27.0. C$_6$H$_9$N$_3$O$_2$ requires C, 46.4; H, 5.8; N, 27.1%).

The combined hexane liquors and washings were kept at room temperature for a further 9 days when a second crop of the title ester (145) (6.98 g), mp 90°–91° C. was obtained after decanting, washing with hexane (3×20 ml) and drying under vacuum.

Preparation 16(b)

(3S, 4R) 3-Bromo-1-t-butyldimethylsilyl-4-tritylthioazetidin-2-one

A solution of triethylamine (116 mg) in dry dimethylformamide (1 ml) was added, dropwise over 1½ minute, to a stirred solution of (3S, 4R) 3-bromo-4-tritylthioazetidin-2-one (424 mg) (A. Martel et al., Can. J. Chem., 1983, 61, 1899) and t-butyldimethylchorosilane (188 mg) in dry dimethylformamide (4 ml) at ice-bath temperature. The mixture was stirred at room temperature overnight, diluted with ethyl acetate (30 ml), and washed with 5% citric acid (2 ml), brine (2 ml), saturated sodium bicarbonate solution (2 ml), and brine (3×2 ml). The dried (MgSO$_4$) organic layer evaporated and the residue chromatographed on silica gel eluting with ethyl acetate/hexane mixtures to give the title azetidinone (146) (471 mg), a solid, m.p. 115°–116° C. (rods ex ethyl acetate/hexane; [α]D$^{22}$ −31.8° (c 1 in CHCl$_3$); ν$_{max}$ (CHCl$_3$) 1755 cm$^{-1}$; δppm (CDCl$_3$) 0.90 (9H, s). 4.25 (1H, s), 4.30 (1H, s), 7.10–7.50 (15H, m), both Me$_3$Si signals were obscured by TMS. (Found: C, 62.6; H, 5.9; N, 2.6S, 5.9 Br, 14.7. C$_{28}$H$_{32}$NBrOSSi requires C, 62.4; H, 6.0; N, 2.6; S, 6.0; Br, 14.8%).

Preparation 16(c)

(3S, 4R) 1-t-Butyldimethysilyl-3-(1-methyl-1,2,3-triazol-4-ylcarbonyl)-4-tritylthioazetidin-2-one A solution of n-butyl lithium (1.68M in hexane, 0.595 ml) was added to a stirred solution of the azetidinone (146) (538 mg) from Preparation 16(b) in dry THF (10 ml) at −76° C. under dry argon. After 10 minutes at −76° C. the stirred mixture was treated, in one portion, with solution of the triazole ester (145) (155 mg) from Preparation 16(a) in dry THF (3 ml). After 10 minutes at −76° C. the stirred mixture was treated with saturated ammonium chloride solution (3 ml) and allowed to attain room temperature. The mixture was diluted with ethyl acetate (30 ml) and was washed wih brine (3×5 ml). The dried (MgSO$_4$) organic layer was evaporated and the residue chromatographed on silica gel eluting with ethyl acetate/hexane mixtures to give the title ketone (147) (387 mg) as an amorphous solid, [α]D$^{22}$ +58.6° (C 1 in CHCl$_3$); ν$_{max}$(CHCl$_3$) 1750, 1680 cm$^{-1}$; δppm (CDCl$_3$) 0.92 (9H, s), 4.06 (3H, s), 4.70 (1H, d, J2 Hz), 4.95 (1H, d, J2 Hz), 6.9–7.5 (15H, m), 7.83 (1H, s), both Me$_3$Si signals were obscured by TMS.

Preparation 16(d)

(3S,4R) 1-t-Butyldimethylsilyl-3-[hydroxy(1-methyl-1,2,3-triazol-4-yl)methyl]-4-tritylthioazetidin-2-one The ketone (147) from Preparation 16(c) was treated with sodium borohydride (40 mg) as for Preparation 4(b) to give two fractions. The less polar fraction contained an isomer (Isomer A) of the title trans-azetinone (148) (67 mg) m.p. 195°–197° C. (needles ex ethylacetate/hexane); [α]D$^{22}$+69.00 (c 1 in CHCl$_3$); ν$_{max}$ (CHCl$_3$) 3600–3100, 1735 cm$^{-1}$; δppm (CDCl$_3$) 0.93 (9H, s), 1.84 (1H, brs, exch. D$_2$O), 3.29–3.38 (1H, m), 3.88 (1H, d, J2 Hz), 3.95 (3H, s), 4.51 (1H, d, J2 Hz), 7.10–7.50 (15H, m , 7.82 (IH, s , both Me$_3$Si signals obscured by TMS. (Found: C, 67.8; H, 6.7; N, 9.6; S, 5.6. C$_{32}$H$_{38}$N$_4$O$_2$SSi requires C, 67.3; H, 6.7; N, 9.8; S, 5.6%). The more polar fraction contained the other isomer (Isomer B) of the trans azetidinone (148) (167 mg) m.p. 128°–130° C. (plates ex ethyl acetate/hexane); [α]D$^{22}$−2.5° (c 1 in CHCl$_3$); ν$_{max}$ (CHCl$_3$) 3600–3100, 1730 cm$^{-1}$; δppm (CDCl$_3$) 0.78 (9H, s), 2.31 (1H, brs, exch. D$_2$O), 3.60 (1H, dd, J6 and 2 Hz), 3.92 (3H, s), 4.11 (1H, d, J6 Hz), 4.43 (1H, d, J2 Hz), 7.10–7.60 (16H, m), both Me$_3$Si signals were obscured by TMS. (Found: C, 66.8; H, 6.9; N, 9.8; S, 5.4. C$_{32}$H$_{38}$N$_4$O$_2$SSi requires C, 67.3; H, 6.7; N, 9.8; S, 5.6%).

Preparation 16(e)

(3S, 4R) 3-[Hydroxy(1-methyl-1,2,3-triazol-4-yl)methyl]-4-tritylthioazetidin-2-one The alcohol (148) (Isomer B) (3.03 g) from Preparation 16(d) was treated with potassium fluoride (339 mg) as for Preparation 2(b) to give the title azetidinone (149) (2.15 g) as a solid, m.p. 196°–197° C. (nuggets ex ethyl acetate/hexane); [α]D$^{22}$−124.7° (c 1 in CHCl$_3$); ν$_{max}$ (CHCl$_3$) 3600-3100, 1760 cm$^{-1}$; δppm (CDCl$_3$) 3.64 (1H, dd, J5 and 2 Hz), 3.65–3.95 (1H, br. signal, exch. D$_2$O), 4.16 (3H, s), 4.33 (1H, s), 4.60 (1H, d, J2 Hz), 5.26 (1H, slightly broadened d, J5 Hz, sharpens on exch. D$_2$O), 7.19–7.42 (15H, m), 7.63 (1H, s). (Found: C, 68.3; H, 5.3; N, 12.4; S, 7.0. C$_{26}$H$_{24}$N$_4$O$_2$S requires C, 68.4; H, 5.3; N, 12.3; S, 7.0%).

Preparation 16(f)

(3S, 4R) 3-[Acetoxy (1-methyl-1,2,3-triazol-4-yl)methyl]-4-tritylthioazetidin-2-one The azetidinone (149) (2.10 g) from Preparation 16(e) was treated with triethylamine (0.77 ml) 4-dimethylaminopyridine (56 mg) and acetic anhydride (0.52 ml) as for Preparation 1(c) to give the title acetate (150) (2.29 g) as a solid, m.p. 111°–113° (nuggets ex benzene/hexane); [α]D$^{21}$−97.0 (c 1 in CHCl$_3$); ν$_{max}$ (CHCl$_3$) 3390, 1770 cm$^{-1}$; δppm (CDCl$_3$) 2.11 (3H, s), 3.84 (1H, ddd, J6.5, 2.6 and 1.1Hz); 4.11 (3H, s), 4.17 (1H, brs), 4.70 (1H, d, J2.6 Hz), 6.17 (1H, d, J6.5 Hz), 7.22–7.58 (16H+approximately 1 mole benzene, m). (Found: C, 70.8; H, 5.7; N, 9.6; S, 5.5. C$_{28}$H$_{26}$N$_4$S.C$_6$H$_6$ requires C, 70.8; H, 5.6; N, 9.7; S, 5.6%).

Preparation 16(g)

(3S, 4R) 3-[Acetoxy (1-methyl-1,2,3-triazol-4-yl)methyl]-1(1-p-nitrobenzyloxycarbonyl-1-triphenylphosphoranylidenemethyl)-4-tritylthioazetidin-2-one The acetate (150) (2.22g) from Preparation 16(f) was converted via the hydroxyester (151), ν$_{max}$ (CHCl$_3$) 3600–3100, 1770 br. cm$^{-1}$; and the chloroester (152), ν$_{max}$ (CHCl$_3$) 1780 cm$^{-1}$; to the title phosphorane (153) (3.66 g), [α]D$^{20}$−33.0° (c 1 in CHCl$_3$); ν$_{max}$ (CHCl$_3$) 1750, 1620, 1605 sh. cm$^{-1}$, using the methods described in Preparation 1(d).

Preparation 16(h)

(3S, 4R) Silver 3-[Acetoxy (1-methyl-1,2,3-triazol-4-yl) methyl]-1-(1-p-nitrobenzyloxycarbonyl-1-triphenylphosphorylidenemethyl)-azetidin-2-one-4-thiolate Silver nitrate (8.7 ml of a 0.15M solution in methanol) was added to a stirred mixture of the phosphorane (153) (951 mg) from Preparation 16(g) and pyridine (0.015 ml) in methanol (10 ml) and dichloromethane (1 ml). After stirring at room temperature for 30 minutes the mixture was evaporated. The residual gum was re-evaporated from dry dichloromethane (5 ml) and dried under vacuum to give the crude title silver salt (154) as an amorphous solid. The material was of sufficient purity for further synthetic elaboration.

Prepartion 16(i)

(5R, 6S) p-Nitrobenzyl 6-[acetoxy(1-methyl-1,2,3-triazol-4-yl)methyl]penem-3-carboxylate The crude silver salt (154) from preparation 16(h) was treated 4-dimethylaminopyridine (122 mg), acetic formic anhydride (0.80 ml) and triethylammonium chloride (1.37g) as for Preparation 1,f) to give, after chromatography on silica gel eluting with dichloromethane/ethyl acetate mixtures, the penem (155) (378 mg) as a solid, mp. 151°–153° C. (hexagonal plates ex ethyl acetate/hexane); $[\alpha]_D^{20}+24.0°$ (c 1 in CHCl$_3$; $\nu_{max}$ (2% CHCl$_3$ in EtOH) 262 (εm 13380) and 316 nm (8889); $\nu_{max}$ (CHCl$_3$) 1795, 1740 sh, 1720 cm$^{-1}$; $\delta$ppm (CDCl$_3$) 2.09 (3H, s), 4.09 (3H, s), 4.56 (1H, ddd, J3.4, 2.2 and 1.0Hz), 5.25 and 5.43 (2H, ABq, J13.6 Hz), 6.20 (1H, d, J3.4 Hz), 6.23 (1H, d, J2.2 Hz), 7.36 (1H, d, J1.0Hz), 7.60 (2H, d, J8.7 Hz), 7.67 (1H, s), 8.23 (2H, d, J8.7 Hz}. (Found: C, 49.7; H, 3.7; N, 15.2; S, 6.9 C$_{19}$H$_{17}$N$_5$O$_7$S requires 49.7; H, 3.7; N, 15.3; S, 7.0%).

EXAMPLE 16(a)

(5R) p-Nitrobenzyl 6-(1-methyl-1,2,3-triazol-4-ylmethylene) penem-3-carboxylate The penem (155) (315 mg) from Preparation 16(i) was treated with 1,8-diazabicyclo[5.4.0]undec-7-ene (157 mg) as for Example 1(a) to give two fractions. The less polar fraction contained the (Z)-isomer (156) (243 mg) of the title penem, a solid, m.p. 174°–175° C. (microcrystalline solid ex dichloromethane/hexane); $[\alpha]_D^{20}+343.2°$ (c 1 in CHCl$_3$); $\nu_{max}$ (2% CHCl$_3$ in EtOH) 282 nm (εm 27183); $\nu_{max}$ CHCl$_3$) 1780, 1715 cm$^{-1}$; $\delta$ppm CDCl$_3$) 4.16 (3H, s), 5.29 and 5.46 (2H, ABq, J13.6 Hz), 6.68 (1H, d, J1.0 Hz), 7.06 (1H, d, J1.0Hz), 7.39 (1H, s), 7.62 (2H, d, J8.9 Hz), 7.73 (1H, s), 8.24 (2H, d, J8.9 Hz), a singlet at 5.30 ppm indicated the presence of dichloromethane. (Found: C, 48.7; H, 3.2; N, 16.4; S, 7.5; Cl, 5.1%). The more polar fraction contained the (E)-isomer (157) (7 mg) of the title penem, a solid, $\nu_{max}$ (Nujol Mull) 1750, 1710, 1685 cm$^{-1}$; $\delta$ppm (CDCl$_3$) 4.17 (3H, s), 5.31 and 5.47 (2H, ABq, J13.6 Hz), 6.49 (1H, s), 6.95 (1H, s), 7.46 (1H, s), 7.62 (2H, d, J8.7 Hz), 8.26 (2H, d,J8.7 Hz), 8.74 (1H, s).

EXAMPLE 16(b)

(5R) Sodium (Z)-6-(1-methyl-1,2,3-triazol-4-ylmethylene) penem-3-carboxylate The (Z)-penem ester (156) (200 mg) from Example 16(a) was hydrogenated as for Example 1(b) to give the title penem sodium salt (158) (81 mg) as a yellow freeze-dried solid, $[\alpha]_D^{18}+400°$ (c 1 in H$_2$O; $\nu_{max}$ (H$_2$O) 282 (εm 18459) and 354 nm (1589); $\nu_{max}$ (KBr) 3700–2750, 1760, 1680, 1555 cm$^{-1}$; ppm (D$_2$O) 4.10 (3H, s , 6.57 (1H, s), 7.02 (1H, s), 7.17 (1H, s), 8.13 (1H, s).

The penem sodium salt (158) (14mg) was partitioned between ethyl acetate (10 ml) and water (2 ml) and cooled in an ice bath. The pH of the vigorously stirred mixture was adjusted to 3.5 using 1% citric acid. The organic layer was separated and washed with water (3×1 ml). The dried (MgSO$_4$) organic layer was evaporated to give a crude solid. The crude solid was redissolved in ethyl acetate (20 ml) and filtered through Kieselguhr. The filtrate was evaporated to low volume (approximately 1 ml) and diluted with a little hexane to give the free acid of the title penem as yellow clusters of prisms, slow decomposition >150° C. finally melting at approximately 230° C.; $\nu_{max}$ (Nujol) 3400–2800, 1775, 1720, 1700 br. cm$^{-1}$; $\delta$ppm [(CD$_3$)$_2$SO) 4.10 (3H,s), 6.64 (1H, d, J 0.7 Hz), 7.32 (1H, d, J 0.7 Hz), 7.57 (1H,s), 8.39 (1H,s), 12.87 br (1H,s), other signals indicated the presence of 10–15% ethyl acetate.

Preparation 17(a)

(3RS, 4SR) 1-t-Butyldimethylsilyl-3-(1-methylpyrazol-3-yl-carbonyl)-4-tritylthioazetidin-2-one The azetidinone (1) (9.18 g) was reacted with methyl 1-methylpyrazole-3-carboxylate (2.86g) (K. V. Auwers and Th. Breyhan, J. Prakt. Chem., 1935, 143, 259) using the conditions described in Preparation 3(a) to give the title ketone (159) (8.63 g) as a solid, m.p. 200°–202° C. (prisms ex ethyl acetate/hexane); $\nu_{max}$ (CHCl$_3$) 1745, 1675 cm$^{-1}$; $\delta$ppm (CDCl$_3$) 0.31 (6H, s), 0.95 (9H, s), 3.88 (3H, s), 4.74 (1H, d, J2 Hz), 4.89 (1H, d, J2 Hz), 6.57 (1H, d, J3 Hz), 6.90–7.55 (16H, m). (Found: C, 69.6; H, 6.5; N, 7.3; S, 5.5. C$_{33}$H$_{37}$N$_3$O$_2$SSi requires C, 69.8; H, 6.6; N, 7.4; S, 5.6%).

Preparation 17(b)

(3RS, 4SR) 1-t-Butyldimethylsilyl-3-[hydroxy(1-methylpyrazol-3-yl)-methyl]-4-tritylthioazetidin-2-one The ketone (159) (8.85 g) from Preparation 17(a) was treated with sodium borohydride (0.9 g) as for Preparation 4(b) to give two fractions. The less polar fraction contained an isomer (Isomer A) of the title trans-azetidinone (160) (3.13 g), mp. 167°–169° C. (prisms ex ethyl acetate/hexane; $\nu_{max}$ (CHCl$_3$) 3700–3100, 1740 cm$^{-1}$; $\delta$ppm (CDCl$_3$) 0.24 (6H, s), 0.92 (9H, s), 2.30–2.60 (1H, broads, exch. D$_2$O), 3.44 (1H, dd, J2 and 3 Hz), 3.74 (3H, s), 3.78–3.95 (1H, broad m, collapses to 3.82, d, J3 Hz on exch. D$_2$O), 4.49 (1H, d, J2 Hz), 6.60 (1H, d, J3 Hz), 7.05–7.65 (16H, m). (Found: C, 69.4; H, 6.8; N, 7.4; S, 5.6. C$_{33}$H$_{39}$N$_3$O$_2$SSi requires C, 69.6; H, 6.9; N, 7.4; S, 5.6%). The more polar fraction contained an isomer (Isomer B) of the title trans-azetidinone (160) (4.63 g), mp 113°–115° C. (plates ex ethyl acetate/hexane); $\nu_{max}$ (CHCl$_3$) 3700–3200, 1735 cm$^{-1}$; $\delta$ppm (CDCl$_3$) 0.79 (9H, s), 1.90–2.60 (1H, broad s, exch. D$_2$O), 3.69 (dd, J2 and 6 Hz) and 3.74(s) together 4H, 4.09 (1H, broad d, J6 Hz, sharpens on exch. (D$_2$O) 4.22 (1H, d, J2 Hz), 5.89 (1H, d, J3 Hz), 7.05–7.60 (16H, m), both Me$_3$Si signals were obscured by TMS. (Found: C, 69.6; H, 7.0; N, 7.4; S, 5.6. C$_{33}$H$_{39}$N$_3$O$_2$SSi requires C, 69.6; H, 6.9; N, 7.4; S 5.6%).

Preparation 17(c)

(3RS, 4SR) 3-[Hydroxy(1-methylpyrazol-3-yl)methyl]-4-tritylthioazetidin-2-one The azetidinone (160) (Isomer B) (4.57 g) from Preparation 17(b) was treated with potassium fluoride (0.51 g) as for Preparation 2(b) to give title alcohol (161) 3.41 g) as a solid, m.p. 225°–227° C. (decomp) (needles ex ethyl acetate/hexane); $\nu_{max}$ (CHCl$_3$) 3400, 1760 cm$^{-1}$; $\delta$ppm (CDCl$_3$) 2.40–2.92 (1H, m), 3.54 (1H, dd, J3 and 5 Hz), 3.91 (3H, s), 4.22 (1H, broad s), 4.54 (1H, d, J3 Hz), 5.13 (1H, d, J5 Hz), 6.24 (1H, d, J1 Hz), 7.10–7.50 (16H, m). (Found: C, 71.4; H, 5.5; N, 9.2; S, 7.1. C$_{27}$H$_{25}$N$_3$O$_2$S requires C, 71.2; H, 5.5; N, 9.2; S, 7.0%).

Preparation 17(d)

(3RS, 4SR) 3-[Acetoxy(1-methylpyrazol-3-yl)methyl]-4-trityl thioazetidin-2-one The alcohol (161) (3.016 g) from Preparation 17(c) was treated with 4-dimethylaminopyridine (81 mg), triethylamine (1.106 ml) and acetic anhydride (0.75 ml) as for Preparation 1(c) to give, after chromatography on silica gel eluting with ethyl acetate/ethanol mixtures, the title acetate (162) (3.04 g) as a solid $\nu_{max}$ (CHCl$_3$) 3350, 1770 cm$^{-1}$; δppm (CDCl$_3$) 2.05 (3H, s), 3.73 (1H, dd, J6 and 3 Hz with further fine coupling J approximately 1 Hz), 3.88 (3H, s), 4.16 (1H, broad s), 4.50 (1H, d, J3 Hz), 6.10–6.20 (2H, m), 7.10–7.51 (16H, m).

Preparation 17(e)

3-[Acetoxy(1-methylpyrazol-3-yl)methyl]-1-(1-p-nitrobenzyloxycarbonyl-1-triphenylphosphoranylidenemethyl)-4-tritylthioazetidin-2-one The acetate (162) (2.77 g) from Preparation 17(d) was converted to the hydroxyester (163), $\nu_{max}$ (CHCl$_3$) 3550–2800, 1770 1750 ; cm$^{-1}$; the chloroester (164), $\nu_{max}$ (CHCl$_3$) 1780 cm$^{-1}$; and finally the title phosphorane (165) (4.37 g), $\nu_{max}$ (CHCl$_3$) 1755, 1620, 1605 cm$^{-1}$; using the methods described in Preparation 1(d).

Preparation 17(f)

(3RS, 4SR) Silver 3-[acetoxy (1-methylpyrazol-3-yl)methyl]-1-(1-p-nitrobenzyloxycarbonyl-1-triphenylphosphoranylidene-methyl)azetidin-2-one-4-thiolate The phosphorane (165) (4.37 g) from Preparation 17(e) was treated with silver nttrate/pyridine as for Preparation 1(e) to give the title silver thiolate (166) (2.5 g) as a yellow solid, $\nu_{max}$ (CHCl$_3$) 1750, 1615, 1605 cm$^{-1}$.

Preparation 17(g)

(5RS, 6SR) p-Nitrobenzyl 6-[acetoxy(1-methylpyrazol-3-yl)methyl]penem-3-carboxylate The silver thiolate (166) (2.42 g) from Preparation 7(f) was treated as for Preparation 1(f) to give the penem (167) (1.09 g) as a solid, m.p. 158°–160° C. (prisms ex ethyl acetate/hexane); $\nu_{max}$ (2% CHCl$_3$ in EtOH) 261 (εm 12846) and 317 nm (8327);$\nu_{max}$ (CHCl$_3$) 1795, 1740 sh, 1720 cm$^{-1}$; δppm (CDCl$_3$) 2.10 (3H, s), 3.86 (3H, s), 4.50 (1H, ddd, J3.8, 2.2 and 1.0 Hz), 5.35 (2H, ABq, J13.6 Hz), 6.05 (1H, d, J2.2 Hz), 6.26 (1H, d, J3.8 Hz), 6.29 (1H, d, J2.2 Hz), 7.30 (1H, d, J2.2 Hz); 7.32 (1H, d, J1Hz), 7.60 (2H, d, J8.5 Hz), 8.23 (2H, d, J8.5 Hz) (Found: C, 52.7; H, 4.0; N, 12.0; S, 6.8. C$_{20}$H$_{18}$N$_4$O$_7$S requires C, 52.4; H, 4.0; N, 12.2; S, 7.0%).

EXAMPLE 17(a)

(5RS) p-Nitrobenzyl 6-(1-methylpyazol-3-ylmethylene)penem-3-carboxylate

The penem (167) (458 mg) from Preparation 17(g) was treated with 1,8-diazabicyclo[5.4.0]undec-7-ene (228 mg) as for Example 1(a) to give two products. The less polar product, the (Z)-isomer (168) (373 mg) was obtained as a yellow solid, mp 175°–180° C. decomp. (prisms ex dichloromethane/hexane); $\nu_{max}$ (2% CHCl$_3$/EtOH) 297 nm (εm 30426); $\nu_{max}$ (CHCl$_3$) 1775, 1715, 1685 sh. cm$^{-1}$; δppm (CDCl$_3$) 3.96 (3H, s), 5.29 and 5.45 (2H, ABq, J13.6 Hz), 6.40 (1H, d, J2.3 Hz), 6.50 (1H, s), 7.04 (1H, s), 7.35 (1H, s), 7.39 (1H, d, J2.3 Hz), 7.63 (2H, d, J8.7 Hz), 8.24 ,(2H, d, J8.7 Hz) (Found: C, 54.3; H, 3.5; N, 14.1; S, 8.0. C$_{18}$H$_{14}$N$_4$O$_5$S requires C, 54.4; H, 3.4; N, 13.9; S, 8.0%). The more polar product, the (E)-isomer (169) (10 mg) of the title penem, was obtained as a yellow solid, $\nu_{max}$ (CHCl$_3$) 1775, 1720, 1680 cm$^{-1}$; δppm (CDCl$_3$) 3.94 (3H, s), 5.30 and 5.46 (2H, ABq, J13.7 Hz), 6.45 (1H, s), 6.75 (1H, s), 7.39 (1H, d, J2.5 Hz), 7.41 (1H, d, J2.5 Hz), 7.43 (1H, s), 7.62 (2H,.d, J8.7 Hz), 8.25 (2H, d, J8.7 Hz).

EXAMPLE 17(b)

(5RS) Sodium (Z)-6-(1-methylpyrazol-3-ylmethylene)penem-3-carboxylate

The (Z)-penem ester (168) (200 mg) from Example 17(a) was hydrogenated as for Example 1(b) to give the title sodium salt (169) (82 mg) as a yellow freeze-dried solid, λ$_{max}$ (H20) 291 (εm 23228) and approximately 360 nm (2036); $\nu_{max}$ (KBr) 3700–2600, 1750, 1680, 1600, 1550 cm $^{-1}$; δppm (D$_2$O) 3.90 (3H, s), 6.42 (1H, d, J2.3 Hz), 6.52 (1H, s), 7.00 (1H, s), 7.09 (1H, s), 7.62 (1H, d, J2.3 Hz).

Preparation 18(a)

(3RS, 4SR) 1-t-Butyldimethylsilyl-3-(1-methylimidazol-4-yl carbonyl)-4-tritylthioazetidin-2-one A solution of n-butyl lithium (1.68M in hexane, 0.71 ml) was added to a solution of diisopropylamine (0.17 ml) in dry THF (10 ml) at −30° C. under dry argon. After 15 minutes the stirred mixture was cooled to −70° C. and treated with a solution of the azetidinone (1) (459 mg) in dry THF (6 ml). After a further 15 minutes at −70° C. the stirred mixture was treated with a solution of methyl 1-methylimidazole-4-carboxylate (0.14 g) (P. K. Martin et al., *J. Org. Chem.*, 1968, 33, 3758) in dry THF (3 ml). The mixture was stirred at −70° C. for a further 30 minutes, treated with saturated ammonium chloride solution, and worked up as for Preparation 3(a) to give the title ketone (170) (0.37 g) as a solid, $\nu_{max}$ (CHCl$_3$) 1745, 1655 cm$^{-1}$; δppm (CDCl$_3$) 0.91 (9H, s), 3.64 (3H, s), 4.53 (1H, d, J1 Hz), 4.93 (1H, d, J1 Hz), 6.90–7.50 (17H, m), both Me$_3$Si signals obscured by TMS.

Preparation 18(b)

(3RS, 4SR) 1-t-Butyldimethylsilyl-3-[hydroxy(1-methylimidazol-4-yl)methyl]-4-tritylthioazetidin-2-one The ketone (170) (1.60 g) from Preparation 18(a) was treated with sodium borohydride as for Preparation 4(b) to give a 5:1 mixture of isomers of the title alcohol (171) (1.41 g) as a solid, $\nu_{max}$ (CHCl$_3$) 1735 cm$^{-1}$; δppm (CDCl$_3$) (major isomer) 0.01 and 0.02 (6H, each s), 0.79 (9H, s), 2.40–2.70 (1H, broad signal), 3.55 (3H, s), 3.68 (1H, dd, J1.7 and 6.4 Hz), 4.02 (1H, d, J6.4 Hz), 4.30 (1H, d, J1.7 Hz), 6.60 (1H, d, J0.8 Hz), 7.17–7.52 (16H, m). δppm (CDCl$_3$) (minor isomer) (inter alia) 0.26 and 0.27 (6H, each s), 0.94 (9H, s), 1.80–2.15 (1H, broad signal), 3.36–3.41 (1H, m), 3.58 (3H, s), 4.53 (1H, d, J2 Hz), 6.95 (1H, broad s).

Preparation 18(c)

(3RS, 4SR)
3-[Hydroxy(1-methylimidazol-4-yl)methyl]-4-tritylthi-
oazetidin-2-one The mixture of isomers of the alcohol (171) (1.204 g) from Preparation 18(b) was treated with potassium fluoride (135 mg) as for Preparation 2(b) to give a mixture of isomers of the title azetidinone (172) (958 mg) as a solid after trituration with ether, $v_{max}$ (Nujol Mull) 3700–3100, 765 cm$^{-1}$.

Preparation 18(d)

(3RS, 4SR)
3-[Acetoxy(1-methylimidazol-4-yl)methyl]-4-tritylthi-
oazetidin-2-one The mixture of isomers of the azetidinone (172) (622 mg) from Preparation 18(c) was treated with 4-dimethylaminopyridine (16.7 mg), triethylamine (0.21 ml), and acetic anhydride (0.14 ml) as for Preparation 1(c) to give a mixture of isomers of the title acetate (173), $v_{max}$ (CHCl$_3$) 3390, 1765 cm$^{-1}$.

Preparation 18(e)

(3RS, 4SR)
3-[Acetoxy(1-methylimidazol-4-yl)methyl]-1-(1-p-
nitrobenzyloxcarbonyl-1-triphenylphos-
phoranylidenemethyl)-4-tritylthioazetidin-2-one The mixture of isomers of the acetate (173) (267 mg) from Preparation 18(d) was converted to the hydroxyesters (174), $v_{max}$ (CHCl$_3$) 3600–3100, 1765 cm$^{-1}$; the chloroesters (175), $v_{max}$ (CHCl$_3$) 1780 cm$^{-1}$; and finally a mixture of isomers of the title phosphoranes (176) (114 mg), $v_{max}$ (CHCl$_3$) 1740, 1620, 1610 cm$^{-1}$ using the methods described in Preparation 1(d).

Preparation 18(f)

(3RS, 4SR) Silver
3-[acetoxy(1-methylimidazol-4-yl)methyl]-1-(1-p-
nitrobenzyloxycarbonyl-1-triphenylphosphoranyli-
dene-methyl)azetidin-2-one-4-thiolate.

The mixture of isomers of the phosphorane (176) (0.11 g) from Preparation 18(e) was treated with silver nitrate/pyridine as for Preparation 16(h) to give a crude mixture of isomers of the title silver salt (177).

Preparation 18(g)

(5RS, 6SR) p-Nitrobenzyl
6-[Acetoxy(1-methylimidazol-4-yl)
methyl]penem-3-carboxylate.

The crude mixture of isomers of the silver salt (177) from Preparation 18(f) was treated as for Preparation 1(f) to give two products. The less polar product, an isomer (Isomer A) of the title penem (178) (50 mg), was obtained as a solid contaminated with triphenylphosphine oxide, $v_{max}$ (CHCl$_3$) 1790, 1740 sh, 1720 cm$^{-1}$. The more polar product, an isomer (Isomer B) of the title penem (178) (20 mg) was obtained as a solid, $v_{max}$ (CHCl$_3$) 1790, 1720 br cm$^{-1}$.

Isomer A of the title penem (178) could be obtained free of triphenylphosphine oxide by careful chromatography but not without considerable column losses.

EXAMPLE 18

(5RS) p-Nitrobenzyl
(Z)-6-(1-methylimidazol-4-ylmethylene)
penem-3-carboxylate.

The penem (178) (Isomer A - free from triphenylphosphine oxide) (12 mg) from Preparation 18(g) was treated with 1,8-diazabicyclo[5.4.0]undec-7-ene (5.9 mg) as for Example 1(a) to give the title penem (179) (6 mg) as a solid, $v_{max}$ (CHCl$_3$) 1775, 1715, 1695 cm$^{-1}$; δppm (CDCl$_3$) 3.72 (3H, s), 5.28 and 5.46 (1H, ABq, J13.4 Hz), 6.65 (1H, s), 6.98 (1H, s), 7.18 (1H, s), 7.35 (1H, s), 7.48 (1H, s), 7.62 (2H, d, J8.6 Hz), 8.23 (2H, d, J8.6 Hz).

Biological data

The following Table 1 summaries the antibacterial activity of selected compounds according to the invention (which are identified by compound numbers as given in the examples) against selected micro-organisms and, for comparison purposes, also gives the same data for amoxycillin. The data is given in the form of MIC values (minimum inhibitory concentration) in μg/ml.

Table 2 summaries the β-lactamase activity of the compounds listed in Table 1 when used in conjunction with amoxycillin against the same micro-organisms. The data is given in the form of the minimum inhibitory amount of amoxycillin in μg/ml when used in conjunction with 5 μg/ml of the respective compound according to the invention.

TABLE 1

| Antibacterial Activity of Compounds Alone (MIC μg/ml) | | | | |
|---|---|---|---|---|
| Compound No (see Examples) | P mirabilis C889 | E coli JT410 | C freundii Mantio | E aerogenes N1 |
| 11 | >100 | >100 | >100 | >100 |
| 43 | 256 | >512 | 256 | >512 |
| 78 | 256 | >512 | >512 | >512 |
| 88(a) | 128 | 64 | 128 | 128 |
| 158 | 64 | 32 | 64 | 256 |
| 169 | 256 | 512 | 256 | 512 |
| Amoxycillin* | >512 | 256 | >512 | 512 |

*Typical MIC's from a number of tests

TABLE 2

| Amoxycillin MIC values (μg/ml) in the presence of compounds of this invention (5 μg/ml) | | | | |
|---|---|---|---|---|
| Compound No (see Examples) | P mirabilis C889 | E coli JT410 | C freundii Mantio | E aerogenes N1 |
| 11 | 1 | 8 | 8 | 16 |
| 43 | 1 | 1 | 2 | 2 |
| 78 | 2 | 2 | 32 | 16 |
| 88(a) | 2 | 2 | 1 | 2 |
| 158 | 2 | 1 | 2 | 2 |
| 169 | 1 | 2 | 2 | 4 |

I claim:
1. A compond of formula I:

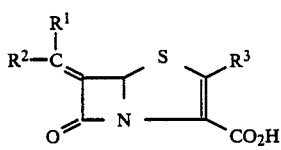

or a pharmaceutically acceptable salt or in vivo hydrolysable ester thereof in which
one of R$^1$ and R$^2$ is hydrogen, the other of R[1] and R[2] is a unsubstituted or substituted five-membered hetero-aromatic ring bonded through a carbon atom thereof and having oen hetero-atom selected from nitrogen, oxygen and sulphur and additionally having from one to three nitrogen atoms, wherein one or more substituents are (a)($C_{1-6}$)alkanoyl, (b) ($C_{1-6}$)alkanoyloxy, (c) heterocyclyl, (d) amino, (e) ($C_{1-6}$)alkanoylamino, (f) (mono or di)-($C_{1-6}$)alkylamino, (g) hydroxy, (h) ($C_{1-6}$)alkoxy, (i)sulpho, (j)mercapto, (k) ($C_{1-6}$)alkylthio, (l)($C_{1-6}$)alkylsulphinyl, (m) ($C_{1-6}$)alkylsulphonyl, (n) heterocyclylthio, (o) arylthio, (p) sulphamoyl, (g) carbamoyl, (r) amidino, (s) guanidino, (t) nitro, (u) halogen, (v) carboxy, (w) pharmaceutically acceptable carboxy salts, (x) pharmaceutically acceptable carboxy esters, (y)arylcarbonyl or (z) heterocyclylcarbonyl groups, and (aa)unsubstituted or substituted ($C_{1-6}$)alkyl, ($C_{2-6}$)alkenyl, ($C_{2-6}$)alkynyl, aryl, and aryl($C_{1-6}$)alkyl groups, wherein one or more substituents for said (aa) groups are ($C_{1-6}$)alkanoyl, ($C_{1-6}$)alkanoyloxy, heterocyclyl, amino, ($C_{1-6}$)alkanoylamino, (mono or di)-($c_{1-6}$)alkylamino, hydroxy, ($C_{1-6}$)alkylsulphinyl, ($C_{1-6}$)alkysulphonyl, heterocyclylthio, arylthio, suphamoyl, carbamoyl, amidino, guanidino, nitro, halogen, carboxy pharmaceutically acceptable carboxy salts, pharmaceutically acceptable carboxy esters, arylcarbonyl or heterocyclylcarbonyl groups, and $R_3$ is hydrogen, ($C_{1-10}$)alkyl or ($C_{1-10}$)alkylthio, or substituted ($C_{1-10}$)alkyl or substituted ($C_{1-10}$)-alkylthio, wherein the substituent is hydroxy, ($C_{1-6}$)alkoxy, ($C_{1-6}$)alkanoyloxy, halogen, mercapto, ($C_{1-6}$)alkylthio, heterocyclylthio, amino, (mono or di)-($C_{1-6}$)alkylamino, ($C_{1-6}$)alkanoylamino, carboxy, or ($C_{1-6}$)alkoxycarbonyl, wherein heterocyclyl is aromatic or non-aromatic, having single or fused, rings having up to four hetero-atoms in each ring selected form oxygen, nitrogen and sulphur which rings are unsubstituted or substituted by up to three groups selected from halogen, ($C_{1-6}$)alkyl, ($C_{1-6}$)alkoxy, halo($C_{1-6}$)alkyl, hydroxy, amino, carboxy, ($C_{1-6}$)alkoxycarbonyl, ($C_{1-6}$)alkoxycarbonyl($C_{1-6}$)alkyl, aryl, ($C_{1-6}$)alkylthio, arylthio, mercapto and oxo groups, and said aryl is phenyl or naphthyl, wherein each is unsubstituted or substituted by to give groups selelcted form halogen, ($C_{1-6}$)alkyl, phenyl, ($C_{1-6}$)alkoxy, halo($C_{1-6}$)alkyl, hydroxy, amino, nitro, carboxy, ($C_{1-6}$)alkoxycarobnyl, ($C_{1-6}$)alkoxycarbonyl($C_{1-6}$)alkyl, ($C_{1-6}$)alkylcarbonyloxy, ($C_{1-6}$)alkylcarbonyl, ($C_{1-6}$)alkylthio, arylthio and mercapto groups.

2. A compound or formula IA:

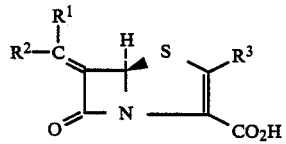

or a pharmaceutically acceptable salt or in vivo hydrolysable ester thereof in which
one of R[1] and R[2] is hydrogen,
the other R[1] and R[2] is an unsubstituted or substituted five-membered hetero-aromatic ring bonded through a carbon atom thereof and having one hetero-atom selected from nitrogen, oxygen and sulphur and additionally having from one to three nitrogen atoms, wherein one or more substituents are (a) ($C_{1-6}$)alkanoyl, (b) ($C_{1-6}$)alkanoyloxy, (c) heteroycyclyl, (d) amino, (e) ($C_{1-6}$)alkanoylamino, (f) (mono or di)-($c_{1-6}$)alkylamino, (g) hydroxy, (h) ($C_{1-6}$)alkoxy, (i)sulpho, (j) mercapto, (k) ($C_{1-6}$)alkylthio, (l)($C_{1-6}$)alkylosulphinyl, (m) ($C_{1-6}$)alkylsulphonyl, (n)heterocyclythio, (o) arylthio, (p) sulphamoyl, (q)carbamoyl, (r)amidino, (s) quanidino, (t) nitro, (u)halogen, (v) carboxy, (w) pharmaceutically acceptable carboxy salts, (x) pharamceutically acceptable carboxy esters, (y)arylcarbonyl or (z) heterocyclylcarbonyl groups, and (aa)unsubstituted or substituted ($C_{1-6}$)alkyl, ($C_{2-6}$)alkenyl, ($C_{2-6}$)alynyl, aryl, and aryl($C_{1-6}$)alkyl groups, wherein one or more substituents for said (aa) groups are ($C_{1-6}$)alkanoyl, ($C_{1-6}$)alknoyloxy, heterocyclyl, amino ($C_{1-6}$)alknoylamino, (mono or di)-($C_{1-6}$)alkylamino, hydroxy, ($C_{1-6}$)alkylsuophinyl, ($C_{1-6}$)alkylsulphonyl, heterocyclylthio, arylthio, sulphamoyl, carbamoyl, amidino, quanidino, nitro, halogen, carboxy pharmaceutically acceptable carboxy salts pharmaceutically acceptable carboxy esters, arylcarbonyl or heterocyclylcarbonyl groups, and $R_3$ is hydrogen, ($C_{1-10}$)alkyl or ($C_{1-10}$)alkylthio, or substituted ($C_{1-10}$)alkyl or substituted ($C_{1-10}$)-alkylthio, wherein the substituent is hydroxy, ($C_{1-6}$)alkoxy, ($C_{1-6}$)alkanoyloxy, halogen, mercapto, ($C_{1-6}$)alkylthio, heterocyclylthio, amino, (mono or di)-($C_{1-6}$)alkylamino, ($C_{1-6}$)alkanoylamino, carboxy, or ($C_{1-6}$)alkoxycarbonyl, wherein heterocyclyl is aromatic or non-aromatic, having single or fused, rings having up to four hetero-atoms in each ring selected form oxygen, nitrogen and sulphur which rings are unsubstituted or substituted by up to three groups selected from halogen, ($C_{1-6}$)alkyl, ($C_{1-6}$)alkoxy, halo($C_{1-6}$)alkyl, hydroxy, amino, carboxy, ($C_{1-6}$)alkoxycarbonyl, ($C_{1-6}$)alkoxycarbonyl($C_{1-6}$)alkyl, aryl, ($C_{1-6}$)alkylthio, arylthio, mercapto and oxo groups, and said aryl is phenyl or naphthyl, wherein each is unsubstituted or substituted by up to five groups selectled from halogen, ($C_{1-6}$)alkyl, phneyl, ($C_{1-6}$)alkoxy, halo($C_{1-6}$)alkyl, hydroxy, amino, nitro, carboxy, ($C_{1-6}$)alkoxycarbonyl, ($C_{1-6}$)alkoxycarbonyl($C_{1-6}$)alkyl, ($C_{1-6}$)alkylcarbonyloxy, ($C_{1-6}$)alkylcarbonyl ($C_{1-6}$)alkylthio, arylhto and mercapto groups.

3. A compound according to claim 1, wherein R[1] denotes said hetero-aromatic group and R[2] denotes a hydrogen atom.

4. A compound as claimed in claim 2, wherein R[1] denotes the hetero-aromatic group and R[2] denotes a hydrogen atom.

5. A compound according to claim 1, wherein the hetero-aromatic group is an oxazolyl, isoxazolyl, pyrazolyl or triazolyl group.

6. A compound selected from:
(5RS) (Z)-6-(isothiazol-5-ylmethylene)penem-3-carboxylic acid;

(5RS) (E)-6-[(1-methylpyrazol-4-yl)methylene]-penem-3-carboxylic acid;

(5RS) (Z)-6-[(1-methylpyrazol-4-yl)methylene]penem-3-carboxylic acid;

(5RS) (Z)-6-[(2-methylthiazol-4-yl)methylene]penem-3-carboxylic acid;

(5RS) (Z)-6-(isoxazol-3-ylmethylene)penem-3-carboxylic acid;

(5RS) (Z)-6-[(2,4-dimethyloxazol-5-yl)methylene]-penem-3-carboxylic acid;
(5RS) (E)-6-[(4-methyl-1,2,3-thiadiazol-5-yl) methylene]penem-3-carboxylic acid;
(5RS) (Z)-6-[(4-methyl-1,2,3-thiadiazol-5-yl) methylene]penem-3-carboxylic acid;
(5RS) (Z)-6-[(2-methyloxazol-4-yl)methylene]penem-3-carboxylic acid;
(5RS) (Z)-6-[(1-methyl-1,2,3-triazol-4-yl)methylene]-penem-3-carboxylic acid;
(5RS) (E)-6-[(1-methyl-1,2,3-triazol-4-yl)methylene]-penem-3-carboxylic acid;
(5R) (Z)-6-[(1-methyl-1,2,3-triazol-4-yl)methylene]-penem-3-carboxylic acid;
(5RS) (Z)-6-[(5-methyl-1,2,4-oxadiazol-3-yl)methylene]penem-3-carboxylic acid;
(5RS) (Z)-6-[(1-methyl-1,2,4-triazol-3-yl)methylene]-penem-3-carboxylic acid;
(5RS) 2-hydroxymethyl-6(Z)-[(1-methylpyrazol-4-yl)methylene]penem-3-carboxylic acid;
(5RS) 2-ethylthio-6(Z)-[(1-methylpyrazol-4-yl)methylene]penem-3-carboxylic acid;
(5RS) 2-(2-hydroxyethylthio)-6(Z)-[(1-methylpyrazol-4-yl)methylene]penem-3-carboxylic acid;
(5RS) (Z)-6-(N-methyltetrazol-5-ylmethylene)penem-3-carboxylic acid;
(5RS) (Z)-6-[(1-methylpyrazol-3-yl)methylene]penem-3-carboxylic acid;
(5RS) (Z)-6-[(1-methylimidazol-4-yl)methylene]penem-3-carboxylic acid; or a pharmaceutically acceptable salt or in-vivo hydrolysable ester thereof.

7. A compound of formula IIIC:

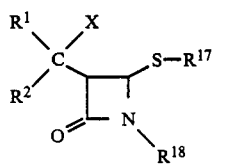

in which
R$^1$ and R$^2$ are defined as in claim 1,
R$^{17}$ is (C$_{1-6}$) alkyl, aryl, aryl (C$_{1-6}$) alkyl, (C$_{1-6}$) alkylthio, arylthio, hetero-aromatic-thio, acyl (C$_{2-6}$) alkenyl, or aryl (C$_{2-6}$) alkenyl, all of which optionally substituted,
wherein the substituents for (C$_{1-6}$)alkyl, aryl and aryl (C$_{1-6}$)alkyl are (C$_{1-6}$)alkanoyl, (C$_{1-6}$)alkanoyloxy, heterocyclyl, amino, (C$_{1-6}$)alknaoylamino, (mono or di)-(C$_{1-6}$-)alkylamino, hydroxy, (C$_{1-6}$)alkylsulphinyl, (C$_{1-6}$)alkylsulphonyl, heterocycylthio, arylthio, sulphamoyl, carbamoyl, amidino, quanidino, nitro, halogen, carboxy, pharmaceutically acceptable carboxy salts, pharmaceutically acceptable carboxy esters, arylcarbonyl or heterocyclylcarbonyl groups,
aryl is phenyl or naphthyl, wherein each is unsubstituted or substituted by up to five groups selected from halogen, (C$_{1-6}$)alkyl, phenyl, (C$_{1-6}$)alkoxy, halo(C$_{1-6}$)alkyl, hydroxy, amino, nitro, carboxy, (C$_{1-6}$)alkoxycarbonyl, (C$_{1-6}$)alkoxycarbonyl(C$_{1-6}$)alkyl, (C$_{1-6}$)alkylcarbonyloxy, (C$_{1-6}$)alkylcarbonyl, (C$_{1-6}$)alkylthio, arylthio and mercapto groups and
said heteroaromatic has single or fused, rings having up to four hereto-atoms in each ring selected from oxygen, nitrogen and sulphur which rings are unsubstituted or substituted by up to three groups selected from halogen, (C$_{1-6}$)alkyl, (C$_{1-6}$)alkoxy, halo(C$_{1-6}$)alkyl, hydroy, amino, carboxy, (C$_{1-6}$)alkoxyarbonyl, (C$_{1-6}$)alkoxycarbonyl(C$_{1-6}$)alkyl, aryl, (C$_{1-6}$)alkylthiuo, arylthio, mercapto and oxo groups,
R$^{18}$ is hydrogen or an N-protectign silyl group, and
X is a hydroxy group or a leaving group,
wherein said leaving group is a halogen atom or a group of one of the formulae

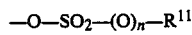      VIIIA

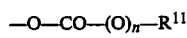      VIIIB or

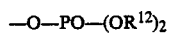      VIIIC in which
n is 0 or 1,
R$^{11}$ is (C$_{1-6}$) alkyl, aryl or aryl (C$_{1-6}$) alkyl, and
R$^{12}$ is (C$_{1-6}$) alkyl or aryl, wherein said aryl is phenyl or naphthyl, wherein each is unsubstituted or substituted by up to five groups selected from halogen, (C$_{1-6}$) alkyl phenyl, (C$_{1-6}$) alkoxy, halo (C$_{1-6}$) alkyl, hydroxy, amino, nitro, arboxy, (C$_{1-6}$) alkoxy carbonyl, (C$_{1-6}$) alkoxyarbonyl (C$_{1-6}$) alkyl (C$_{1-6}$) alkyl carbonyloxy, (C$_{1-6}$) alkylcarbonyl (C$_{1-6}$) alkylthio, arylthio and mercapto groups.

8. A compound of formula IVC:

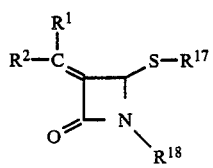

in which, R$^1$ and R$^2$ are defined as in claim 1 and R$^{17}$ and R$^{18}$ are defined as in claim 7.

9. A compound of formula IVE;

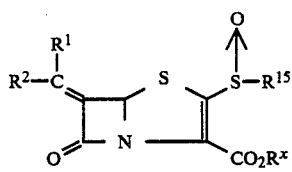

in which
R$^1$ and R$^2$ are defined as in claim 1,
R$^{15}$ is (C$_{1-10}$)alkyl or substituted (C$_{1-10}$)alkyl wherein the substituent is hydroxy, (C$_{1-6}$)alkoxy, (C$_{1-6}$)alkanoyloxy, halogen, mercapto, (C$_{1-6}$)alkylthio, heterocyclythio, amino, (mono or di)-(C$_{1-6}$)alkylamino, (C$_{1-6}$)alkanoylamino, carboxy, or (C$_{1-6}$)alkoxycarbonyl, and
R$^x$ is hydrogen or a carboxyl - blocking group.

10. A pharmaceutical composition useful for treating bacterial infections in humans and animals which comprises an antibacterially effective amount or a β-lactamase inhibitory amount of a compound of formula I:

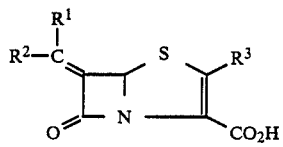

or a pharmaceutically acceptable salt or in vivo hydrolysable ester thereof in which
one or $R^1$ or $R^2$ is hydrogen,
the other of $R^1$ and $R^2$ is an unsubstituted or substituted five-membered hetero-aromatic ring bonded through a carbon atom thereof and having one hetero-atom selected from nitrogen, oxygen and sulphur and additionally having from one to three nitrogen atoms, wherein one or more substituents are (a)$(C_{1-6})$alkanoyl, (b) $(C_{1-6})$alkanoyloxy, (c) heterocyclyl, (d) amino, (e) $(C_{1-6})$alkanoylamino, (f) (mono or di)-$(C_{1-6})$alkylamino, (g) hydroxy, (h) $(C_{1-6})$alkoxy, (i) sulpho, (j) mercapto, (k) $(C_{1-6})$alkylthio, (l) $(C_{1-6})$alkylsulphinyl, (m) $(C_{1-6})$alkylsulphonyl, (n) heterocyclythio, (o) arylthio, (p) suophamoyl, (q) carbamoyl, (r) amidino, (s) quanidino, (t) nitro, (u) halogen, (v) carboxy, (w) pharmaceutially acceptable carboxy saslts, (x) pharamceutically acceptable carboxy esters, (y) arylcarbonyl or (z) heterocyclylcarbonyl groups, and unsubstituted or substituted $(C_{1-6})$alkyl, $(C_{2-6})$alkenyl, $(C_{2-6})$alkynyl, aryl, and aryl$(C_{1-6})$alkyl groups, wherein one or more substituents for said (aa) groups are $(C_{1-6})$alkanoyl, $(C_{1-6})$alkanoyloxy, heterocyclyl, amino, $(C_{1-6})$alknaoylamino, (mono or di)-$(C_{1-6})$alkylamino, hydroxy, $(C_{1-6})$alkylsulophinyl, $(C_{1-6})$alkylsulphonyl, heterocylcylthio, arylthio, sulphamoyl, carbamoyl, amidino, quanidino, nitro, halogen, carboxy, pharmaceutically acceptable carboxy salts, pharmaceutically acceptable carboxy esters, arylcarbonyl or heterocyclylcarbonyl groups, and $R_3$ is hydrogen, $(C_{1-10})$alkyl or $(C_{1-10})$alkylthio, or substituted (Chd 1-10)alkyl or substituted $(C_{1-10})$alkylthio, wherein the substituent is hydroxy, $(C_{1-6})$alkoxy, $(C_{1-6})$alkanoyloxy, halogen, mercapto, $(C_{1-6})$alkylthio, heterocyclylthio, amino (mono or di)-$(C_{1-6})$alkylamino, $(C_{1-6})$alkanoylamino, carboxy, or $(C_{1-6})$alkoxycarbonyl, wherein heterocyclyl is aromatic or non-aromatic, having single or fused, rings having up to four hetero-atoms in each ring selected from oxygen, nitrogen and sulphur which rings are unsubstituted or substituted by up to three groups selected from halogen, $(C_{1-6})$alkyl, $(C_{1-6})$alkoxy, halo$(C_{1-6})$alkyl, hydroxy, amino, carboxy, $(C_{1-6})$alkoxycarbonyl, $(C_{1-6})$alkoxycarbonyl $(C_{1-6})$alkyl, aryl, $(C_{1-6})$alkylthio, arylthio, mercapto and oxo groups, and said aryl is phenyl or napthyl, wherein each is unsubstituted or substituted by up to five groups selected from halogen, $(C_{1-6})$alkyl phenyl, $(C_{1-6})$alkoxy, halo $(C_{1-6})$alkyl, hydroxy, amino, nitro, carboxy, $(C_{1-6})$alkoxycarbonyl, $(C_{1-6})$alkoxycarbonyl$(C_{1-6})$alkyl, $(C_{1-6})$alkylcarbonyloxy, $(C_{1-6})$alkylcarbonyl $(C_{1-6})$alkylthio, arylthio and mercapto groups and a pharmaceutically acceptable carrier.

11. A pharmaceutical composition according to claim 10, which additionally comprises a penicillin, cephalosporin or other β-lactam antibiotic.

12. A method of treating a bacterial infection, which comprises administering to a human or animal in need thereof an antibacterially effective amount of a β-lactamase inhibitory amount of a compound of formula I:

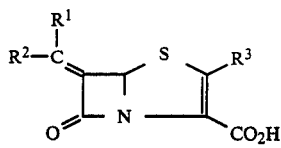

or a pharmaceutically acceptable salt or in vivo hydrolysable ester thereof in which
one of $R^1$ or $R^2$ is hydrogen,
the other of $R^1$ and $R^2$ is an unsubstituted or substituted five-membered hetero-aromatic ring bonded through a carbon atom thereof and having one-hetero-atom selected from nitrogen, oxygen and sulphur and additionally having from one to three nitrogen atoms, wherein one or more substituents are (a)$(C_{1-6})$alkanoyl, (b) $(C_{1-6})$alkanoyloxy, (c) heterocyclyl, (d) amino (e) $(C_{1-6})$alkanoylamino, (f) (mono or di)-$(C_{1-6})$alkylamino, (g) hydroxy, (h) $(C_{1-6})$alkoxy, (i) sulpho, (j) mercapto, (k) $(C_{1-6})$alkylthio, (l) $(C_{1-6})$alikylsulphinyl, (m) $(C_{1-6})$alkylsulphonyl, (n) heterocycylthio, (o) arylthio, (p) sulphamoyl, (g) carbamoyl, (r) amidino, (s) guanidino, (t) nitro, (u) halogen, (v) carboxy, (w) pharmaceutically acceptable carboxy esters, (y) arylcarbonyl or (z) heterocyclycarbonyl groups, and (aa) unsubstituted or substituted $(C_{1-6})$alkyl, $(C_{2-6})$alkenyl, $(C_{2-6})$alkylnyl, aryl, and aryl$(C_{1-6})$alkyl groups, wherein one or more substituents for said (aa) groups are $(C_{1-6})$alkanoyl, $(C_{1-6})$alkanoyloxy, heterocyclyl, amino, $(C_{1-6})$alkanoylamino, (mono or di)-$(C_{1-6})$alkylamino, hydroxy, $(C_{1-6})$alkylsulphinyl, $(C_{1-6})$alkylsulphonyl, heterocyclylthio, arylthio, sulphamoyl, carbamoyl, amidino, guanidino, nitro, halogen, carboxy, pharmaceutically acceptable carboxy salts pharmaceutically acceptable carboxy esters, arylcarbonyl or heterocyclylcarbonyl groups, and $R_3$ is hydrogen, $(C_{1-10})$alkyl or $(C_{1-10})$alkylthio, or substituted $(C_{1-10})$alkyl or substituted $(C_{1-10})$alkylthio, wherein the substituent is hydroxy, $(C_{1-6})$alkoxy, $(C_{1-6})$alkanoyloxy, halogen, mercapto, $(C_{1-6})$alkylthiuo, heterocyclylthio, amino, (mono or di)-$(C_{1-6})$alkylamino, $(C_{1-6})$alkanoylamino, carboxy, or $(C_{1-6})$alkoxycarbonyl, wherein h eterocycyl is aromatic or non-aromatic, having single or fused, rings having up to four hetero-atoms in each ring selected from oxygen, nitrogen and sulphur which rings are unsubstituted or substituted by up to three groups selected from halogen, $(C_{1-6})$alkyl, $(C_{1-6})$alkoxy, halo$(C_{1-6})$alkyl, hydroxy, amino, carboxy, $(C_{1-6})$alkoxycarbonyl, $(C_{1-6})$alkoxycarbonyl$(C_{1-6})$alkyl, aryl, $(C_{1-6})$alkylthio, arylthoi, mercapto and oxo groups, and said aryl is phenyl or napthyl, wherein each is unsubstituted or substituted by up to give groups selected from halogen, $(C_{1-6})$alkyl, phenyl, $(C_{1-6})$alkoxy, haloo$(C_{1-6})$alkyl, hydroxy, amino, nitro, carboxy, $(C_{1-6})$alkoxycarbonyl, $(C_{1-6})$alkoxycarbonyl$(C_{1-6})$alkyl, $(C_{1-6})$alkylcarbonyloxy, $(C_{1-6})$alkylcarobnyl $(C_{1-6})$alkylthio, arylthio and mercapto groups.

13. A method according to claim 12, wherein said compound, salt or ester is administered to said human of animal in conjnction with the prior, simultaneous or subsequent administration of a penicillin, cephalosporin or other β-lactam anitbiotic.

14. A compound according to claim 1 wherein the hetero-aromatic ring $R^1$ or $R^2$ contains at least two ring nitrogen atoms.

15. A compound according to claim 1, wherein the hetero-aromatic ring $R^1$ or $R^2$ is a isothiazolyl, isozazolyl, methylthiazolyl, methyloxazolyl, dimethyloxazolyl, methyl-1,2,3- thiadiazolyl, methyl-1,2,4-oxadiazolyl, N-methylpyrazolyl, N-methylimidazolyl, N-methyl-1,2,3,-triazolyl, N-methyl-1,2,4-triazolyl, or N-methyltetrazoloyl group.

16. A compound according to claim 1, wherein $R^3$ is a hydrogen, methyl, ethyl, propyl, methylthio, ethylthio, methylsulphinyl, ethylsulphinyl, hydroxymethyl, methoxymethyl, ethoxymethyl, acetoxymethyl, (1 or 2)-acetoxyethyl, aminomethyl, 2-aminoethyl, acetamidomethyl, 2-acetamidoethyl, carboxymethyl, 2-hydroxyethylthio, methoxymethylthio, 2-methoxyethylthio, acetoxymethylthio, 2-aminoethylthio. acetamidomethylthio, 2-acetamidomethylthio, carboxymethylthio, 2-carboxyethylthio, phenyl, phenylthio, pryidyl, pyrimidyl, isoxazoyl, pyrimidylthio, tetrazolylthio, or pyridylthio group.

17. A compound according to claim 1 wherein the in vivo hydrolysable ester groups are those of part-formulae (a), (b) and (c):

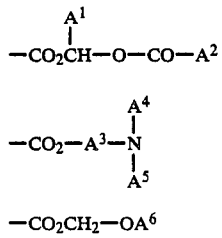

in which
A¹ is hydrogen, methyl, or phenyl;
A² is (C₁₋₆)alkyl, (C₁₋₆)alkoxy or phenyl; or
A¹ and A² together are 1,2-phenylene, which is unsubstituted or substituted by one or two methoxy groups;
A³ is (C₁₋₆)alkylene, which is unsubstituted or substituted by a methyl or ethyl group;
each of A⁴ and A⁵ which are identical or different, is C₁₋₆)alkyl; and
A⁶ is (C₁₋₆)alkyl.

18. A compound according to claim 1, wherein the in vivo hydrolysable ester groups are acetoxymethyl, pivaloyloxymethyl, α-acetoxyethyl, α-acetoxybenzyl, α-pivaloyloxyethyl, ethoxycarbonyloxymethyl, α-ethoxycarbonyloxyethyl, dimethylaminomethyl, diethylaminomethyl, phthalidyl or dimethoxyphthalidyl groups.

19. A compound according to claim 1, wherein the pharmaceutically acceptable salt is an alkali metal or alkaline earth metal salt.

20. A pharmaceutical composition according to claim 10, wherein the hetero-aromatic ring $R^1$ or $R^2$ contains at least two ring nitrogen atoms.

21. A pharmaceutical composition according to claim 10, wherein the hetero-aromatic ring $R^1$ and $R^2$ is a isothiazolyl, isoxazolyl, methylthiazolyl, methyloxazolyl, dimethyloxazolyl, methyl-1,2,3-thiadiazolyl, methyl-1,2,4-oxadiazolyl, N-methylpyrazolyl, N-methylimidazolyl, N-methyl-1,2,3,-triazolyl, N-methyl-1,2,4-triazolyl, or N-methyltetrazolyl group.

22. A pharmaceutical composition according to claim 10, wherein $R^3$ is a hydrogen, methyl, ethyl, propyl, methylthio, ethylthio, methylsulphinyl, ethylsulphinyl, hydroxymethyl, methoxymethyl, ethoxymethyl, acetoxymethylo, (1 or 2)-acetoxyethyl, aminomethyl, 2-aminoethyl, acetamidomethyl, 2-acetamidoethyl, carboxymethyl, 2-hydroxyethylthio, methoxymethylthio, 2-methylethylthio, acetoxymethylthio, 2-aminoethylthio, acetamidomethylthio, 2-acetamidomethylthio, carboxymethylthio, 2-carboxyethylthio, phenyl, phenylthio, pryidyl, pyrimidyl, isoxazolyl, pyrimidylthio, tetrazolylthio, or pyridylthio group.

23. A pharmaceutical composition according to claim 10, wherein the in vivo hydrolysable ester groups are those of part-formulae (a), (b) and (c):

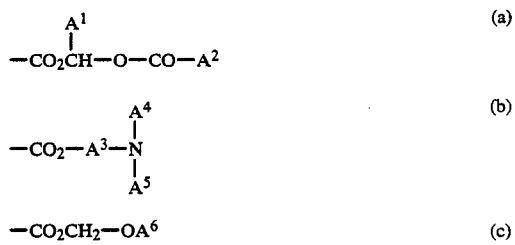

in which
A¹ is hydrogen, methyl, or phenyl;
A² is (C₁₋₆)alkyl, (C₁₋₆)alkoxy or phenyl; or
A¹ and A² together are 1,2-phenylene, which is unsubstituted or substituted by one or two methoxy groups;
A³ is (C₁₋₆)alkylene, whikch is unsubstituted or substituted by a methyl or ethyl group;
each of A⁴ and A⁵ which are identical or different, is (C₁₋₆)alkyl; and
A⁶ is (C₁₋₆)alkyl.

24. A pharmaceutical composition according to claim 10, wherein the in vivo hydrolysable ester groups are acetoxymethyl, pivaloyloxymethyl, α-acetoxyethyl, α-acetoxybenzyl, α-pivaolylethyl, ethoxycarbonylxoymethyl, α-ethoxycarbonyloxyethyl, dimethylaminomethyl, diethylaminomethyl, phthalidyl or dimethoxyphthalidyl groups.

25. A pharmaceutical composition according to claim 10, wherein the pharmaceutically acceptable salt is an alkali metal or alkaline earth metal salt.

26. A method according to claim 12, wherein the hetero-aromatic ring $R^1$ or $R^2$ includes at least two ring nitrogen atoms.

27. A method according to claim 12, wherein the hetero-aromatic ring $R^1$ or $R^2$ is a isothiazolyl, isoxazolyl, methylthiazolyl, methyloxazolyl, dimethyloxazolyl, methyl-1,2,3-thiadiazolyl, methyl-1,2,4-oxadiazolyl, N-methylpyrazolyl, N-methylimidazolyl, N-methyl-1,2,3-triazolyl, N-methyl-1,2,4-triazolyl, or N-methyltetrazolyl group.

28. A method according to claim 12, wherein $R^3$ is a methylsulphinyl, ethylsulphinyl, hydroxymethyl, methoxymethyl, ethoxymethyl, acetoxymethyl, (1 or 2)-acetoxyethyl, aminomethyl, 2-aminoethyl, acetamidomethyl, 2-acetamidoethyl, carboxymethyl, 2-hydroxyethylthio, methoxymethylthio, 2-methoxyethylthio, acetoxymethylthio, 2-aminoethylthio, acetamidomethylthio, 2-acetamidomethylthio, carboxymethylthio, 2- carboxyethylthio, phenyl, phenylthio, pyridyl, pyrimdiyl, isoxazolyl, pyridimidylthiuo, tetrazolylthio, or pyridylthio group.

29. A method according to claim 12, wherein the in vivo hydrolysable ester groups are those of part-formulae (a), (b) and (c):

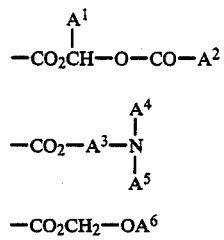

$$-CO_2CH-O-CO-A^2 \quad\text{(a)}$$
$$\phantom{-CO_2CH-O-CO-}A^1$$

$$-CO_2-A^3-N \quad\text{(b)}$$
$$\phantom{-CO_2-A^3-}A^4$$
$$\phantom{-CO_2-A^3-}A^5$$

$$-CO_2CH_2-OA^6 \quad\text{(c)}$$

in which
$A^1$ is hydrogen, methyl, or phenyl;
$A^2$ is $(C_{1-6})$alkyl, $(C_{1-6})$alkoxy or phenyl; or
$A^1$ and $A^2$ together are 1,2-phenyl, which is unsubstituted or substituted by one or two methoxy groups;
$A^3$ is $(C_{1-6})$alkylene, which is unsubstituted or substituted by a methyl or ethyl group;
each of $A^4$ and $A^5$ which are identical or different, is $(C_{1-6})$alkyl; and
$A^6$ is $(C_{1-6})$alkyl.

30. A method accoridng to claim 12, wherein the in vivo hydrolysable ester groups are acetoxymethyl, pivaloyloxymethyl, α-acetoxyethyl, α-acetoxybenzyl, α-pivaloyloxyethyl, ethoxycarbonyloxymethyl, α-ethoxycarbonyloxyethyl, dimethylaminomethyl, diethylaminomethyl, phthalidyl or dimethoxyphthalidyl groups.

31. A method according to claim 12, wherein the pharmaceutically acceptable salt is an alkali metal or alkaline earth metal salt.

32. A method according to claim 12 for the treatment of infections in the respiratory tract, urinary tract or soft tissues in humans.

33. A composition according to claim 10 in oral adminstration form.

34. A composition according to claim 10 in parenteral adminstration form.

35. A method according to claim 12, wherein the adminstration is oral.

36. A method according to claim 12, wherein the adminstration is parenteral.

37. A pharmaceutical composition according to claim 11, wherein the penicillin is ampicillin, amoxycillin, carbenicillin, piperacillin, azlocillin, mezlocillin or ticarcillin.

38. A pharmaceutical composition according to claim 11, wherein the cephalosporin is cephaloridine, cefoperazone or cefazolin.

39. A method according to claim 13, wherein the penicillin is ampicillin, amoxycillin, carbenicillin, piperacillin, azlocillin, mezlocillin or ticarcillin.

40. A method according to claim 13, wherein the cephalosporin is cephaloridine, cefoperazone or cefazolin.

* * * * *

UNITED STATES PATENT AND TRADEMARK OFFICE
CERTIFICATE OF CORRECTION

PATENT NO. : 4,798,828
DATED : January 17, 1989
INVENTOR(S) : Neal F. Osborne

It is certified that error appears in the above-identified patent and that said Letters Patent is hereby corrected as shown below:

Column 11, formula XIII, that portion of the formula reading

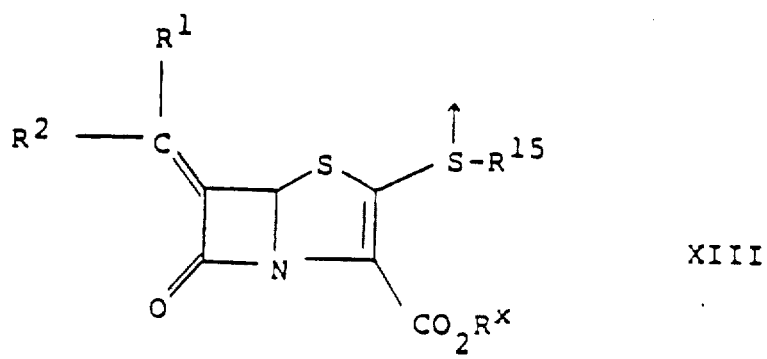

should read

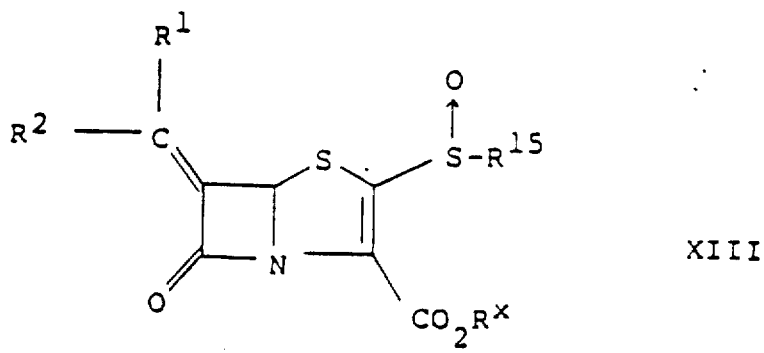

UNITED STATES PATENT AND TRADEMARK OFFICE
CERTIFICATE OF CORRECTION

PATENT NO. : 4,798,828

DATED : January 17, 1989

INVENTOR(S) : Neal F. Osborne

It is certified that error appears in the above-identified patent and that said Letters Patent is hereby corrected as shown below:

Column 20, line 58, delete "Preparatinn" and substitute therefor -- Preparation --.

Column 23, line 4, delete "Acetoxv" and substitute therefor -- Acetoxy --.

Column 43, line 5, after "O-" and before "%", insert -- 20 --.

UNITED STATES PATENT AND TRADEMARK OFFICE
CERTIFICATE OF CORRECTION

PATENT NO. : 4,798,828

DATED : January 17, 1989

INVENTOR(S) : Neal F. Osborne

It is certified that error appears in the above-identified patent and that said Letters Patent is hereby corrected as shown below:

Column 53, line 36, delete "nttrate" and substitute therefor -- nitrate --.

Claim 1, column 57, line 3, delete "oen" and substitute therefor -- one --;

line 23, after "di)-", delete "$(c_{1-6})$" and substitute therefor -- $(C_{1-6})$ --;

line 26, after "carboxy" and before "pharmaceuti-", insert --, --;

line 39, delete "form" and substitute therefor -- from --;

line 45, after "by" and before "to", insert -- up --; delete "give" and substitute therefor -- five --;

line 46, delete "selelcted form" and substitute therefor -- selected from --.

UNITED STATES PATENT AND TRADEMARK OFFICE
CERTIFICATE OF CORRECTION

PATENT NO. : 4,798,828

DATED : January 17, 1989

INVENTOR(S) : Neal F. Osborne

It is certified that error appears in the above-identified patent and that said Letters Patent is hereby corrected as shown below:

Claim 2, column 58, line 3, after "di)-" delete "$(C_{1-6})$" and substitute therefor -- $(C_{1-6})$ --;

line 5, delete "alkylosulphinyl" and substitute therefor -- alkylsulphinyl --;

line 6, delete "heterocycylthio" and substitute therefor -- heterocyclylthio --;

line 13, delete "alynyl" and substitute therefor -- alkynyl --;

line 15, delete "alknoyloxy" and substitute therefor -- alkanoyloxy --;

line 17, delete "alkylsuophi-" and substitute therefor -- alkylsulphi --;

line 20, after "carboxy" and before "pharmaceuti", insert -- , --;

line 21, after "salts" and before "pharmaceutically", insert -- , --;

UNITED STATES PATENT AND TRADEMARK OFFICE
CERTIFICATE OF CORRECTION

PATENT NO. : 4,798,828
DATED : January 17, 1989
INVENTOR(S) : Neal F. Osborne

It is certified that error appears in the above-identified patent and that said Letters Patent is hereby corrected as shown below:

line 42, delete "phneyl" and substitute therefor -- phenyl --; and line 46, delete "aryltho" and substitute therefor -- arylthio --.

Claim 6, column 59, line 3, delete the space between "yl)" and "me-";

line 5, delete the space between "yl)" and "me-".

Claim 7, column 59, line 45, after "which" and before "option-", insert -- are --;

column 60, line 2, delete "hydroy" and substitute therefor -- hydroxy --;

line 3, delete "koxyarbonyl" and substitute therefor -- koxycarbonyl --;

UNITED STATES PATENT AND TRADEMARK OFFICE
CERTIFICATE OF CORRECTION

PATENT NO. : 4,798,828

DATED : January 17, 1989

INVENTOR(S) : Neal F. Osborne

Page 6 of 11

It is certified that error appears in the above-identified patent and that said Letters Patent is hereby corrected as shown below:

line 4, delete "alkylthiuo" and substitute therefor -- alkylthio --;

line 6, delete "protectign" and substitute therefor -- protecting --;

line 27, delete "arboxy" and substitute therefor -- carboxy --;

line 28, delete "alkoxyarbonyl" and substitute therefor -- alkoxycarbonyl --; between "alkyl" and "$(C_{1-6})$", insert -- , --;

line 29, delete the space between "alkyl" and "carbonyloxy".

Claim 10, column 61, line 23, delete "suophamoyl" and substitute therefor -- sulphamoyl --;

line 25, delete "saslts" and substitute therefor -- salts --;

UNITED STATES PATENT AND TRADEMARK OFFICE
CERTIFICATE OF CORRECTION

PATENT NO. : 4,798,828

DATED : January 17, 1989

INVENTOR(S) : Neal F. Osborne

It is certified that error appears in the above-identified patent and that said Letters Patent is hereby corrected as shown below:

line 33, delete "alkylsulo-" and substitute therefor -- alkylsul --;

line 41, delete "(Chd 1-10)" and substitute therefor -- ($C_{1-10}$) --;

line 58, between "alkyl" and "phenyl", insert -- , --.

Claim 12, column 62, line 1, delete "of" and substitute therefor -- or --;

line 24, delete "alikylsulphinyl" and substitute therefor -- alkylsulphinyl --;

line 28, after "carboxy" and before "esters", insert -- salts, (x) pharmaceutically acceptable carboxy --;

line 31, delete "alkylnyl" and substitute therefor -- alkynyl --;

UNITED STATES PATENT AND TRADEMARK OFFICE
CERTIFICATE OF CORRECTION

PATENT NO. : 4,798,828
DATED : January 17, 1989
INVENTOR(S) : Neal F. Osborne

It is certified that error appears in the above-identified patent and that said Letters Patent is hereby corrected as shown below:

line 47, delete "alkylthiuo" and substitute therefor -- alkylthio --;

line 50, delete the space between "h" and "eterocycyl";

line 58, delete "arylthoi" and substitute therefor -- arylthio --;

line 59, delete "napthyl" and substitute therefor -- naphthyl --;

line 60, delete "give" and substitute therefor -- five --; and line 62, delete "haloo" and substitute therefor -- halo --.

UNITED STATES PATENT AND TRADEMARK OFFICE
CERTIFICATE OF CORRECTION

PATENT NO. : 4,798,828

DATED : January 17, 1989

INVENTOR(S) : Neal F. Osborne

It is certified that error appears in the above-identified patent and that said Letters Patent is hereby corrected as shown below:

Claim 13, column 62, line 68, delete "of" and substitute therefor -- or --;

column 63, line 3, delete "anitbiotic" and substitute therefor -- antibiotic --.

Claim 15, column 63, line 8, delete "isozazo-" and substitute therefor -- isoxazo --; and line 13, delete "tetrazoloyl" and substitute therefor -- tetrazolyl --.

Claim 17, column 63, line 49, before "$C_{1-6}$", insert -- ( --.

Claim 24, column 64, line 44, delete "ethoxycarbonylx-" and substitute therefor -- ethoxycarbonylo --; and line 45, delete "oymethyl" and substitute therefor -- xymethyl --.

UNITED STATES PATENT AND TRADEMARK OFFICE
CERTIFICATE OF CORRECTION

PATENT NO. : 4,798,828
DATED : January 17, 1989
INVENTOR(S) : Neal F. Osborne

It is certified that error appears in the above-identified patent and that said Letters Patent is hereby corrected as shown below:

Claim 28, column 64, line 61, after "$R^3$ is a", insert -- hydrogen, methyl, ethyl, propyl, methylthio, ethylthio --;

column 65, line 2, delete "pyridimidylthiuo" and substitute therefor -- pyrimidylthio --.

Claim 29, column 65, line 21, delete "phenyl" and substitute therefor -- phenylene --.

Column 17, third line under "Preparation 1(d), after "-4-", delete "tritylthicazeti-" and substitute therefor -- tritylthioazeti- --.

UNITED STATES PATENT AND TRADEMARK OFFICE
CERTIFICATE OF CORRECTION

PATENT NO. : 4,798,828

DATED : January 17, 1989

INVENTOR(S) : Neal F. Osborne

It is certified that error appears in the above-identified patent and that said Letters Patent is hereby corrected as shown below:

Column 53, line 61, delete "methylpyazol" and substitute therefor -- methylpyrazol --.

Signed and Sealed this

Twenty-seventh Day of March, 1990

Attest:

JEFFREY M. SAMUELS

Attesting Officer

Acting Commissioner of Patents and Trademarks